United States Patent
Kobayashi et al.

(10) Patent No.: US 9,796,709 B2
(45) Date of Patent: Oct. 24, 2017

(54) 5-HYDROXY-4-(TRIFLUOROMETHYL) PYRAZOLOPYRIDINE DERIVATIVE

(71) Applicant: Daiichi Sankyo Company, Limited, Chuo-ku, Tokyo (JP)

(72) Inventors: Hideki Kobayashi, Toshima-ku (JP); Masami Arai, Naka-gun (JP); Toshio Kaneko, Yokohama (JP); Naoki Terasaka, Saitama (JP)

(73) Assignee: Daiichi Sankyo Company, Limited, Chuo-Ku (JP)

( * ) Notice: Subject to any disclaimer, the term of this patent is extended or adjusted under 35 U.S.C. 154(b) by 0 days.

(21) Appl. No.: 15/100,654

(22) PCT Filed: Dec. 12, 2014

(86) PCT No.: PCT/JP2014/082943
§ 371 (c)(1),
(2) Date: Jun. 1, 2016

(87) PCT Pub. No.: WO2015/087994
PCT Pub. Date: Jun. 18, 2015

(65) Prior Publication Data
US 2016/0376267 A1 Dec. 29, 2016

(30) Foreign Application Priority Data
Dec. 13, 2013 (JP) .................... 2013-258008

(51) Int. Cl.
A61K 31/44 (2006.01)
C07D 471/04 (2006.01)

(52) U.S. Cl.
CPC .................. *C07D 471/04* (2013.01)

(58) Field of Classification Search
USPC .......................... 546/119; 514/303
See application file for complete search history.

(56) References Cited

U.S. PATENT DOCUMENTS 7,799,782 B2 * 9/2010 Munson ............. C07D 231/56
514/234.5
9,150,575 B2 * 10/2015 Kobayashi .......... C07D 471/04

FOREIGN PATENT DOCUMENTS

WO 2008/002591 A2 1/2008
WO 2012/028243 A1 3/2012

OTHER PUBLICATIONS

Official Letter dated Oct. 19, 2016, issued in corresponding Columbian Application No. 16-166.914, filed Dec. 12, 2016, 5 pages.
Badimon, J.J., et al., "Regression of Atherosclerotic Lesions by High Density Lipoprotein Plasma Fraction in the Cholesterol-Fed Rabbit," Journal of Clinical Investigation 85(4):1234-1241, Apr. 1990.
Balicki, R., "Studies in the Field of Nitrogen Heterocyclic Compounds. Part. XI. Abnormal Cyclocondensation of Ethyl 4,4,4-trifluoroacetoacetate With Aminopyrazoles," Polish Journal of Chemistry 57:789-797, 1983.
International Search Report and Written Opinion dated Feb. 17, 2015, issued in corresponding International Application No. PCT/JP2014/082943, filed Dec. 12, 2014, 18 pages.
Iwata, A., et al., "Antiatherogenic Effects of Newly Developed Apolipoprotein A-I Mimetic Peptide/Phospholipid Complexes Against Aortic Plaque Burden in Watanabe-Heritable Hyperlipidemic Rabbits," Atherosclerosis 218(2):300-307, Oct. 2011.
Matsuura, F., et al., "HDL From CETP-Deficient Subjects Shows Enhanced Ability to Promote Cholesterol Efflux from Macrophages in an apoE- and ABCG1-Dependent Pathway," Journal of Clinical Investigation 116(5):1435-1442, May 2006.
Ross, R., "Cell Biology of Atherosclerosis," Annual Reviews of Physiology 57:791-804, 1995.
Steinberg, D., "Low Density Lipoprotein Oxidation and Its Pathobiological Significance," Journal of Biological Chemistry 272(34):20963-20966, Aug. 1997.
Yvan-Charvet, L., et al., "Inhibition of Cholesteryl Ester Transfer Protein by Torcetrapib Modestly Increases Macrophage Cholesterol Efflux to HDL," Arteriosclerosis, Thrombosis, and Vascular Biology 27(5):1132-1138, May 2007.
International Preliminary Report on Patentability dated Jun. 14, 2016, issued in corresponding International Application No. PCT/JP2014/082943, filed Dec. 12, 2014, 6 pages.
Extended European Search Report dated Apr. 11, 2017, issued in European Application No. 14869320.3, filed Dec. 12, 2014, 5 pages.

* cited by examiner

*Primary Examiner* — Rei-Tsang Shiao
(74) *Attorney, Agent, or Firm* — Christensen O'Connor Johnson Kindness PLLC

(57) ABSTRACT

A compound represented by the general formula (I) or a pharmacologically acceptable salt thereof has an excellent LCAT-activating effect and is useful as an active ingredient in a therapeutic or prophylactic agent for arteriosclerosis, arteriosclerotic heart disease, coronary heart disease (including heart failure, myocardial infarction, angina pectoris, cardiac ischemia, cardiovascular disturbance, and restenosis caused by angiogenesis), cerebrovascular disease (including stroke and cerebral infarction), peripheral vascular disease (including diabetic vascular complications), dyslipidemia, hypo-HDL-cholesterolemia, hyper-LDL-cholesterolemia, or renal disease, particularly, an anti-arteriosclerotic agent, wherein R is an optionally substituted aryl group or an optionally substituted heteroaryl group, and $R^1$ is a hydrogen atom or a hydroxy group.

[Formula 1]

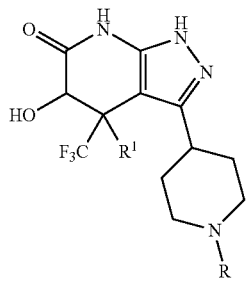

33 Claims, 1 Drawing Sheet

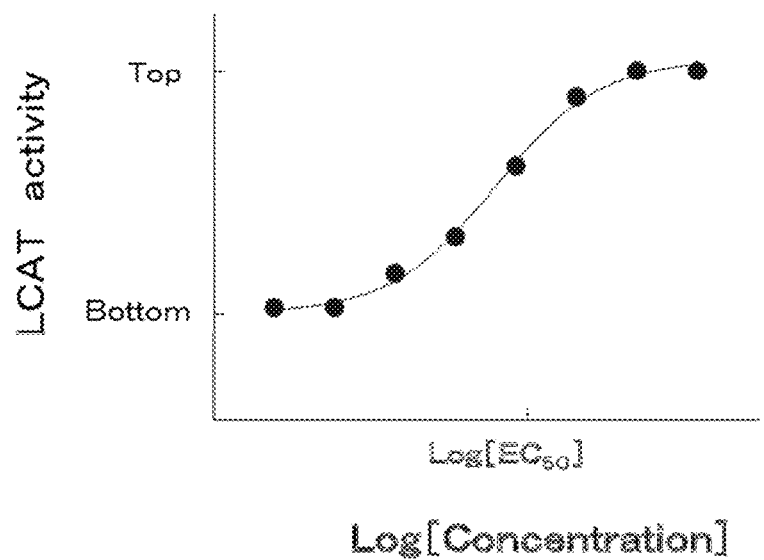

5-HYDROXY-4-(TRIFLUOROMETHYL) PYRAZOLOPYRIDINE DERIVATIVE

TECHNICAL FIELD

The present invention relates to a pyrazolopyridine derivative or a pharmacologically acceptable salt thereof which has an excellent lecithin-cholesterol acetyltransferase (hereinafter, referred to as LCAT)-activating effect (preferably, reversible LCAT-activating effect).

BACKGROUND ART

Cardiovascular diseases (e.g., cardiac disease, cerebrovascular disease, and renal disease) caused by hypertension, dyslipidemia, diabetes mellitus, or the like are significant problems for developed countries. Antihypertensive, antidyslipidemic, and antidiabetic drugs are used in the treatment of the diseases hypertension, dyslipidemia, and hyperglycemia, respectively. In the clinical setting, α and β blockers, diuretics, calcium antagonists, ACE inhibitors, and A-II antagonists, etc. are used as antihypertensive drugs; HMG-CoA reductase inhibitors, anion exchange resins, nicotinic acid derivatives, probucol, and fibrates, etc. are used as antidyslipidemic drugs; and insulins, sulfonylureas, metformin, glitazones, and DPP4 inhibitors, etc. are used as antidiabetic drugs. These drugs contribute to the regulation of blood pressure or lipid or glucose levels in the blood. Nonetheless, even the use of these medicaments has not produced a great improvement in the death rates attributed to cardiac disease, cerebrovascular disease, and renal disease. Thus, there has been a demand for the development of better therapeutic drugs for these diseases.

A direct risk factor for cardiovascular diseases is atherosclerosis associated with thickening of the arterial wall. This thickening is caused by plaque formation resulting from the accumulation of oxidized low-density lipoprotein (hereinafter, referred to as LDL) cholesterol in macrophages and the like in the arterial wall (Non-patent Literatures 1 and 2). This plaque atherosclerosis inhibits blood flow and promotes the formation of blood clots.

The results of many epidemiologic studies indicate that serum concentrations of lipoproteins are associated with diseases such as dyslipidemia and arteriosclerosis (e.g., Non-patent Literature 3). Both an increased concentration of LDL cholesterol in the blood and a decreased concentration of high-density lipoprotein (hereinafter, referred to as HDL) cholesterol in the blood are risk factors for coronary diseases.

In peripheral tissues, HDL promotes efflux of cholesterol, which is in turn esterified by LCAT on HDL to produce cholesteryl ester. Increased activity of LCAT promotes cholesterol efflux from macrophages (e.g., Non-patent Literatures 4 and 5). Accordingly, drugs that increase LCAT activity are considered to be useful as medicaments for the treatment or prophylaxis of diseases such as dyslipidemia and arteriosclerosis.

A peptide compound (e.g., Non-patent Literature 6) and, for example, the compound described in Patent Literature 1 as a small molecule, are known as such drugs that increase LCAT activity.

The compound described in Patent Literature 2 is known as a compound having a pyrazolopyridine skeleton. Patent Literature 2 makes no mention of an LCAT-activating effect, though the literature discloses an anti-LPA receptor effect.

CITATION LIST

Patent Literature

Patent Literature 1: WO2008/002591
Patent Literature 2: WO2012/028243

Non-Patent Literature

Non-patent Literature 1: Ross, R., Annu. Rev. Physiol. 1995, Vol. 57, p. 791-804
Non-patent Literature 2: Steinberg, D., J. Biol. Chem. 1997, Vol. 272, p. 20963-20966
Non-patent Literature 3: Badimon, J. Clin. Invest., 1990, Vol. 85, p. 1234-1241
Non-patent Literature 4: Matsuura, F., J. Clin. Invest. 2006, Vol. 116, p. 1435-1442
Non-patent Literature 5: Yvan-Charvet, L., Arterioscler. Thromb. Vasc. Biol. 2007, Vol. 27, p. 1132-1138
Non-patent Literature 6: Iwata, A., Atherosclerosis. 2011, Vol. 218, p. 300-307

SUMMARY OF INVENTION

Technical Problem

Currently known compounds having an LCAT-activating effect are less than satisfactory in terms of safety and efficacy. Thus, there has been a strong demand for LCAT activators excellent in safety and efficacy.

Solution to Problem

The present inventors have conducted various syntheses and studies with the aim of obtaining a novel anti-arteriosclerotic drug that has an excellent LCAT-activating effect and directly promotes the efflux of cholesterol from macrophages. As a result, the present inventors have completed the present invention by finding that a pyrazolopyridine derivative having a particular structure or a pharmacologically acceptable salt thereof has an excellent LCAT-activating effect.

The present invention provides a pyrazolopyridine derivative or a pharmacologically acceptable salt thereof which has an excellent LCAT-activating effect (preferably, reversible LCAT-activating effect), and a medicament comprising the same.

Specifically, the present invention relates to:
(1) a compound represented by the general formula (I) or a pharmacologically acceptable salt thereof:

[Formula 1]

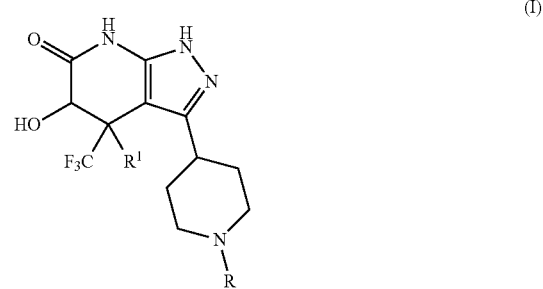

wherein R represents an optionally substituted aryl group (the substituent(s) is 1 to 3 identical or different groups selected from the group consisting of a halogen atom, a $C_{1-6}$ alkyl group, a $C_{3-7}$ cycloalkyl group, a trifluoromethyl group, a difluoromethoxy group, a trifluoromethoxy group, a cyano group, a $C_{1-6}$ alkoxy group, a $C_{3-7}$ cycloalkyl group, a phenyl group, a $C_{2-7}$ alkoxycarbonyl group, a benzyloxycarbonyl group, a di($C_{1-6}$ alkyl)aminocarbonyl group, and a di($C_{1-6}$ alkyl)amino group) or
an optionally substituted heteroaryl group (the heteroaryl is a 5- or 6-membered ring; the heteroatom(s) on the ring of the heteroaryl group is 1 or 2 nitrogen atoms, and the ring optionally further contains one nitrogen atom, oxygen atom, or sulfur atom; and the substituent(s) is 1 or 2 identical or different groups selected from the group consisting of a halogen atom, a $C_{1-6}$ alkyl group, a $C_{3-7}$ cycloalkyl group, a trifluoromethyl group, a difluoromethoxy group, a trifluoromethoxy group, a cyano group, a $C_{1-6}$ alkoxy group, a $C_{3-7}$ cycloalkoxy group, a phenyl group, a $C_{2-7}$ alkoxycarbonyl group, a benzyloxycarbonyl group, a di($C_{1-6}$ alkyl)aminocarbonyl group, and a di($C_{1-6}$ alkyl)amino group), and $R^1$ represents a hydrogen atom or a hydroxy group;

(2) the compound according to (1) or a pharmacologically acceptable salt thereof, wherein R is an optionally substituted aryl group (the substituent(s) is 1 to 3 identical or different groups selected from the group consisting of a halogen atom, a $C_{1-6}$ alkyl group, a $C_{3-7}$ cycloalkyl group, a trifluoromethyl group, a difluoromethoxy group, a trifluoromethoxy group, a cyano group, a $C_{1-6}$ alkoxy group, a $C_{3-7}$ cycloalkoxy group, a phenyl group, a $C_{2-7}$ alkoxycarbonyl group, a benzyloxycarbonyl group, a di($C_{1-6}$ alkyl)aminocarbonyl group, and a di($C_{1-6}$ alkyl)amino group);

(3) the compound according to (1) or a pharmacologically acceptable salt thereof, wherein R is a substituted aryl group (the substituent(s) is 1 or 2 identical or different groups selected from the group consisting of a chlorine atom, a fluorine atom, a $C_{1-3}$ alkyl group, a trifluoromethyl group, a difluoromethoxy group, a trifluoromethoxy group, a cyano group, and a $C_{1-3}$ alkoxy group);

(4) the compound according to (1) or a pharmacologically acceptable salt thereof, wherein R is a substituted phenyl group (the substituent(s) is 1 or 2 identical or different groups selected from the group consisting of a chlorine atom, a difluoromethoxy group, a trifluoromethoxy group, and a cyano group);

(5) the compound according to (1) or a pharmacologically acceptable salt thereof, wherein R is a substituted phenyl group (the substituent(s) is 1 or 2 identical or different groups selected from the group consisting of a difluoromethoxy group, a trifluoromethoxy group, and a cyano group);

(6) the compound according to (1) or a pharmacologically acceptable salt thereof, wherein R is an optionally substituted heteroaryl group (the heteroaryl is a 5- or 6-membered ring; the heteroatom(s) on the ring of the heteroaryl group is 1 or 2 nitrogen atoms, and the ring optionally further contains one nitrogen atom, oxygen atom, or sulfur atom; and the substituent(s) is 1 or 2 identical or different groups selected from the group consisting of a halogen atom, a $C_{1-6}$ alkyl group, a $C_{3-7}$ cycloalkyl group, a trifluoromethyl group, a difluoromethoxy group, a trifluoromethoxy group, a cyano group, a $C_{1-6}$ alkoxy group, a $C_{3-7}$ cycloalkoxy group, a phenyl group, a $C_{2-7}$ alkoxycarbonyl group, a benzyloxycarbonyl group, a di($C_{1-6}$ alkyl)aminocarbonyl group, and a di($C_{1-6}$ alkyl)amino group);

(7) the compound according to (1) or a pharmacologically acceptable salt thereof, wherein R is a substituted heteroaryl group (the heteroaryl is a 5- or 6-membered ring; the heteroatom on the ring of the heteroaryl group is one nitrogen atom, and the ring optionally further contains one nitrogen atom, oxygen atom, or sulfur atom; and the substituent(s) is 1 or 2 identical or different groups selected from the group consisting of a halogen atom, a $C_{1-3}$ alkyl group, a $C_{3-6}$ cycloalkyl group, a trifluoromethyl group, a difluoromethoxy group, a trifluoromethoxy group, a cyano group, a $C_{1-3}$ alkoxy group, a $C_{2-4}$ alkoxycarbonyl group, and a benzyloxycarbonyl group);

(8) the compound according to (1) or a pharmacologically acceptable salt thereof, wherein R is a substituted pyridyl, pyrimidyl, pyrazinyl, pyridazinyl, thiadiazolyl, or thiazolyl group (the substituent(s) is 1 or 2 identical or different groups selected from the group consisting of a chlorine atom, a fluorine atom, a $C_{1-3}$ alkyl group, a cyclopropyl group, a trifluoromethyl group, a difluoromethoxy group, a trifluoromethoxy group, a cyano group, a $C_{1-3}$ alkoxy group, a $C_{2-4}$ alkoxycarbonyl group, and a benzyloxycarbonyl group);

(9) the compound according to (1) or a pharmacologically acceptable salt thereof, wherein R is a substituted pyridyl, pyrimidyl, pyrazinyl, or pyridazinyl group (the substituent(s) is 1 or 2 identical or different groups selected from the group consisting of an isopropyl group, a trifluoromethyl group, a difluoromethoxy group, a cyano group, and an isopropoxy group);

(10) the compound according to (1) or a pharmacologically acceptable salt thereof, wherein R is a pyridyl, pyrimidyl, pyrazinyl, or thiadiazolyl group substituted by a trifluoromethyl group;

(11) the compound according to (1) or a pharmacologically acceptable salt thereof, wherein R is a pyridyl, pyrimidyl, or pyrazinyl group substituted by a trifluoromethyl group;

(12) the compound according to any one of (1) to (11) or a pharmacologically acceptable salt thereof, wherein $R^1$ is a hydrogen atom;

(13) the compound according to (12) or a pharmacologically acceptable salt thereof, wherein the compound or the salt is selected from the group consisting of:

5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one, 5-hydroxy-3-[1-(5-isopropoxypyridin-2-yl)piperidin-4-yl]-4-(trifluoromethyl)-1,4,5,7-tetrahydro-6H-pyrazolo[3,4-b]pyridin-6-one, 5-hydroxy-4-(trifluoromethyl)-3-{1-[6-(trifluoromethyl)pyridazin-3-yl]piperidin-4-yl}-1,4,5,7-tetrahydro-6H-pyrazolo[3,4-b]pyridin-6-one, 5-hydroxy-3-{1-[2-isopropyl-6-(trifluoromethyl)pyrimidin-4-yl]piperidin-4-yl}-4-(trifluoromethyl)-1,4,5,7-tetrahydro-6H-pyrazolo[3,4-b]pyridin-6-one, 5-hydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one, 5-hydroxy-4-(trifluoromethyl)-3-{1-[2-(trifluoromethyl)pyrimidin-5-yl]piperidin-4-yl}-1, 4, tetrahydro-6H-pyrazolo[3,4-b]pyridin-6-one, 6-{4-[5-hydroxy-6-oxo-4-(trifluoromethyl)-4,5,6,7-tetrahydro-1H-pyrazolo[3,4-b]pyridin-3-yl]piperidin-yl}-4-(trifluoromethyl)pyridine-3-carbonitrile, 3-{1-[3-chloro-5-(trifluoromethyl)pyridin-2-yl]piperidin-4-yl}-5-hydroxy-4-(trifluoromethyl)-1,4,5,7-tetrahydro-6H-pyrazolo[3,4-b]pyridin-6-one, 5-hydroxy-4-(trifluoromethyl)-3-{1-[4-(trifluoromethyl)-1,3-thiazol-2-yl]piperidin-4-yl}-1,4,5,7-tetrahydro-6H-pyrazolo[3,4-b]pyridin-6-one, 5-hydroxy-4-(trifluoromethyl)-3-{1-[6-(trifluoromethyl)pyridin-2-yl]piperidin-4-yl}-1,4,5,7-tetrahydro-6H-pyrazolo[3,4-b]pyridin-6-one,
5-hydroxy-4-(trifluoromethyl)-3-{1-[4-(trifluoromethyl)pyridin-2-yl]piperidin-4-yl}-1,4,5,7-tetrahydro-6H-pyrazolo[3,4-b]pyridin-6-one,
3-[1-(5-chloropyridin-2-yl)piperidin-4-yl]-5-hydroxy-4-(trifluoromethyl)-1,4,5,7-tetrahydro-6H-pyrazolo[3,4-b]pyridin-6-one,
5-hydroxy-4-(trifluoromethyl)-3-{1-[6-(trifluoromethyl)pyridin-3-yl]piperidin-4-yl}-1,4,5,7-tetrahydro-6H-pyrazolo[3,4-b]pyridin-6-one,
hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one,
5-hydroxy-4-(trifluoromethyl)-3-{1-[6-(trifluoromethyl)pyrimidin-4-yl]piperidin-4-yl}-1,4,5,7-tetrahydro-6H-pyrazolo[3,4-b]pyridin-6-one,
5-hydroxy-3-[1-(6-isopropoxypyridazin-3-yl)piperidin-4-yl]-4-(trifluoromethyl)-1,4,5,7-tetrahydro-6H-pyrazolo[3,4-b]pyridin-6-one,
5-hydroxy-3-[1-(6-isopropoxypyridazin-3-yl)piperidin-4-yl]-4-(trifluoromethyl)-1,4,5,7-tetrahydro-6H-pyrazolo[3,4-b]pyridin-6-one, and
3-[1-(2-cyclopropylpyrimidin-5-yl)piperidin-4-yl]-5-hydroxy-4-(trifluoromethyl)-1,4,5,7-tetrahydro-6H-pyrazolo[3,4-b]pyridin-6-one;

(14) the compound according to (12) or a pharmacologically acceptable salt thereof, wherein the compound or the salt is selected from the group consisting of:
(+)-cis-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one,
(+)-cis-5-hydroxy-4-(trifluoromethyl)-3-{1-[6-(trifluoromethyl)pyridazin-3-yl]piperidin-4-yl}-1, 4, tetrahydro-6H-pyrazolo[3,4-b]pyridin-6-one,
(+)-cis-5-hydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one,
(+)-cis-5-hydroxy-4-(trifluoromethyl)-3-{1-[2-(trifluoromethyl)pyrimidin-5-yl]piperidin-4-yl}-1, 4, tetrahydro-6H-pyrazolo[3,4-b]pyridin-6-one,
(+)-cis-6-{4-[5-hydroxy-6-oxo-4-(trifluoromethyl) 4,5,6,7-tetrahydro-1H-pyrazolo[3,4-b]pyridin-3-yl]piperidin-1-yl}-4-(trifluoromethyl)pyridine-3-carbonitrile,
(+)-cis-3-[1-(5-chloropyridin-2-yl)piperidin-4-yl]-5-hydroxy-4-(trifluoromethyl)-1,4,5,7-tetrahydro-6H-pyrazolo[3,4-b]pyridin-6-one,
(+)-cis-5-hydroxy-4-(trifluoromethyl)-3-{1-[6-(trifluoromethyl)pyridin-3-yl]piperidin-4-yl}-1,4,5,7-tetrahydro-6H-pyrazolo[3,4-b]pyridin-6-one,
(+)-cis-hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one,
(+)-cis-5-hydroxy-4-(trifluoromethyl)-3-{1-[6-(trifluoromethyl)pyrimidin-4-yl]piperidin-4-yl}-1,4,5,7-tetrahydro-6H-pyrazolo[3,4-b]pyridin-6-one,
(+)-cis-5-hydroxy-3-[1-(6-isopropoxypyridazin-3-yl)piperidin-4-yl]-4-(trifluoromethyl)-1,4,5,7-tetrahydro-6H-pyrazolo[3,4-b]pyridin-6-one,
(+)-cis-5-hydroxy-3-[1-(6-isopropoxypyridazin-3-yl)piperidin-4-yl]-4-(trifluoromethyl)-1,4,5,7-tetrahydro-6H-pyrazolo[3,4-b]pyridin-6-one, and
(+)-cis-3-[1-(2-cyclopropylpyrimidin-5-yl)piperidin-4-yl]-5-hydroxy-4-(trifluoromethyl)-1,4,5,7-tetrahydro-6H-pyrazolo[3,4-b]pyridin-6-one;

(15) the compound according to any one of (1) to (11) or a pharmacologically acceptable salt thereof, wherein $R^1$ is a hydroxy group;
(16) the compound according to (15) or a pharmacologically acceptable salt thereof, wherein the compound or the salt is selected from the group consisting of:
4,5-dihydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one, and
4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one; (17) the compound according to (15) or a pharmacologically acceptable salt thereof, wherein the compound or the salt is selected from the group consisting of:
(+)-4,5-dihydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one, and
(+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one;
(18) the compound according to (1) or a pharmacologically acceptable salt thereof, wherein R is a substituted phenyl group (the substituent(s) is 1 or 2 identical or different groups selected from the group consisting of a chlorine atom, a difluoromethoxy group, a trifluoromethoxy group, and a cyano group), and $R^1$ is a hydrogen atom;
(19) the compound according to (1) or a pharmacologically acceptable salt thereof, wherein R is a substituted phenyl group (the substituent(s) is 1 or 2 identical or different groups selected from the group consisting of a difluoromethoxy group, a trifluoromethoxy group, and a cyano group), and $R^1$ is a hydrogen atom;
(20) the compound according to (1) or a pharmacologically acceptable salt thereof, wherein R is a substituted pyridyl, pyrimidyl, pyrazinyl, pyridazinyl, thiadiazolyl, or thiazolyl group (the substituent(s) is 1 or 2 identical or different groups selected from the group consisting of a chlorine atom, a fluorine atom, a $C_{1-3}$ alkyl group, a cyclopropyl group, a trifluoromethyl group, a difluoromethoxy group, a trifluoromethoxy group, a cyano group, a $C_{1-3}$ alkoxy group, a $C_{2-4}$ alkoxycarbonyl group, and a benzyloxycarbonyl group), and $R^1$ is a hydrogen atom;
(21) the compound according to (1) or a pharmacologically acceptable salt thereof, wherein R is a substituted pyridyl, pyrimidyl, pyrazinyl, or pyridazinyl group (the substituent(s) is 1 or 2 identical or different groups selected from the group consisting of an isopropyl group, a trifluoromethyl group, a difluoromethoxy group, a cyano group, and an isopropoxy group), and $R^1$ is a hydrogen atom;
(22) the compound according to (1) or a pharmacologically acceptable salt thereof, wherein R is a pyridyl, pyrimidyl, or pyrazinyl group substituted by a trifluoromethyl group, and $R^1$ is a hydrogen atom;
(23) the compound according to (1) or a pharmacologically acceptable salt thereof, wherein R is a substituted phenyl group (the substituent(s) is 1 or 2 identical or different groups selected from the group consisting of a chlorine atom, a difluoromethoxy group, a trifluoromethoxy group, and a cyano group), and $R^1$ is a hydroxy group;
(24) the compound according to (1) or a pharmacologically acceptable salt thereof, wherein R is a substituted phenyl group (the substituent(s) is 1 or 2 identical or different groups selected from the group consisting of a difluoromethoxy group, a trifluoromethoxy group, and a cyano group), and $R^1$ is a hydroxy group;

(25) the compound according to (1) or a pharmacologically acceptable salt thereof, wherein R is a substituted pyridyl, pyrimidyl, pyrazinyl, pyridazinyl, thiadiazolyl, or thiazolyl group (the substituent(s) is 1 or 2 identical or different groups selected from the group consisting of a chlorine atom, a fluorine atom, a $C_{1-3}$ alkyl group, a cyclopropyl group, a trifluoromethyl group, a difluoromethoxy group, a trifluoromethoxy group, a cyano group, a $C_{1-3}$ alkoxy group, a $C_{2-4}$ alkoxycarbonyl group, and a benzyloxycarbonyl group), and $R^1$ is a hydroxy group;

(26) the compound according to (1) or a pharmacologically acceptable salt thereof, wherein R is a substituted pyridyl, pyrimidyl, pyrazinyl, or pyridazinyl group (the substituent(s) is 1 or 2 identical or different groups selected from the group consisting of an isopropyl group, a trifluoromethyl group, a difluoromethoxy group, a cyano group, and an isopropoxy group), and $R^1$ is a hydroxy group;

(27) the compound according to (1) or a pharmacologically acceptable salt thereof, wherein R is a pyridyl, pyrimidyl, or pyrazinyl group substituted by a trifluoromethyl group, and $R^1$ is a hydroxy group;

(28) the compound according to any one of (1) to (13) and (15) to (27) or a pharmacologically acceptable salt thereof, wherein the trifluoromethyl group at the 4-position of the pyrazolopyridine ring and the hydroxy group at the 5-position thereof are cis to each other;

(29) the compound according to any one of (1) to (13), (15), (16), and (18) to (28) or a pharmacologically acceptable salt thereof, wherein the optical rotation is (+);

(30) a pharmaceutical composition comprising a compound according to any one of (1) to (29) or a pharmacologically acceptable salt thereof as an active ingredient;

(31) a pharmaceutical composition for the prophylaxis or treatment of arteriosclerosis, arteriosclerotic heart disease, coronary heart disease, cerebrovascular disease, peripheral vascular disease, dyslipidemia, hypo-HDL-cholesterolemia, hyper-LDL-cholesterolemia, or renal disease, comprising a compound according to any one of (1) to (29) or a pharmacologically acceptable salt thereof as an active ingredient;

(32) a prophylactic or therapeutic agent for arteriosclerosis, comprising a compound according to any one of (1) to (29) or a pharmacologically acceptable salt thereof as an active ingredient;

(33) a prophylactic or therapeutic agent for dyslipidemia, comprising a compound according to any one of (1) to (29) or a pharmacologically acceptable salt thereof as an active ingredient;

(34) a prophylactic or therapeutic agent for a disease caused by an increased concentration of LDL cholesterol in the blood, comprising a compound according to any one of (1) to (29) or a pharmacologically acceptable salt thereof as an active ingredient;

(35) a prophylactic or therapeutic agent for a disease caused by a decreased concentration of HDL cholesterol in the blood, comprising a compound according to any one of (1) to (29) or a pharmacologically acceptable salt thereof as an active ingredient;

(36) an LCAT activator comprising a compound according to any one of (1) to (29) or a pharmacologically acceptable salt thereof as an active ingredient;

(37) a reversible LCAT activator comprising a compound according to any one of (1) to (29) or a pharmacologically acceptable salt thereof as an active ingredient;

(38) an anti-arteriosclerotic agent comprising a compound according to any one of (1) to (29) or a pharmacologically acceptable salt thereof as an active ingredient;

(39) a method for activating LCAT, comprising administering an effective amount of a compound according to any one of (1) to (29) or a pharmacologically acceptable salt thereof to a human;

(40) a method for prophylaxis or treatment of a disease, comprising administering an effective amount of a compound according to any one of (1) to (29) or a pharmacologically acceptable salt thereof to a human;

(41) a method for prophylaxis or treatment of arteriosclerosis, comprising administering an effective amount of a compound according to any one of (1) to (29) or a pharmacologically acceptable salt thereof to a human;

(42) a method for prophylaxis or treatment of dyslipidemia, comprising administering an effective amount of a compound according to any one of (1) to (29) or a pharmacologically acceptable salt thereof to a human;

(43) a method for prophylaxis or treatment of a disease caused by an increased concentration of LDL cholesterol in the blood, comprising administering an effective amount of a compound according to any one of (1) to (29) or a pharmacologically acceptable salt thereof to a human;

(44) a method for prophylaxis or treatment of a disease caused by a decreased concentration of HDL cholesterol in the blood, comprising administering an effective amount of a compound according to any one of (1) to (29) or a pharmacologically acceptable salt thereof to a human;

(45) the compound according to any one of (1) to (29) or a pharmacologically acceptable salt thereof for use in a method for treatment or prophylaxis of arteriosclerosis;

(46) the compound according to any one of (1) to (29) or a pharmacologically acceptable salt thereof for use in a method for treatment or prophylaxis of dyslipidemia;

(47) the compound according to any one of (1) to (29) or a pharmacologically acceptable salt thereof for use in a method for treatment or prophylaxis of a disease caused by an increased concentration of LDL cholesterol in the blood; and

(48) the compound according to any one of (1) to (29) or a pharmacologically acceptable salt thereof for use in a method for treatment or prophylaxis of a disease caused by a decreased concentration of HDL cholesterol in the blood.

Hereinafter, substituents in the compound (I) of the present invention will be defined.

The compound (I) of the present invention encompasses both of a compound represented by the formula (I) and a compound represented by the formula, which is a tautomer thereof:

[Formula 2]

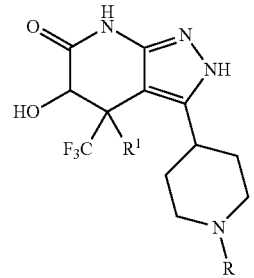

(Ix)

In the present application, a compound (I) including any such tautomer is also represented by the structural formula (I) and its corresponding chemical name for the sake of convenience, unless otherwise specified. The compound (I) of the present application also encompasses any isomer of an additional tautomer (amide-imide acid) of the compound (I) of the present invention. In the present application, a compound (I) including any such isomer is also represented by the structural formula (I) and its corresponding chemical name for the sake of convenience.

In the compound (I) of the present invention, the "aryl group" is, for example, a phenyl group or a naphthyl group and is preferably a phenyl group.

In the compound (I) of the present invention, the "halogen atom" refers to a fluorine atom, a chlorine atom, a bromine atom, or an iodine atom and is preferably a fluorine atom or a chlorine atom, more preferably a chlorine atom.

In the compound (I) of the present invention, the "$C_{1-6}$ alkyl group" refers to a linear or branched saturated hydrocarbon group having 1 to 6 carbon atoms. Examples thereof can include a methyl group, an ethyl group, a propyl group, an isopropyl group, a butyl group, a sec-butyl group, a tert-butyl group, an isobutyl group, a pentyl group, and a hexyl group. The $C_{1-6}$ alkyl group is preferably a linear or branched saturated hydrocarbon group having 1 to 3 carbon atoms ($C_{1-3}$ alkyl group), more preferably a methyl group.

In the compound (I) of the present invention, the "$C_{3-7}$ cycloalkyl group" refers to a cyclic saturated hydrocarbon group having 3 to 7 carbon atoms, such as a cyclopropyl group, a cyclobutyl group, a cyclopentyl group, or a cyclohexyl group, and is preferably a cyclic saturated hydrocarbon group having 3 to 6 carbon atoms ($C_{3-6}$ cycloalkyl group), more preferably a cyclopropyl group.

In the compound (I) of the present invention, the "$C_{1-6}$ alkoxy group" refers to an oxygen atom bonded by the above-mentioned "$C_{1-6}$ alkyl group". Examples thereof can include a methoxy group, an ethoxy group, a propoxy group, isopropoxy group and a butoxy group. The $C_{1-6}$ alkoxy group is preferably an oxygen atom bonded by the above-mentioned "$C_{1-3}$ alkyl group" ($C_{1-3}$ alkoxy group), more preferably a methoxy group.

In the compound (I) of the present invention, the "$C_{3-7}$ cycloalkoxy group" refers to an oxygen atom bonded by the above-mentioned "$C_{3-7}$ cycloalkyl group". Examples thereof can include a cyclopropyloxy group, a cyclobutyloxy group, a cyclopentyloxy group, a cyclohexyloxy group, and a cycloheptyloxy group.

In the compound (I) of the present invention, the "$C_{2-7}$ alkoxycarbonyl group" refers to a carbonyl group bonded by the above-mentioned "$C_{1-6}$ alkoxy group". Examples thereof can include a methoxycarbonyl group, an ethoxycarbonyl group, a propoxycarbonyl group, and a butoxycarbonyl group. The $C_{2-7}$ alkoxycarbonyl group is preferably a carbonyl group bonded by the above-mentioned "$C_{1-3}$ alkoxy group" ($C_{2-4}$ alkoxycarbonyl group), more preferably a methoxycarbonyl group or an ethoxycarbonyl group.

In the compound (I) of the present invention, the "di($C_{1-6}$ alkyl)amino group" refers to an amino group bonded by two identical or different above-mentioned "$C_{1-6}$ alkyl groups". The di($C_{1-6}$ alkyl)amino group is preferably a dimethylamino group.

In the compound (I) of the present invention, the "di($C_{1-6}$ alkyl)aminocarbonyl group" refers to a carbonyl group bonded by the above-mentioned "di($C_{1-6}$ alkyl)amino group". The di($C_{1-6}$ alkyl)aminocarbonyl group is preferably a dimethylaminocarbonyl group.

In the compound (I) of the present invention, the "heteroaryl group (the heteroaryl is a 5- or 6-membered ring; the heteroatom(s) on the ring of the heteroaryl group is 1 or 2 nitrogen atoms, and the ring optionally further contains one nitrogen atom, oxygen atom, or sulfur atom)" can be, for example, a pyridyl group, a pyrazinyl group, a pyrimidyl group, a pyridazinyl group, an oxazolyl group, a thiazolyl group, an isoxazolyl group, an isothiazolyl group, a pyrrole group, a pyrazolyl group, an imidazolyl group, a triazolyl group, or a thiadiazolyl group. The heteroaryl group is preferably a 5- or 6-membered heteroaryl group (the heteroatom on the heteroaryl ring is one nitrogen atom; and the ring optionally further contains one nitrogen atom, oxygen atom, or sulfur atom), more preferably a pyridyl group, a pyrimidyl group, a pyrazinyl group, a pyridazinyl group, a thiadiazolyl group, or a thiazolyl group, even more preferably a pyridyl group, a pyrimidyl group, a pyrazinyl group, a pyridazinyl group, or a thiadiazolyl group, further preferably a pyridyl group, a pyrimidyl group, a pyrazinyl group, or a thiadiazolyl group, particularly preferably a pyridyl group, a pyrimidyl group, or a pyrazinyl group.

The compound (I) of the present invention has a basic group and can therefore form an acid-addition salt with a pharmacologically acceptable acid. In the present invention, examples of the "pharmacologically acceptable salt thereof" can include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, tartrate, oxalate, and maleate; and amino acid salts such as ornithine salt, glutamate, and aspartate.

The compound (I) of the present invention or a pharmacologically acceptable salt thereof, when left in the atmosphere, may form a hydrate by absorbing water. Such hydrates are also included in the scope of the present invention.

The compound (I) of the present invention or a pharmacologically acceptable salt thereof, when left in a solvent, may form a solvate after being recovered from the solvent. Such solvates are also included in the scope of the present invention.

The compound (I) of the present invention has optical isomers based on the asymmetric center in the molecule. These isomers of the compound of the present invention and mixtures of these isomers are all represented by a single formula, i.e., the general formula (I), unless otherwise specified. Thus, it should be understood that even these isomers and mixtures of these isomers are all included in the scope of the present invention.

The compound (I) of the present invention has geometric isomers based on the 4-5-position of the pyrazolopyridine ring. Both cis and trans forms are included in the present invention, unless otherwise specified. For example, both of the geometric forms are produced, and their instrumental data can be compared to determine their respective structures. In the present invention, the trifluoromethyl group at the 4-position and the hydroxy group at the 5-position are preferably cis to each other.

The compound (I) of the present invention may contain isotope(s) of one or more atoms constituting such a compound at a nonnatural ratio. Examples of the isotope include deuterium ($^2H$), tritium ($^3H$), iodine-125 ($^{125}I$), and carbon-14 ($^{14}C$). Alternatively, the compound may be radiolabeled with a radioisotope, for example, tritium ($^3H$), iodine-125 ($^{125}I$), or carbon-14 ($^{14}C$). Such a radiolabeled compound is useful as a therapeutic or prophylactic agent, a research reagent, for example, an assay reagent, and a diagnostic agent, for example, an in vivo diagnostic imaging agent. It should be understood that all isotopic variants of the compound of the present invention are included in the scope of the present invention, regardless of being radioactive or not.

Advantageous Effects of Invention

The compound represented by the general formula (I) of the present invention or a pharmacologically acceptable salt thereof has an excellent LCAT-activating effect and is useful as an active ingredient in a therapeutic or prophylactic agent for arteriosclerosis, arteriosclerotic heart disease, coronary heart disease (including heart failure, myocardial infarction, angina pectoris, cardiac ischemia, cardiovascular disturbance, and restenosis caused by angiogenesis), cerebrovascular disease (including stroke and cerebral infarction), peripheral vascular disease (including diabetic vascular complications), dyslipidemia, hypo-HDL-cholesterolemia, hyper-LDL-cholesterolemia, or renal disease, particularly, an anti-arteriosclerotic agent. The compound (I) of the present invention or a pharmacologically acceptable salt thereof has a high concentration in the blood (AUC, $C_{max}$) when administered to animals (humans, monkeys, etc.), and can be expected to exhibit excellent drug efficacy.

BRIEF DESCRIPTION OF DRAWING

FIG. 1 shows a dose-response curve for determining the 50% effective concentration ($EC_{50}$) of LCAT activation in Test Examples 1 and 2 of the present invention.

DESCRIPTION OF EMBODIMENTS

Hereinafter, typical methods for producing the compound (I) of the present invention and starting compounds for use in the production of the compound (I) of the present invention will be described. However, the present invention is not intended to be limited by these methods.

Production Method 1

Production Method 1 is a method for producing the compound (I) of the present invention from compound (II).

[Formula 3]

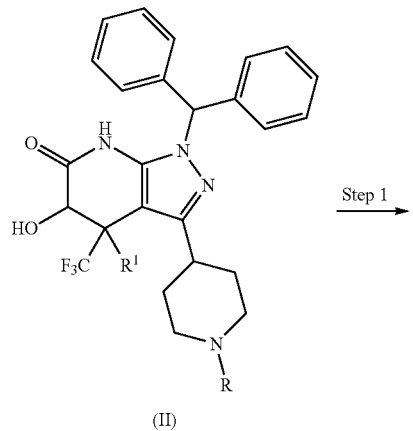

(II)

-continued

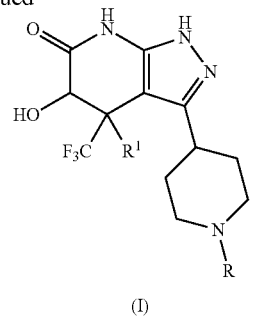

(I)

In these formulas, R and $R^1$ are as defined above.

(Step 1)

This step involves removing the diphenylmethyl group from compound (II) in an inert solvent to produce compound (I).

Examples of a reagent for use in the removal of diphenylmethyl group from the compound (II) include reagents capable of removing a trityl group as described in, for example, P. G. Wuts, T. W. Greene, Greene's Protective Groups in Organic Synthesis. Third Edition, 2006, John Wiley & Sons, Inc.

The solvent used in this step is preferably an alcohol such as methanol or ethanol; an ether such as tetrahydrofuran or 1,4-dioxane; an alkyl halide such as dichloromethane or chloroform; an ester such as ethyl acetate; an aromatic hydrocarbon such as toluene; or a mixed solvent thereof, more preferably an alkyl halide, even more preferably dichloromethane.

The reagent used in this step is preferably hydrochloric acid or trifluoroacetic acid, more preferably trifluoroacetic acid. A compound known as a cation scavenger such as triethylsilane, anisole, or thioanisole may be used as an additive.

The reaction temperature of this step is preferably 0° C. to 100° C., more preferably 0° C. to 50° C.

The reaction time of this step is preferably 5 minutes to 24 hours, more preferably 10 minutes to 6 hours.

Production Method 2

The intermediate (II) of the compound of the present invention wherein $R^1$ is a hydrogen atom can also be produced by the following method:

[Formula 4]

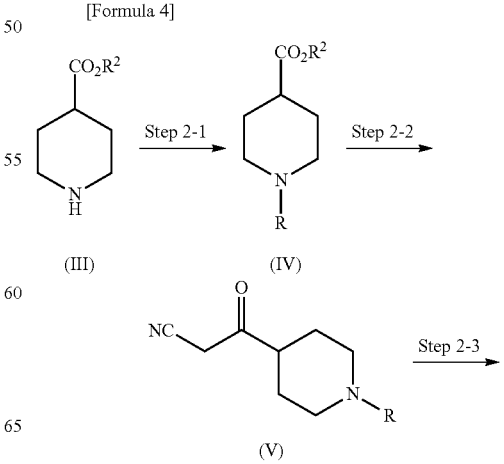

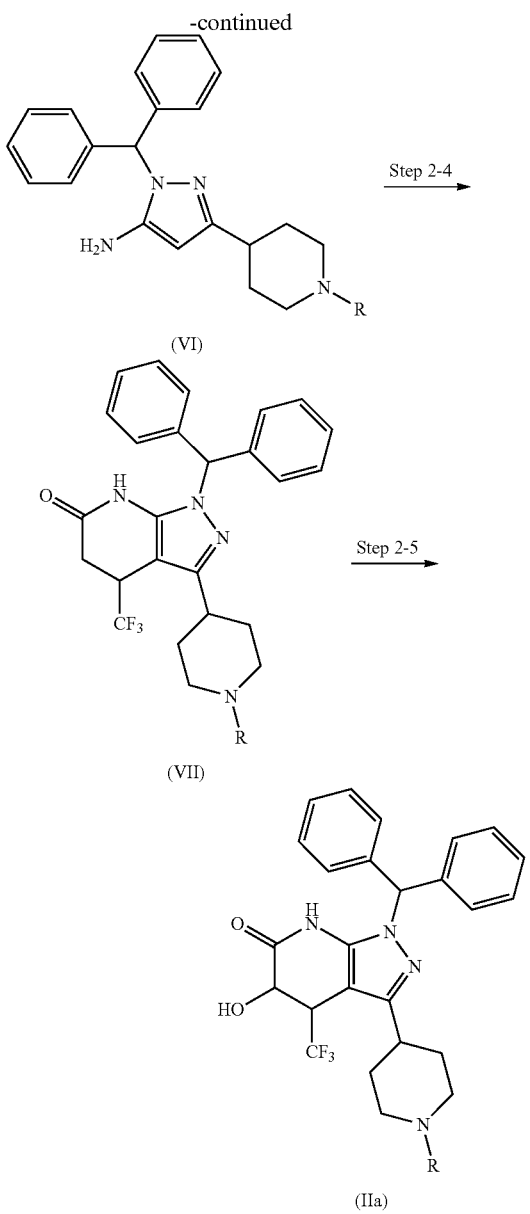

In these formulas, R is as defined above, and $R^2$ represents a methyl group or an ethyl group.

(Step 2-1)

(i) This step involves reacting compound (III) with an arylating agent or a heteroarylating agent through Buchwald-Hartwig reaction using a palladium catalyst in the presence of a ligand other than the palladium catalyst and a base in an inert solvent to produce compound (IV).

The palladium catalyst, the ligand, the base, and reaction conditions used in this step are not particularly limited as long as they are reagents and conditions for use in usual Buchwald-Hartwig reactions. The reagents and the conditions are described in, for example, A. R. Muci, S. L. Buchwald, Top. Curr. Chem. 2002, Vol. 219, p. 131.

The solvent used in this step is an ether such as diethyl ether, diisopropyl ether, tetrahydrofuran, dioxane, dimethoxyethane, or tert-butyl methyl ether; or an aromatic hydrocarbon such as benzene, toluene, or xylene. The solvent is preferably toluene or dioxane, more preferably toluene.

The palladium catalyst used in this step is preferably palladium(II) acetate or palladium(0) dibenzylideneacetone, more preferably palladium(0) dibenzylideneacetone.

The ligand used in this step is preferably tricyclohexylphosphine, 1,3-bis(diphenylphosphino)propane, 2,2'-bis(diphenylphosphanyl)1,1'-binaphthyl, 2-(dicyclohexylphosphino)biphenyl, or 2-dicyclohexylphosphino-2'-(N,N-dimethylamino)biphenyl, more preferably 2,2'-bis(diphenylphosphanyl)1,1'-binaphthyl.

The base used in this step is preferably sodium carbonate, potassium carbonate, cesium carbonate, sodium tert-butoxide or potassium tert-butoxide, more preferably sodium tert-butoxide.

The arylating agent or the heteroarylating agent used in this step refers to a compound represented by the formula R—Cl, R—Br, or R—I and is preferably a compound represented by the formula R—Cl or R—Br (wherein R is as defined above).

The reaction temperature of this step is preferably 20° C. to 150° C., more preferably 50° C. to the reflux temperature of the solvent.

In order to promote the reaction of this step, the reaction solution may be heated and may also be irradiated with microwaves.

The reaction time of this step is preferably 5 minutes to 120 hours, more preferably 10 minutes to 96 hours.

(ii) Alternatively, this step involves reacting compound (III) with an arylating agent or a heteroarylating agent in the presence of a base in an inert solvent to produce compound (IV).

The solvent used in this step can be a halogenated hydrocarbon such as dichloromethane, chloroform, carbon tetrachloride, 1,2-dichloroethane, chlorobenzene, or dichlorobenzene; an ether such as diethyl ether, diisopropyl ether, tetrahydrofuran, dioxane, dimethoxyethane, or tert-butyl methyl ether; an aromatic hydrocarbon such as benzene, toluene, or xylene; an amide such as formamide, N,N-dimethylformamide, dimethylacetamide, N-methyl-2-pyrrolidone, or hexamethylphosphortriamide; or a sulfoxide such as dimethyl sulfoxide. The solvent is preferably an amide or a sulfoxide, more preferably N,N-dimethylformamide or dimethyl sulfoxide.

The base used in this step can be an organic base such as triethylamine, diisopropylethylamine, 1,8-diazabicyclo[5.4.0]-7-undecene, N-methylmorpholine, pyridine, dimethylaminopyridine, or 2,6-lutidine. The base is preferably triethylamine, diisopropylethylamine, 1,8-diazabicyclo[5.4.0]-7-undecene, pyridine, or dimethylaminopyridine.

The arylating agent or the heteroarylating agent used in this step refers to a compound represented by the formula R—F, R—Cl, or R—Br and is preferably a compound represented by the formula R—F or R—Cl (wherein R is as defined above).

The reaction temperature of this step is preferably 20° C. to 200° C.

In order to promote the reaction of this step, the reaction solution may be heated and may also be irradiated with microwaves.

The reaction time of this step is preferably 5 minutes to 120 hours, more preferably 10 minutes to 96 hours.

(Step 2-2)

This step involves reacting compound (IV) with acetonitrile using a base in an inert solvent to produce compound (V).

The solvent used in this step can be an ether such as diethyl ether, diisopropyl ether, tetrahydrofuran, dioxane, dimethoxyethane, or tert-butyl methyl ether; an aromatic hydrocarbon such as benzene, toluene, or xylene; an aliphatic hydrocarbon such as hexane; or a mixed solvent thereof. The solvent is preferably an ether, more preferably tetrahydrofuran.

The base used in this step can preferably be an inorganic base such as sodium hydride, sodium carbonate, potassium carbonate, or cesium carbonate; or an organic metal base such as sodium tert-butoxide, potassium tert-butoxide, or n-butyllithium. The base is more preferably sodium hydride or n-butyllithium.

The reaction temperature of this step is preferably −100° C. to 0° C., more preferably −78° C. to −40° C.

The reaction time of this step is preferably 5 minutes to 3 hours, more preferably 15 minutes to 2 hours.

(Step 2-3)

This step involves reacting compound (V) with a diphenylmethyl hydrazine compound in an inert solvent to produce compound (VI).

The solvent used in this step can be an alcohol such as methanol, ethanol, n-propanol, isopropanol, n-butanol, isobutanol, tert-butanol, isoamyl alcohol, octanol, cyclohexanol, 2-methoxyethanol, diethylene glycol, or glycerin; an aromatic hydrocarbon such as benzene, toluene, or xylene; or a mixed solvent thereof. The solvent is preferably an alcohol, more preferably ethanol.

The diphenylmethyl hydrazine compound used in this step can be, for example, anhydrous diphenylmethyl hydrazine, diphenylmethyl hydrazine hydrochloride, or diphenylmethyl hydrazine acetate. The diphenylmethyl hydrazine compound is preferably diphenylmethyl hydrazine hydrochloride or diphenylmethyl hydrazine acetate.

The reaction temperature of this step is preferably 20° C. to 120° C., more preferably 50° C. to the reflux temperature of the solvent.

The reaction time of this step is preferably 10 minutes to 24 hours, more preferably 1 hour to 5 hours.

(Step 2-4)

This step involves reacting compound (VI) with a trifluoroacetaldehyde equivalent and Meldrum's acid in an inert solvent to produce compound (VII).

The solvent used in this step can be an alcohol such as methanol, ethanol, n-propanol, isopropanol, n-butanol, isobutanol, tert-butanol, isoamyl alcohol, octanol, cyclohexanol, 2-methoxyethanol, diethylene glycol, or glycerin; an aromatic hydrocarbon such as benzene, toluene, or xylene; or a mixed solvent thereof. The solvent is preferably an alcohol, more preferably ethanol.

The trifluoroacetaldehyde equivalent used in this step can be, for example, trifluoroacetaldehyde alkyl hemiacetal or trifluoroacetaldehyde dialkyl acetal. The trifluoroacetaldehyde equivalent is preferably trifluoroacetaldehyde ethyl hemiacetal.

The reaction temperature of this step is preferably 0° C. to 100° C., more preferably 20° C. to the reflux temperature of the solvent.

The reaction time of this step is preferably 30 minutes to 24 hours, more preferably 1 hour to 6 hours.

(Step 2-5)

This step involves reacting compound (VII) with an oxidizing agent in the presence of a base in an inert solvent to produce compound (IIa).

The solvent used in this step can be an ether such as diethyl ether, diisopropyl ether, tetrahydrofuran, dioxane, dimethoxyethane, or tert-butyl methyl ether; an aromatic hydrocarbon such as benzene, toluene, or xylene; an aliphatic hydrocarbon such as hexane; or a mixed solvent thereof. The solvent is preferably an ether, more preferably tetrahydrofuran.

The base used in this step can be preferably an inorganic base such as sodium hydride, potassium hydride, sodium carbonate, potassium carbonate, or cesium carbonate; or an organic metal base such as sodium tert-butoxide, potassium tert-butoxide, n-butyllithium, lithium diisopropylamide, lithium hexamethyldisilazide, potassium hexamethyldisilazide, or lithium 2,2,6,6-tetramethylpiperidide. The base is preferably an organic metal base, more preferably lithium diisopropylamide.

The oxidizing agent used in this step is preferably bis(trimethylsilyl) peroxide, 3-phenyl-2-(phenylsulfonyl)oxaziridine (Davis reagent), or (10-camphorsulfonyl)oxaziridine, more preferably (10-camphorsulfonyl)oxaziridine.

The reaction temperature of this step is preferably −100° C. to 100° C., more preferably −78° C. to 30° C.

The reaction time of this step is preferably 1 hour to 10 hours, more preferably 2 hours to 5 hours.

Compound (IIa) has cis-trans isomers. These cis-trans isomers can be separated by a known method such as chromatography. Also, hydroxy groups in cis-trans isomer mixtures of compound (IIa) at an arbitrary ratio are protected, and the mixtures can be stirred in the presence of a base in an inert solvent, followed by the removal of the protective group to obtain mixtures having cis-trans isomers of compound (IIa) at different ratios.

Examples of the hydroxy protective group used in this operation include protective groups that are stable under basic conditions and are removable as described in, for example, P. G. Wuts, T. W. Greene, Greene's Protective Groups in Organic Synthesis. Third Edition, 2006, John Wiley & Sons, Inc. The protective group is preferably a tetrahydropyranyl group.

The base used in this operation can be preferably an inorganic base such as sodium hydride, potassium hydride, sodium carbonate, potassium carbonate, or cesium carbonate; or an organic metal base such as sodium tert-butoxide, potassium tert-butoxide, n-butyllithium, lithium diisopropylamide, lithium hexamethyldisilazide, potassium hexamethyldisilazide, or lithium 2,2,6,6-tetramethylpiperidide. The base is preferably an organic metal base, more preferably lithium diisopropylamide.

The reaction temperature is preferably −78° C. to 100° C., more preferably −58° C. to 10° C.

The reaction time is preferably 1 hour to 10 hours, more preferably 2 hours to 3 hours.

Production Method 3

The intermediate (II) of the compound of the present invention wherein $R^1$ is a hydroxy group can also be produced by the following method:

[Formula 5]

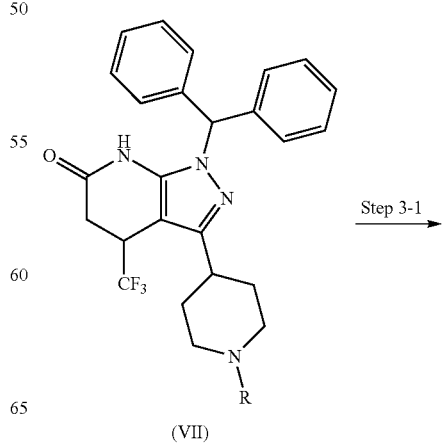

Step 3-1

(VII)

-continued

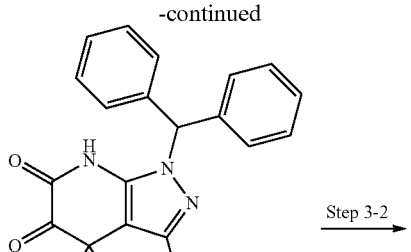

(VIII)

Step 3-2 →

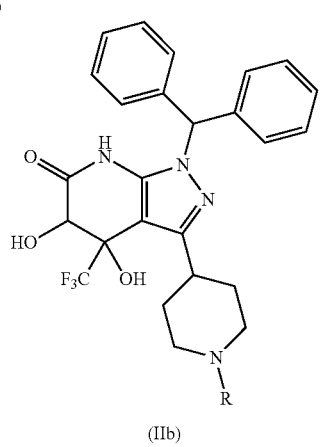

(IIb)

In these formulas, R is as defined above.

(Step 3-1)

This step involves reacting compound (VII) with an oxidizing agent in an inert solvent to produce compound (VIII).

The solvent used in this step can be a halogenated hydrocarbon such as dichloromethane, chloroform, carbon tetrachloride, 1,2-dichloroethane, chlorobenzene, or dichlorobenzene; an ether such as diethyl ether, diisopropyl ether, tetrahydrofuran, dioxane, dimethoxyethane, or tert-butyl methyl ether; or an aromatic hydrocarbon such as benzene, toluene, or xylene. The solvent is preferably a halogenated hydrocarbon, more preferably dichloromethane.

The oxidizing agent used in this step is preferably Dess-Martin reagent.

The reaction temperature of this step is preferably −5° C. to 40° C., more preferably 0° C. to 30° C.

The reaction time of this step is preferably 30 minutes to 3 hours, more preferably 1 hour to 2 hours.

(Step 3-2)

This step involves reacting compound (VIII) with a reducing agent in an inert solvent to produce compound (IIb).

The solvent used in this step can be an alcohol such as methanol, ethanol, n-propanol, isopropanol, n-butanol, isobutanol, tert-butanol, isoamyl alcohol, octanol, cyclohexanol, 2-methoxyethanol, diethylene glycol, or glycerin; an ether such as diethyl ether, diisopropyl ether, tetrahydrofuran, dioxane, dimethoxyethane, or tert-butyl methyl ether; an aromatic hydrocarbon such as benzene, toluene, or xylene; or a mixed solvent thereof. The solvent is preferably an alcohol, more preferably methanol.

The reducing agent used in this step is preferably sodium borohydride.

The reaction temperature of this step is preferably −5° C. to 40° C., more preferably 0° C. to 30° C.

The reaction time of this step is preferably 10 minutes to 3 hours, more preferably 30 minutes to 2 hours.

Production Method 4

The intermediate (II) of the compound of the present invention can also be produced by the following method:

[Formula 6]

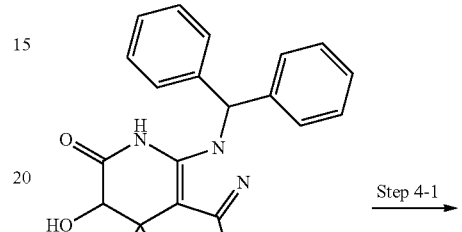

(X)

Step 4-1 →

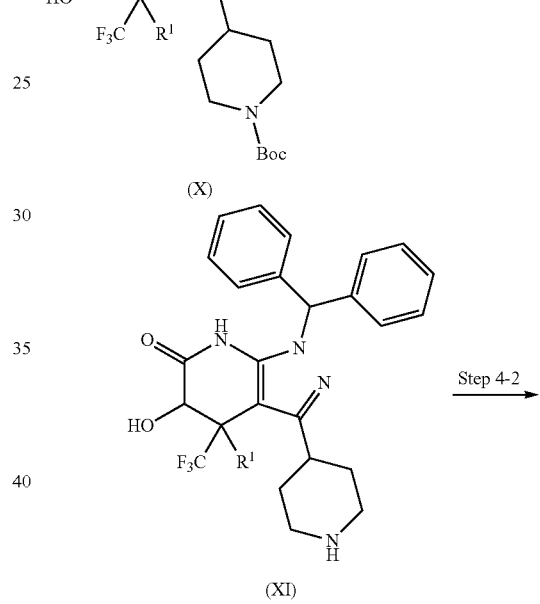

(XI)

Step 4-2 →

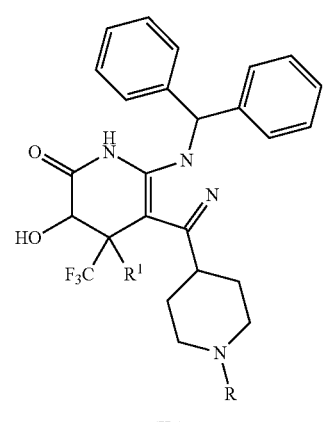

(IIe)

In these formulas, Boc represents a tert-butoxycarbonyl group, and R and $R^1$ are as defined above.

(Step 4-1)

This step involves removing the Boc group from compound (X) to produce compound (XI).

Compound (X) can be produced according to, for example, the methods described in Reference Examples 12, 13, 14, and 16 or Reference Examples 25 and 26.

Examples of a reagent for use in the removal of Boc from the compound (X) include reagents capable of removing Boc as described in, for example, P. G. Wuts, T. W. Greene, Greene's Protective Groups in Organic Synthesis. Third Edition, 2006, John Wiley & Sons, Inc.

The solvent used in this step is preferably an alcohol such as methanol or ethanol; an ether such as tetrahydrofuran or 1,4-dioxane; an alkyl halide such as dichloromethane or chloroform; an ester such as ethyl acetate; an aromatic hydrocarbon such as toluene; a nitrile such as acetonitrile; or a mixed solvent thereof, more preferably an alkyl halide, a nitrile, or a mixed solvent of an alkyl halide and a nitrile, even more preferably a mixed solvent of dichloromethane and acetonitrile.

The reagent used in this step is preferably a combination of chlorotrimethylsilane and sodium iodide.

The reaction temperature of this step is preferably 0° C. to 100° C., more preferably 0° C. to 50° C.

The reaction time of this step is preferably 5 minutes to 24 hours, more preferably 10 minutes to 6 hours.

(Step 4-2)

This step involves reacting compound (IId) with an arylating agent or a heteroarylating agent in the presence of a base in an inert solvent to produce compound (II)

This step can be carried out in the same way as in step 2-1(ii).

Production Method 5

The intermediate (II) of the compound of the present invention wherein $R^1$ is a hydroxy group can also be produced by the following method:

[Formula 7]

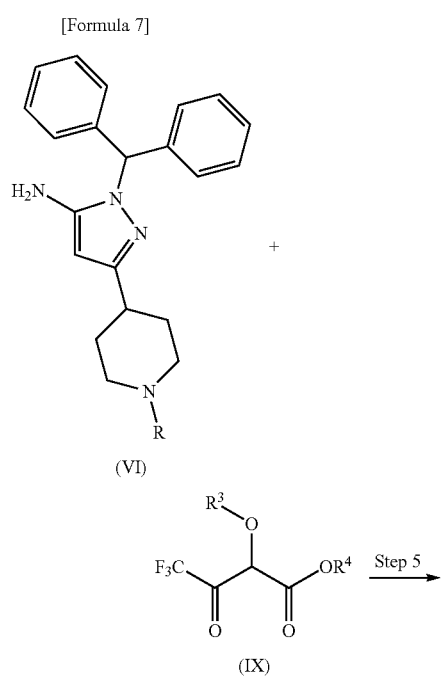

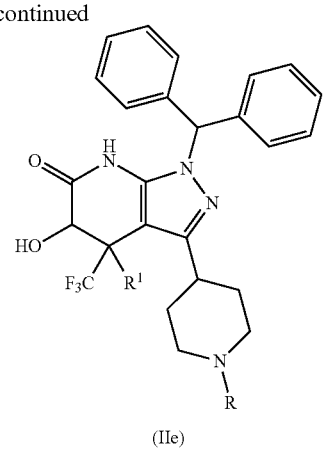

In these formulas, R is as defined above, $R^3$ represents a hydrogen atom, a methyl group, a triethylsilyl group, a tert-butyldimethylsilyl group, or a tert-butyldiphenylsilyl group, and $R^4$ represents a methyl group or an ethyl group.

(Step 5)

This step involves condensing compound (VI) and compound (IX) under heating in a solvent inert to the reaction or in the absence of a solvent to produce compound (IIe).

The solvent used in this step can be an organic acid such as acetic acid, formic acid, oxalic acid, methanesulfonic acid, p-toluenesulfonic acid, camphorsulfonic acid, trifluoroacetic acid, or trifluoromethanesulfonic acid; an ether such as diethyl ether, diisopropyl ether, tetrahydrofuran, dioxane, dimethoxyethane, or tert-butyl methyl ether; an alcohol such as methanol, ethanol, n-propanol, isopropanol, n-butanol, isobutanol, tert-butanol, isoamyl alcohol, octanol, cyclohexanol, 2-methoxyethanol, diethylene glycol, or glycerin; an aromatic hydrocarbon such as benzene, toluene, or xylene; or a mixed solvent thereof. The solvent is preferably a mixed solvent of ethanol and acetic acid.

The reaction temperature of this step is usually 40° C. to 150° C., preferably 50° C. to 130° C., more preferably 60° C. to the reflux temperature of the solvent.

In order to promote the reaction of this step, the reaction solution may be heated and may also be irradiated with microwaves.

The reaction time of this step is usually 5 minutes to 72 hours, preferably 15 minutes to 24 hours, more preferably 30 minutes to 3 hours.

When $R^3$ in compound (IX) is a methyl group, a triethylsilyl group, a tert-butyldimethylsilyl group, or a tert-butyldiphenylsilyl group, the hydroxy protective group can be removed from the compound produced by the above-mentioned reaction by a method described in, for example, P. G. Wuts, T. W. Greene, Greene's Protective Groups in Organic Synthesis. Third Edition, 2006, John Wiley & Sons, Inc. to produce compound (IIe).

If necessary, the product of each step mentioned above can be isolated as the free compound or a salt thereof from the reaction mixture after the completion of the reaction by a routine method, for example, (1) a method of directly concentrating the reaction solution, (2) a method of filtering off insoluble matter such as a catalyst and concentrating the filtrate, (3) a method of adding water and a solvent immiscible with water (e.g., dichloroethane, diethyl ether, ethyl acetate, or toluene) to the reaction solution to extract a product, or (4) a method of collecting a crystallized or precipitated product by filtration. The isolated product can be purified, if necessary, by a routine method, for example, recrystallization, reprecipitation, or various chromatography techniques. Alternatively, the product of each step may be used in the subsequent step without being isolated or purified.

The compound (I) of the present invention is isolated and purified as the free compound or a pharmacologically acceptable salt, a hydrate, or a solvate thereof. A pharmacologically acceptable salt of the compound (I) of the present invention can be produced through a salt-forming reaction of the compound (I) by a routine method. The isolation and purification are carried out by application of usual chemical operations such as extraction, concentration, distillation, crystallization, filtration, recrystallization, or various chromatography techniques.

Various isomers can be separated by exploiting differences in physicochemical properties between the isomers. For example, a racemic mixture can be converted to an optically pure isomer by, for example, fractionated crystallization for producing a diastereomer salt with an optically active base or acid or chromatography using a chiral column. Also, a diastereomeric mixture can be separated by, for example, fractionated crystallization or various chromatography techniques. Alternatively, an optically active compound can also be produced using an appropriate optically active starting material.

Examples of dosage forms of the compound represented by the general formula (I) of the present invention or a pharmacologically acceptable salt thereof can include: oral administration forms such as tablets, granules, powders, capsules, and syrups; and parenteral administration forms such as injections and suppositories. These formulations can be administered systemically or locally.

Examples of forms of oral medicaments comprising the compound represented by the general formula (I) of the present invention or a pharmacologically acceptable salt thereof include tablets, pills, granules, powders, capsules, solutions, suspension, emulsions, syrups, and elixirs. Examples of forms of parenteral medicaments comprising the compound represented by the general formula (I) of the present invention or a pharmacologically acceptable salt thereof include injections, ointments, gels, creams, patches, aerosols, inhalants, sprays, eye drops, and suppositories. The medicaments in these forms can be prepared according to a routine method using additives appropriately selected according to need from pharmaceutically acceptable additives such as excipients, binders, diluents, stabilizers, antiseptics, colorants, solubilizers, suspending agents, buffers, and wetting agents.

The dose at which the compound represented by the general formula (I) of the present invention or a pharmacologically acceptable salt thereof is administered differs depending on the symptoms, body weight, and age of the recipient (a warm-blooded animal, for example, a human), the administration method, etc. For example, in the case of oral administration, a single dose is 0.01 mg/kg body weight (preferably 0.03 mg/kg body weight) as the lower limit and 300 mg/kg body weight (preferably 100 mg/kg body weight) as the upper limit and is desirably administered one to several times a day according to the symptoms. In the case of intravenous administration, a single dose is 0.01 mg/kg body weight (preferably 0.03 mg/kg body weight) as the lower limit and 300 mg/kg body weight (preferably 100 mg/kg body weight) as the upper limit and is desirably administered one to several times a day according to the symptoms.

Hereinafter, the present invention will be described in more detail with reference to Examples, Test Examples, and Formulation Examples. However, the scope of the present invention is not intended to be limited by these. In the Examples given below, hexane represents n-hexane; THF represents tetrahydrofuran; IPA represents 2-propanol; DMF represents N,N'-dimethylformamide; DMSO represents dimethyl sulfoxide; and CSA represents (±)-10-camphorsulfonic acid.

EXAMPLES (Reference Example 1) 1-(Diphenylmethyl)-3-{1-[5-(trifluoromethyl)pyridin-2-yl]piperidin-4-yl}-1H-pyrazol-5-amine

[Formula 8]

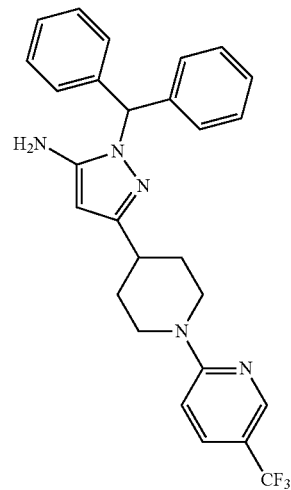

n-Butyllithium (2.69 M solution in hexane, 17.5 mL, 47.1 mmol) was added dropwise at −78° C. to a solution of anhydrous acetonitrile (2.47 mL, 47.1 mmol) in anhydrous THF (70 mL), and the mixture was stirred at the same temperature as above for 10 minutes. A solution of ethyl 1-[5-(trifluoromethyl)pyridin-2-yl]piperidine-4-carboxylate (compound described in the pamphlet of WO2005/40119, 5.69 g, 18.8 mmol) in THF (30 mL) was added dropwise thereto at the same temperature as above, and the mixture was stirred for 30 minutes. Then, acetic acid (6 mL) was added thereto, and the temperature of the mixture was raised to room temperature. To the reaction solution, ethyl acetate and Celite® were added, and the mixture was stirred for approximately 10 minutes and filtered through Celite. The solvent in the filtrate was distilled off under reduced pressure. The obtained residue was purified by silica gel column chromatography [elute: hexane/ethyl acetate=90/10-50/50 (gradient)] to obtain a nitrile intermediate.

Diphenylmethyl hydrazine hydrochloride (4.64 g, 19.8 mmol) was added to a solution of the nitrile intermediate obtained by the procedures described above in ethanol (100 mL), and the mixture was stirred at 50° C. for 2 hours. The reaction solution was concentrated under reduced pressure, and the obtained residue was separated into organic and aqueous layers by the addition of a saturated sodium bicarbonate aqueous solution and ethyl acetate. The organic layer was washed with brine and dried over anhydrous sodium sulfate, and the solvent was distilled off under reduced pressure. The obtained residue was purified by silica gel column chromatography [elute: hexane/ethyl acetate=90/10-50/50 (gradient)] to obtain the title compound (5.44 g, yield: 61%).

$^1$H-NMR (400 Hz, CDCl$_3$) δ: 8.38 (1H, s), 7.59 (1H, dd, J=9 Hz, 2 Hz), 7.38-7.27 (6H, m), 7.25-7.18 (4H, m), 6.66 (1H, s), 6.64 (1H, s), 5.41 (1H, s), 4.41 (2H, d, J=13 Hz), 3.23 (2H, s), 3.05-2.98 (2H, m), 2.88-2.81 (1H, m), 2.01 (2H, dd, J=13 Hz, 3 Hz), 1.66 (2H, ddd, J=25 Hz, 13 Hz, 4 Hz).

(Reference Example 2) 1-(Diphenylmethyl)-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one

[Formula 9]

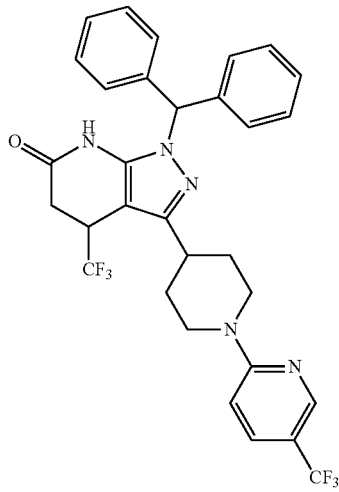

Trifluoroacetaldehyde ethyl hemiacetal (2.68 g, 18.6 mmol) was added to a solution of 1-(diphenylmethyl)-3-{1-[5-(trifluoromethyl)pyridin-2-yl]piperidin-4-yl}-1H-pyrazol-5-amine (4.50 g, 9.42 mmol) produced in Reference Example 1 and Meldrum's acid (2.65 g, 18.4 mmol) in ethanol (40 mL), and the mixture was stirred for 5 hours under heating to reflux. The solvent in the reaction solution was distilled off under reduced pressure. The obtained residue was purified three times by silica gel column chromatography [NH-silica gel, elute:

(i) hexane/dichloromethane=50/50-0/100 (gradient), (ii) dichloromethane/methanol=100/0-90/10 (gradient)] to obtain the title compound (2.85 g, yield: 50%).

$^1$H-NMR (400 Hz, DMSO-d$_6$) δ: 11.18 (1H, s), 8.38 (1H, s), 7.75 (1H, dd, J=9 Hz, 2 Hz), 7.36-7.16 (10H, m), 6.96 (1H, d, J=9 Hz), 6.81 (1H, s), 4.49-4.41 (2H, m), 4.10-4.00 (1H, m), 3.16-2.89 (5H, m), 1.95-1.46 (4H, m).

(Reference Example 3) trans-1-(Diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one

[Formula 10]

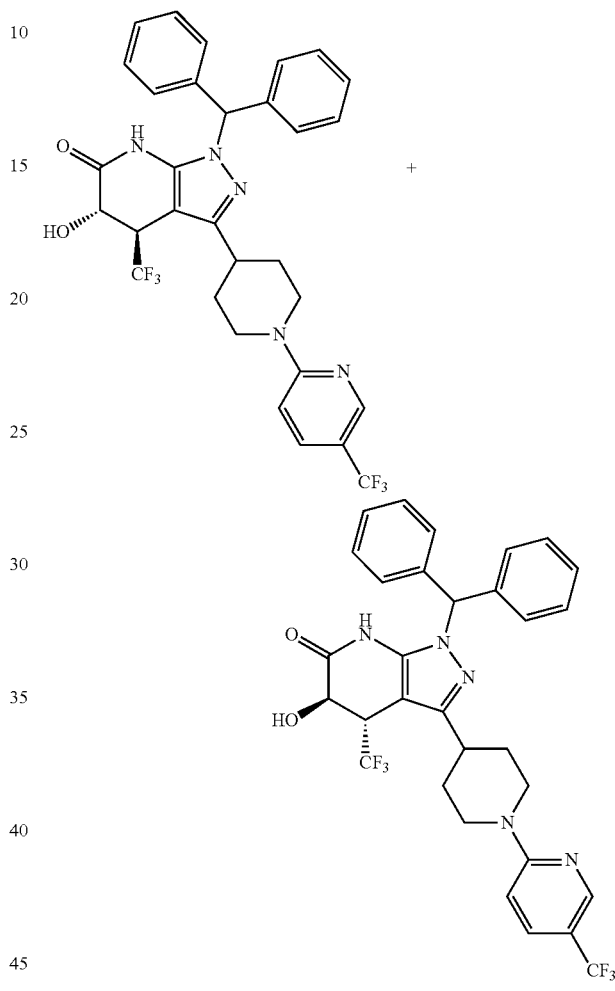

n-Butyllithium (2.6 M solution in hexane, 1.75 mL, 4.70 mmol) was added at −78° C. to a solution of diisopropylamine (0.65 mL, 4.6 mmol) in anhydrous THF (12 mL), and the mixture was stirred at the same temperature as above for 15 minutes. Then, a solution of 1-(diphenylmethyl)-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one (980 mg, 1.63 mmol) produced in Reference Example 2 in anhydrous THF (10 mL) was added thereto, and the mixture was stirred for 30 minutes. To the reaction solution, a solution of (1S)-(+)-(10-camphorsulfonyl)oxaziridine (302 mg, 1.32 mmol) and (1R)-(−)-(10-camphorsulfonyl)oxaziridine (302 mg, 1.32 mmol) in anhydrous THF (8 mL) was added at the same temperature as above, and the mixture was heated to room temperature and stirred for 3 hours. To the reaction solution, a saturated ammonium chloride aqueous solution was added, followed by extraction with ethyl acetate three times. The organic layer was washed with brine and dried over anhydrous magnesium sulfate, and the solvent was distilled off under reduced pressure. The obtained residue was purified by silica gel column chromatography [elute: hexane/ethyl acetate=80/20-50/50]. The obtained partially purified product was purified with a dichloromethane-methanol mixed solvent to obtain the title compound (611 mg, yield: 61%).

$^1$H-NMR (400 Hz, DMSO-$d_6$) δ: 11.26 (1H, s), 8.38 (1H, s), 7.74 (1H, dd, J=9 Hz, 3 Hz), 7.36-7.15 (10H, m), 6.96 (1H, d, J=9 Hz), 6.81 (1H, s), 6.68 (1H, d, J=5 Hz), 4.50-4.39 (2H, m), 4.20 (1H, d, J=5 Hz), 3.99-3.89 (1H, m), 3.11-2.89 (3H, m), 1.92-1.77 (2H, m), 1.71-1.47 (2H, m).

(Reference Example 4) cis-1-(Diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one

[Formula 11]

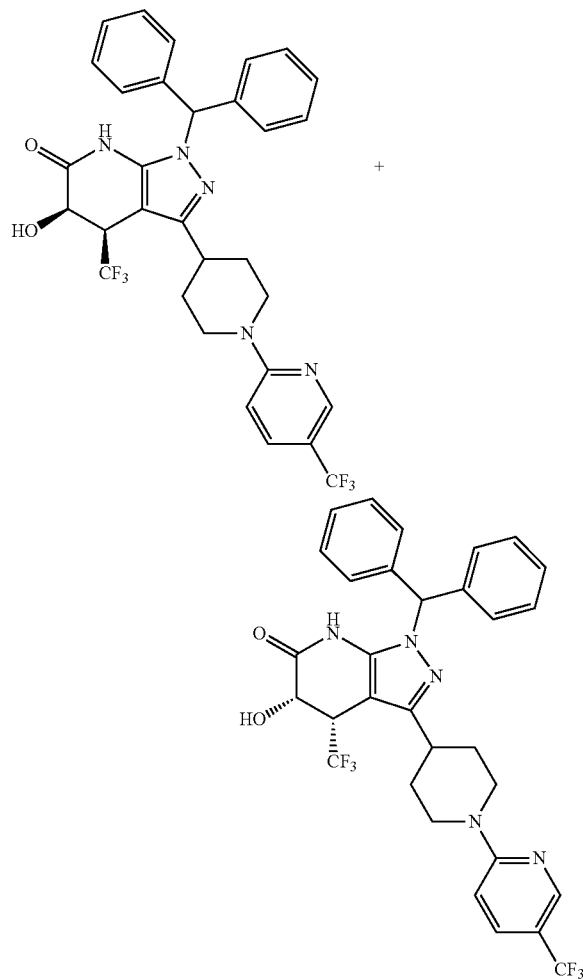

3,4-Dihydro-2H-pyran (0.25 mL, 2.7 mmol) was added to a solution of trans-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one (730 mg, 1.19 mmol) produced in Reference Example 3 and CSA (30 mg, 0.129 mmol) in dichloromethane (10 mL), and the mixture was stirred for 8 hours under heating to reflux. To the reaction solution, triethylamine was added, and the solvent was distilled off under reduced pressure. The obtained residue was purified by silica gel column chromatography [elute: hexane/ethyl acetate=80/20-60/40 (gradient)] to obtain a protected alcohol intermediate.

Lithium diisopropylamide (1.09 M solution in hexane and THF, 3.50 mL, 3.81 mmol) was added at 0° C. to a solution of the protected alcohol intermediate obtained by the procedures described above in anhydrous THF (20 mL), and the mixture was stirred at the same temperature as above for 2 hours. Methanol (1 mL) was added thereto at −40° C., and then, the temperature of the mixture was raised to room temperature. A saturated ammonium chloride aqueous solution was added thereto, followed by extraction with ethyl acetate three times. The organic layer was washed with brine and dried over anhydrous magnesium sulfate, and the solvent was distilled off under reduced pressure. The obtained residue was purified by silica gel column chromatography [elute: hexane/ethyl acetate=100/0-75/25 (gradient)] to obtain a synthesis intermediate.

CSA (60 mg, 0.258 mmol) was added to a solution of the synthesis intermediate obtained by the procedures described above in methanol (5 mL), and the mixture was stirred at room temperature for 1 hour and further at 50° C. for 30 minutes. To the reaction solution, triethylamine (0.2 mL) was added, and the solvent was distilled off under reduced pressure. The obtained residue was purified by silica gel column chromatography [elute: hexane/ethyl acetate=80/20-50/50 (gradient)] to obtain the title compound (95 mg, yield: 13%).

$^1$H-NMR (400 MHz, DMSO-$d_6$) δ: 11.21 (1H, s), 8.38 (1H, s), 7.75 (1H, d, J=9 Hz), 7.36-7.23 (8H, m), 7.15 (1H, s), 7.14 (1H, s), 6.96 (1H, d, J=9 Hz), 6.74 (1H, s), 5.80 (1H, d, J=4 Hz), 4.60-4.55 (1H, m), 4.49-4.39 (2H, m), 4.20-4.10 (1H, m), 3.11-2.88 (3H, m), 1.97-1.45 (4H, m).

(Reference Example 5) 1-(Diphenylmethyl)-4-hydroxy-4-(trifluoromethyl)-3-{1-[5-(trifluoromethyl)pyridin-2-yl]piperidin-4-yl}-4,7-dihydro-1H-pyrazolo[3,4-b]pyridine-5,6-dione

[Formula 12]

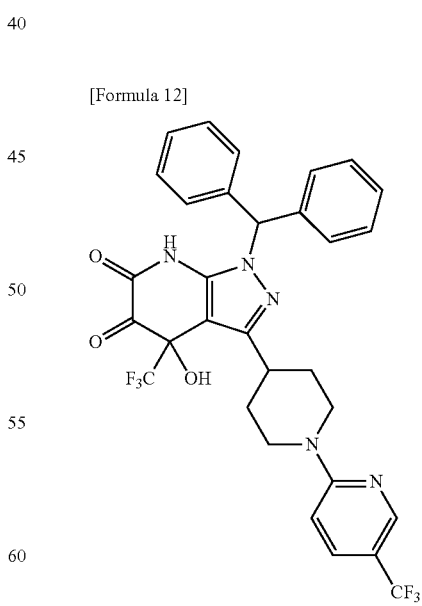

Dess-Martin reagent (210 mg, 0.495 mmol) was added to a solution of trans-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one (200 mg, 0.325 mmol) produced in Reference Example 3 in dichloromethane (5 mL), and the mixture was stirred at room temperature for 1 hour. Dess-Martin reagent (100 mg, 0.236 mmol) was further added thereto, and the mixture was stirred for 15 minutes. Dess-Martin reagent (100 mg, 0.236 mmol) was further added thereto, and the mixture was stirred for 15 minutes. To the reaction solution, a saturated sodium bicarbonate aqueous solution was added, followed by extraction with ethyl acetate three times. The organic layer was washed with brine and dried over anhydrous magnesium sulfate, and the solvent was distilled off under reduced pressure. The obtained residue was purified by silica gel column chromatography [elute: hexane/ethyl acetate=80/20-60/40 (gradient)] to obtain the title compound (41 mg, yield: 20%).

MS (ESI) m/z: 629 (M+H)$^+$.

(Reference Example 6) 1-(Diphenylmethyl)-4,5-dihydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one

[Formula 13]

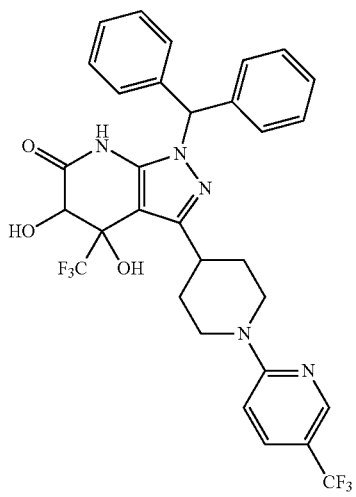

Sodium borohydride (10 mg, 0.264 mmol) was added to a solution of 1-(diphenylmethyl)-4-hydroxy-4-(trifluoromethyl)-3-{1-[5-(trifluoromethyl)pyridin-2-yl]piperidin-4-yl}-4,7-dihydro-1H-pyrazolo[3,4-b]pyridine-5,6-dione (41 mg, 0.0651 mmol) produced in Reference Example 5 in methanol (2.0 mL), and the mixture was stirred for 1 hour. To the reaction solution, a saturated ammonium chloride aqueous solution was added, followed by extraction with ethyl acetate three times. The organic layer was washed with brine and dried over anhydrous magnesium sulfate, and the solvent was distilled off under reduced pressure. The obtained residue was purified by silica gel column chromatography [elute: hexane/ethyl acetate=70/30-60/40 (gradient)] to obtain the title compound (31 mg, yield: 75%).

$^1$H-NMR (400 Hz, DMSO-d$_6$) δ: 11.23 (1H, s), 8.37 (1H, s), 7.73 (1H, d, J=9 Hz), 7.36-7.22 (8H, m), 7.16 (2H, d, J=8 Hz), 6.95 (1H, d, J=9 Hz), 6.84 (1H, s), 6.75 (1H, s), 5.97 (1H, d, J=4 Hz), 4.54-4.38 (3H, m), 3.19 (1H, t, J=11 Hz), 3.04-2.92 (2H, m), 2.00 (1H, d, J=12 Hz), 1.79-1.47 (3H, m).

(Reference Example 7) Ethyl 1-(5-isopropoxypyridin-2-yl)piperidine-4-carboxylate

[Formula 14]

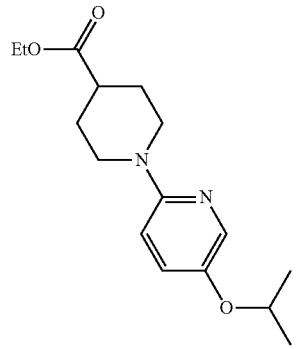

Sodium tert-butoxide (0.56 g, 5.79 mmol), tris(dibenzylideneacetone)dipalladium(0) (0.106 g, 0.116 mmol), and rac-2,2'-bis(diphenylphosphino)1,1'-binaphthyl (0.216 g, 0.347 mmol) were added to a solution of 2-bromo-5-isopropoxypyridine (compound described in the pamphlet of WO2009/81789, 1.00 g, 4.63 mmol) and ethyl piperidine-4-carboxylate (2.14 mL, 13.9 mmol) in toluene (22 mL), and the mixture was stirred at 120° C. for 1.5 hours. The reaction solution was cooled to room temperature, and water was added thereto, followed by extraction with ethyl acetate. The obtained organic layer was washed with brine and dried over anhydrous sodium sulfate, and the solvent was distilled off under reduced pressure. The obtained residue was purified by silica gel column chromatography [elute: hexane/ethyl acetate=100/0-90/10 (gradient)] to obtain the title compound (803 mg, yield: 59%).

$^1$H-NMR (400 MHz, CDCl$_3$) δ: 7.91 (1H, d, J=3 Hz), 7.18-7.13 (1H, m), 6.66 (1H, d, J=9 Hz), 4.41-4.33 (1H, m), 4.15 (2H, q, J=7 Hz), 4.10-4.05 (2H, m), 2.95-2.86 (2H, m), 2.52-2.45 (1H, m), 2.04-1.98 (2H, m), 1.85-1.75 (2H, m), 1.30 (6H, d, J=6 Hz), 1.26 (3H, t, J=7 Hz).

(Reference Example 8) 1-(Diphenylmethyl)-3-[1-(5-isopropoxypyridin-2-yl)piperidin-4-yl]-1H-pyrazol-5-amine

[Formula 15]

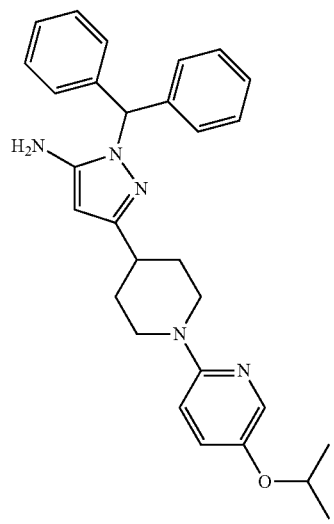

The title compound (1.65 g, yield: 48%) was obtained through the same reaction as in the method described in Reference Example 1 using ethyl 1-(5-isopropoxypyridin-2-yl)piperidine-4-carboxylate (2.14 g, 7.32 mmol) produced in Reference Example 7 instead of ethyl 1-[5-(trifluoromethyl)pyridin-2-yl]piperidine-4-carboxylate.

$^1$H-NMR (400 MHz, CDCl$_3$) δ: 7.92 (1H, d, J=3 Hz), 7.38-7.27 (6H, m), 7.24-7.18 (4H, m), 7.13 (1H, dd, J=9 Hz, 3 Hz), 6.68 (1H, s), 6.66 (1H, d, J=9 Hz), 5.43 (1H, s), 4.41-4.31 (1H, m), 4.19-4.11 (2H, m), 3.27-3.16 (2H, m), 2.89-2.69 (3H, m), 2.05-1.97 (2H, m), 1.79-1.66 (2H, m), 1.30 (6H, d, J=6 Hz).

(Reference Example 9) 1-(Diphenylmethyl)-3-[1-(5-isopropoxypyridin-2-yl)piperidin-4-yl]-4-(trifluoromethyl)-1,4,5,7-tetrahydro-6H-pyrazolo[3,4-b]pyridin-6-one

[Formula 16]

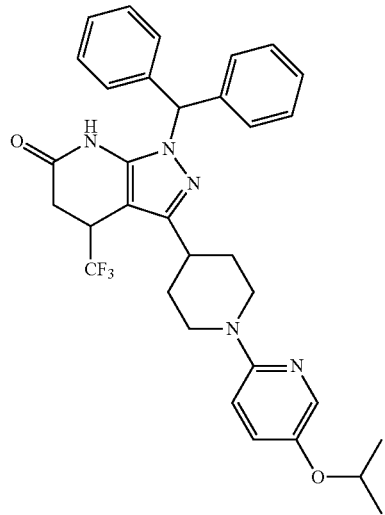

The title compound (1.50 g, yield: 72%) was obtained through the same reaction as in the method described in Reference Example 2 using 1-(diphenylmethyl)-3-[1-(5-isopropoxypyridin-2-yl)piperidin-4-yl]-1H-pyrazol-5-amine (1.65 g, 3.53 mmol) produced in Reference Example 8 instead of 1-(diphenylmethyl)-3-{1-[5-(trifluoromethyl)pyridin-2-yl]piperidin-4-yl}-1H-pyrazol-5-amine.

$^1$H-NMR (400 MHz, DMSO-d$_6$) δ: 11.17 (1H, s), 7.82 (1H, d, J=3 Hz), 7.37-7.17 (11H, m), 6.82-6.76 (2H, m), 4.47-4.37 (1H, m), 4.21-4.11 (2H, m), 4.09-3.98 (1H, m), 3.11 (1H, dd, J=17 Hz, 8 Hz), 2.85-2.70 (4H, m), 1.95-1.53 (4H, m), 1.22 (6H, d, J=6 Hz).

(Reference Example 10) trans-1-(Diphenylmethyl)-5-hydroxy-3-[1-(5-isopropoxypyridin-2-yl)piperidin-4-yl]-4-(trifluoromethyl)-1,4,5,7-tetrahydro-6H-pyrazolo[3,4-b]pyridin-6-one

[Formula 17]

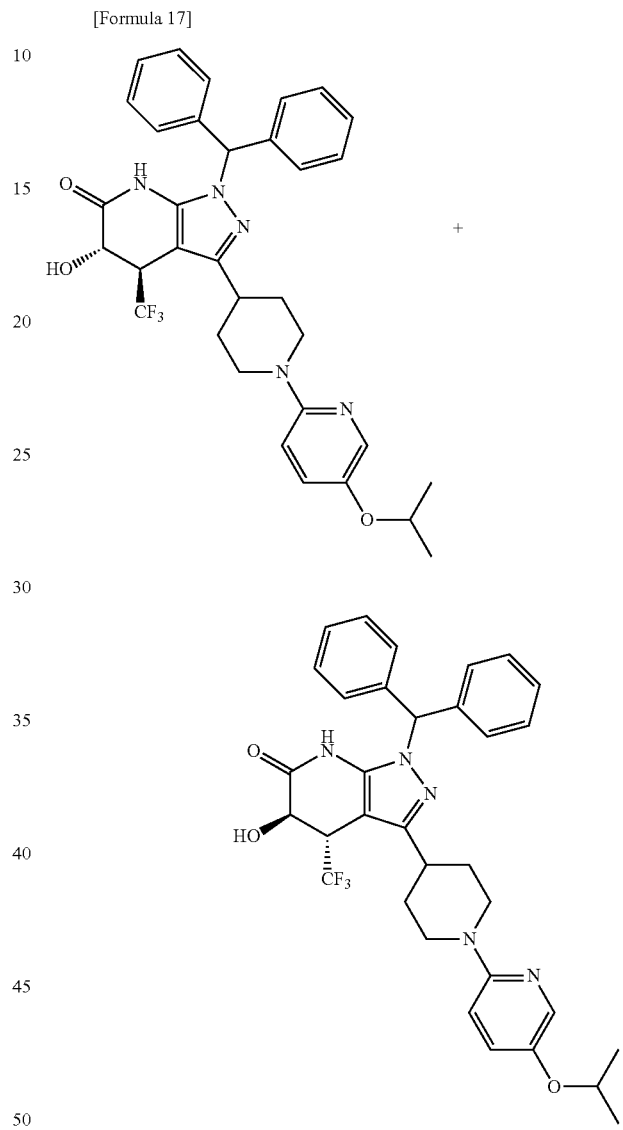

The title compound (1.10 g, yield: 71%) was obtained through the same reaction as in Reference Example 3 using 1-(diphenylmethyl)-3-[1-(5-isopropoxypyridin-2-yl)piperidin-4-yl]-4-(trifluoromethyl)-1,4,5,7-tetrahydro-6H-pyrazolo[3,4-b]pyridin-6-one (1.50 g, 2.54 mmol) produced in Reference Example 9 instead of trans-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-d$_6$) δ: 11.25 (1H, s), 7.82 (1H, d, J=3 Hz), 7.37-7.18 (11H, m), 6.81 (1H, s), 6.79 (1H, d, J=9 Hz), 6.67 (1H, d, J=5 Hz), 4.47-4.37 (1H, m), 4.22-4.10 (3H, m), 3.97-3.87 (1H, m), 2.86-2.72 (3H, m), 1.90-1.52 (4H, m), 1.22 (6H, d, J=6 Hz).

31

(Reference Example 11) cis-1-(Diphenylmethyl)-5-hydroxy-3-[1-(5-isopropoxypyridin-2-yl)piperidin-4-yl]-4-(trifluoromethyl)-1,4,5,7-tetrahydro-6H-pyrazolo[3,4-b]pyridin-6-one

[Formula 18]

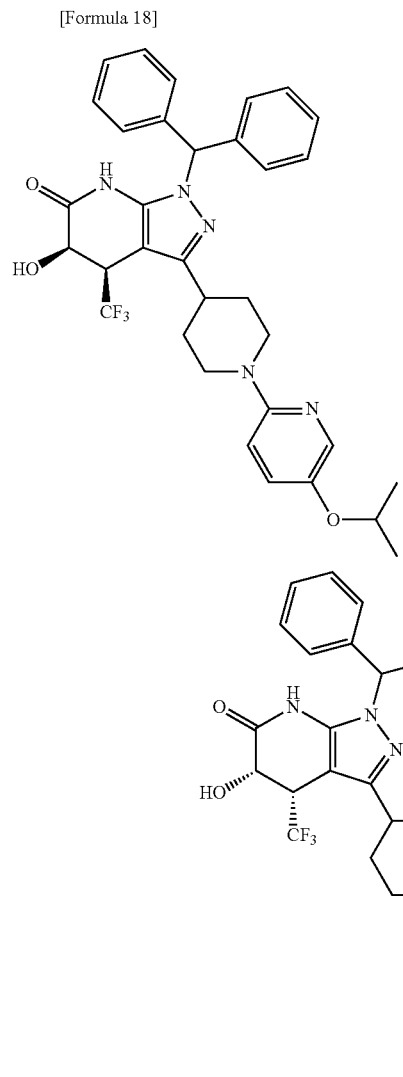

The title compound (66 mg, yield: 15%) was obtained through the same reaction as in the method described in Reference Example 4 using trans-1-(diphenylmethyl)-5-hydroxy-3-[1-(5-isopropoxypyridin-2-yl)piperidin-4-yl]-4-(trifluoromethyl)-1,4,5,7-tetrahydro-6H-pyrazolo[3,4-b]pyridin-6-one (0.78 g, 1.3 mmol) produced in Reference Example 10 instead of trans-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-$d_6$) δ: 11.20 (1H, s), 7.82 (1H, d, J=3 Hz), 7.37-7.19 (9H, m), 7.19-7.14 (2H, m), 6.79 (1H, d, J=9 Hz), 6.74 (1H, s), 5.78 (1H, d, J=4 Hz), 4.60-4.53 (1H, m), 4.47-4.36 (1H, m), 4.22-4.08 (3H, m), 2.86-2.72 (3H, m), 1.95-1.83 (1H, m), 1.80-1.52 (3H, m), 1.22 (6H, d, J=6 Hz).

32

(Reference Example 12) tert-Butyl 4-[5-amino-1-(diphenylmethyl)-1H-pyrazol-3-yl]piperidine-1-carboxylate

[Formula 19]

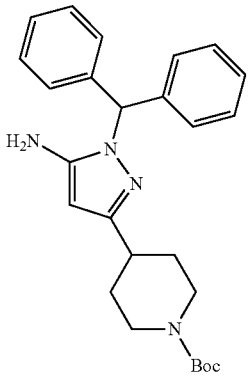

Diphenylmethyl hydrazine hydrochloride (8.57 g, 36.5 mmol) was added to a solution of tert-butyl 4-(cyanoacetyl)piperidine-1-carboxylate (compound described in the pamphlet of WO2004/14910, 7.1 g, 28 mmol) in ethanol (71 mL), and the mixture was stirred at 50° C. for 1 hour. The reaction solution was concentrated under reduced pressure, and the obtained residue was separated into organic and aqueous layers by the addition of a saturated sodium bicarbonate aqueous solution and ethyl acetate. The organic layer was dried over anhydrous magnesium sulfate, and the solvent was distilled off under reduced pressure. The obtained residue was purified by silica gel column chromatography [elute: hexane/ethyl acetate=95/5-40/60 (gradient)] to obtain the title compound (7.43 g, yield: 59%).

$^1$H-NMR (400 Hz, CDCl$_3$) δ: 7.37-7.19 (10H, m), 6.66 (1H, s), 5.40 (1H, s), 4.11 (1H, brs), 3.23-3.20 (1H, m), 2.82-2.65 (3H, m), 1.89-1.86 (2H, m), 1.61-1.52 (4H, m), 1.46 (9H, s).

(Reference Example 13) tert-Butyl 4-[1-(diphenylmethyl)-6-oxo-4-(trifluoromethyl)-4,5,6,7-tetrahydro-1H-pyrazolo[3,4-b]pyridin-3-yl]piperidine-1-carboxylate

[Formula 20]

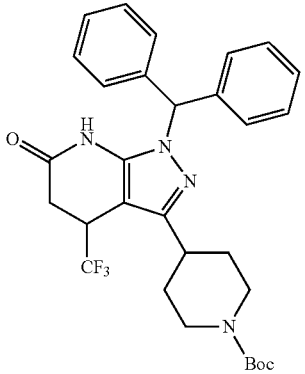

The title compound (1.48 g, yield: 46%) was obtained through the same reaction as in Reference Example 2 using tert-butyl 4-[5-amino-1-(diphenylmethyl)-1H-pyrazol-3-yl]piperidine-1-carboxylate (2.50 g, 5.78 mmol) produced in Reference Example 12 instead of 1-(diphenylmethyl)-3-{1-[5-(trifluoromethyl)pyridin-2-yl]piperidin-4-yl}-1H-pyrazol-5-amine.

$^1$H-NMR (400 Hz, CDCl$_3$) δ: 7.44-7.12 (10H, m), 6.69 (1H, s), 4.13 (1H, brs), 3.65-3.55 (1H, m), 2.95-2.69 (7H, m), 1.87-1.55 (4H, m), 1.45 (9H, s).

(Reference Example 14) tert-Butyl 4-[trans-1-(diphenylmethyl)-5-hydroxy-6-oxo-4-(trifluoromethyl)-4,5,6,7-tetrahydro-1H-pyrazolo[3,4-b]pyridin-3-yl]piperidine-1-carboxylate

[Formula 21]

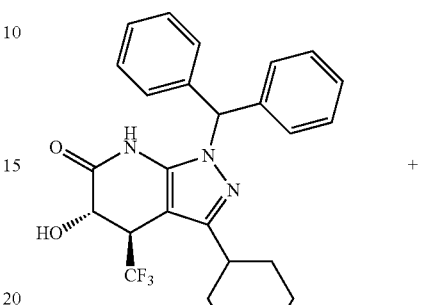

The title compound (450 mg, yield: 35%) was obtained through the same reaction as in Reference Example 3 using tert-butyl 4-[1-(diphenylmethyl)-6-oxo-4-(trifluoromethyl)-4,5,6,7-tetrahydro-1H-pyrazolo[3,4-b]pyridin-3-yl]piperidine-1-carboxylate (1.24 g, 2.24 mmol) produced in Reference Example 13 instead of trans-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 Hz, DMSO-d$_6$) δ: 11.25 (1H, s), 7.37-7.19 (10H, m), 6.82 (1H, s), 6.66 (1H, d, J=5 Hz), 4.19 (1H, d, J=5 Hz), 3.99-3.87 (2H, m), 2.91-2.75 (3H, m), 1.78-1.40 (4H, m), 1.40 (9H, s).

(Reference Example 15) trans-1-(Diphenylmethyl)-5-hydroxy-4-(trifluoromethyl)-3-{1-[6-(trifluoromethyl)pyridazin-3-yl]piperidin-4-yl}-1,4,5,7-tetrahydro-6H-pyrazolo[3,4-b]pyridin-6-one

[Formula 22]

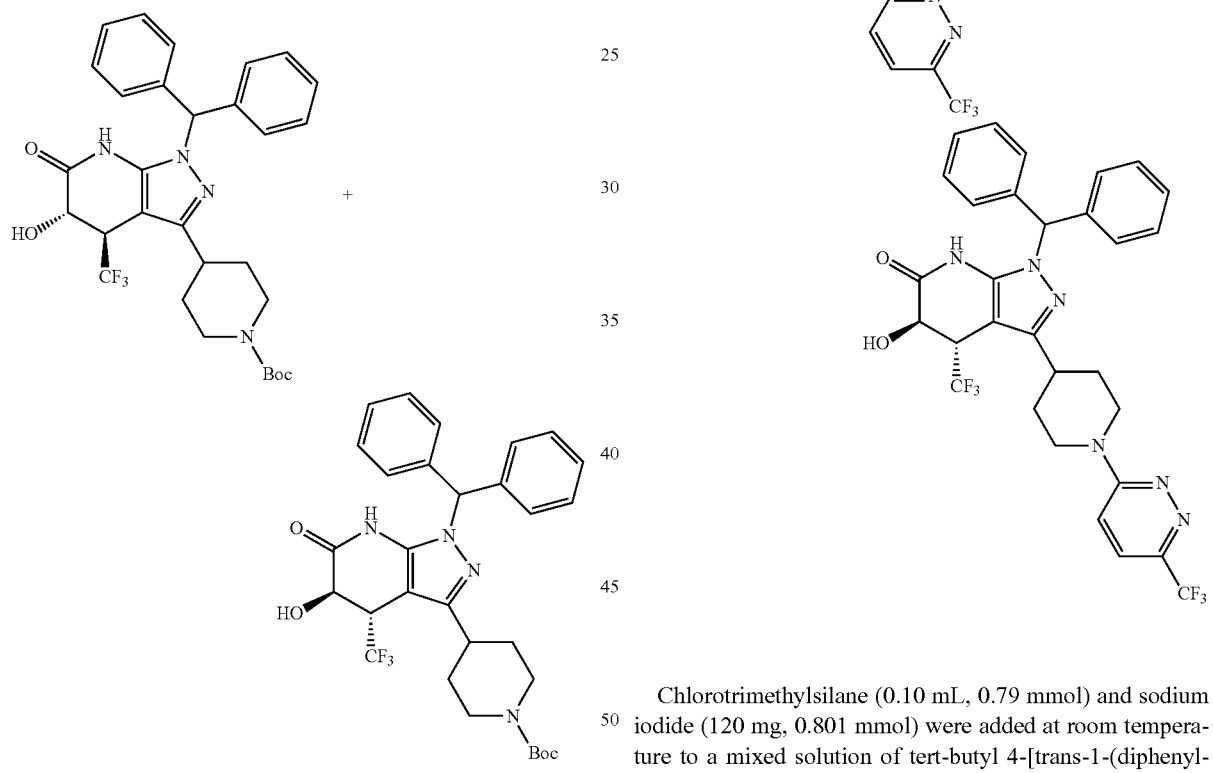

Chlorotrimethylsilane (0.10 mL, 0.79 mmol) and sodium iodide (120 mg, 0.801 mmol) were added at room temperature to a mixed solution of tert-butyl 4-[trans-1-(diphenylmethyl)-5-hydroxy-6-oxo-4-(trifluoromethyl)-4,5,6,7-tetrahydro-1H-pyrazolo[3,4-b]pyridin-3-yl]piperidine-1-carboxylate (180 mg, 0.79 mmol) produced in Reference Example 14 in dichloromethane (2 mL) and acetonitrile (2 mL), and the mixture was stirred for 2 hours. The solvent in the reaction solution was distilled off under reduced pressure to obtain a synthesis intermediate.

3-Chloro-6-(trifluoromethyl)pyridazine (130 mg, 0.712 mmol) and N,N-diisopropylethylamine (0.20 mL, 1.2 mmol) were added to a solution of the synthesis intermediate obtained by the procedures described above in DMSO (5 mL), and the mixture was stirred at room temperature for 2 days and half a day. To the reaction solution, water was added, followed by extraction with ethyl acetate three times.

The organic layer was washed with brine and dried over anhydrous magnesium sulfate, and the solvent was distilled off under reduced pressure. The obtained residue was purified by silica gel column chromatography [elute: hexane/ethyl acetate=90/10-50/50] to obtain the title compound (123 mg, yield: 63%).

$^1$H-NMR (400 Hz, DMSO-$d_6$) δ: 11.27 (1H, s), 7.75 (1H, d, J=10 Hz), 7.41 (1H, d, J=10 Hz), 7.35-7.17 (10H, m), 6.82 (1H, s), 6.69 (1H, d, J=5 Hz), 4.55-4.50 (2H, m), 4.21-4.20 (1H, m), 4.00-3.93 (1H, m), 3.19-2.97 (3H, m), 1.96-1.53 (4H, m).

(Reference Example 16) tert-Butyl 4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidine-1-carboxylate

[Formula 23]

(Reference Example 17) cis-1-(Diphenylmethyl)-5-hydroxy-4-(trifluoromethyl)-3-{1-[6-(trifluoromethyl)pyridazin-3-yl]piperidin-4-yl}-1,4,5,7-tetrahydro-6H-pyrazolo[3,4-b]pyridin-6-one

[Formula 24]

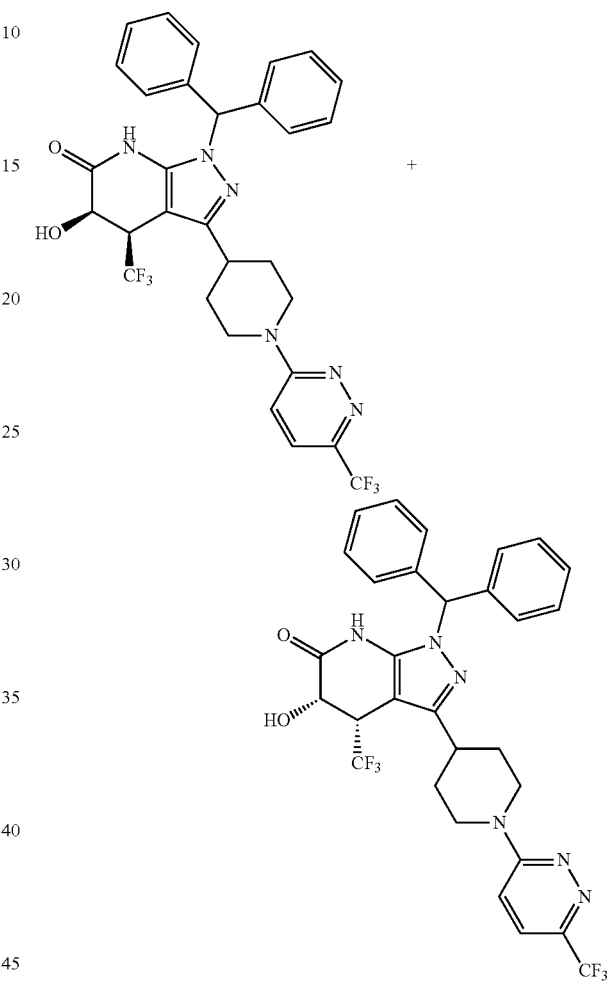

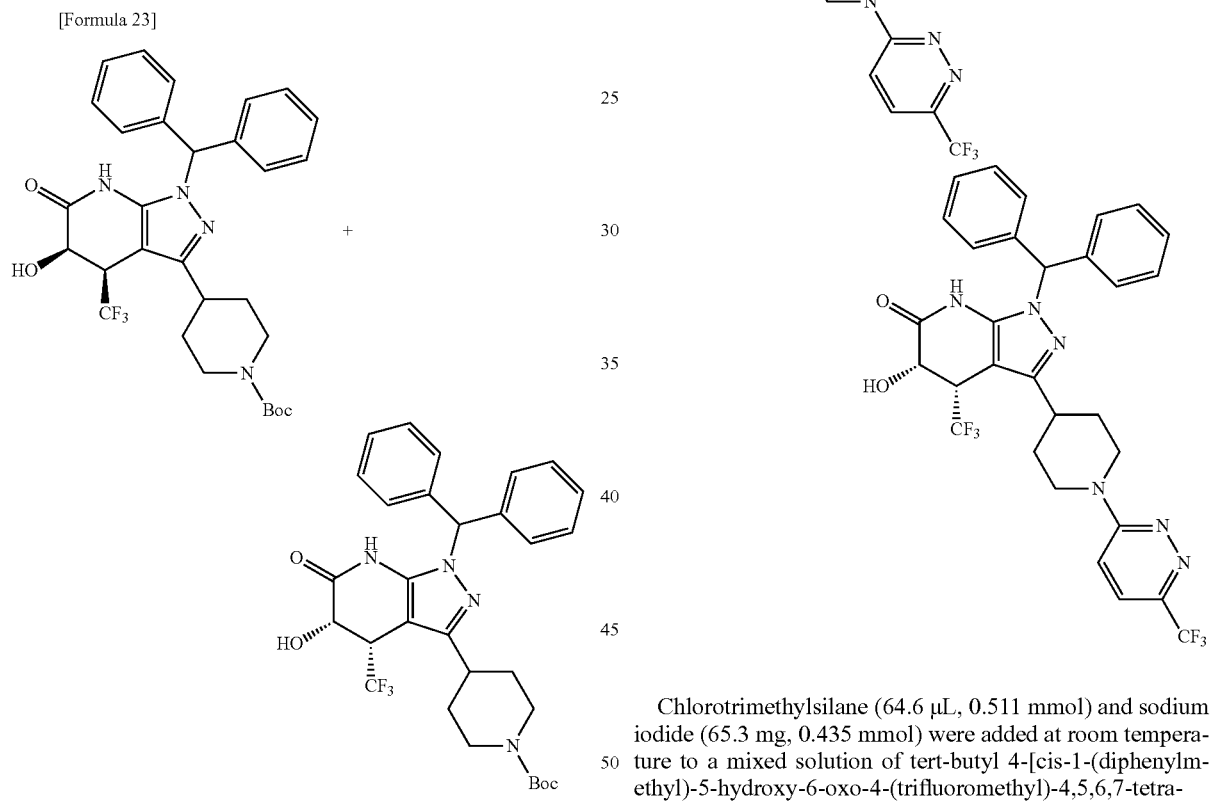

The title compound (115 mg, yield: 15%) was obtained through the same reaction as in the method described in Reference Example 4 using tert-butyl 4-[trans-1-(diphenylmethyl)-5-hydroxy-6-oxo-4-(trifluoromethyl)-4,5,6,7-tetrahydro-1H-pyrazolo[3,4-b]pyridin-3-yl]piperidine-1-carboxylate (765 mg, 1.34 mmol) produced in Reference Example 14 instead of trans-1-(diphenylmethyl)-5-hydroxy-4-(trifluoromethyl)-3-{1-[5-(trifluoromethyl)pyridin-2-yl]piperidin-4-yl}-, 4,5,7-tetrahydro-6H-pyrazolo[3,4-b]pyridin-6-one.

$^1$H-NMR (400 MHz, DMSO-$d_6$) δ: 11.21 (1H, s), 7.37-7.15 (10H, m), 6.74 (1H, s), 5.79 (1H, d, J=4 Hz), 4.57-4.54 (1H, m), 4.16-3.90 (3H, m), 2.86-2.39 (3H, m), 1.83-1.35 (4H, m), 1.39 (9H, s).

Chlorotrimethylsilane (64.6 μL, 0.511 mmol) and sodium iodide (65.3 mg, 0.435 mmol) were added at room temperature to a mixed solution of tert-butyl 4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidine-1-carboxylate (108 mg, 0.189 mmol) produced in Reference Example 16 in dichloromethane (3 mL) and acetonitrile (1 mL), and the mixture was stirred for 4 hours. The solvent in the reaction solution was distilled off under reduced pressure, and a saturated sodium bicarbonate aqueous solution was added to the residue, followed by extraction with ethyl acetate three times. The obtained organic layer was washed with brine and dried over anhydrous sodium sulfate, and the solvent was distilled off under reduced pressure to obtain a synthesis intermediate (94 mg).

3-Chloro-6-(trifluoromethyl)pyridazine (21 mg, 0.16 mmol) and N,N-diisopropylethylamine (24 μL, 0.14 mmol) were added to a solution of a portion (45 mg) of the synthesis intermediate obtained by the procedures described above in DMSO (1 mL), and the mixture was stirred at room temperature for 18 hours. To the reaction solution, water was added, followed by extraction with ethyl acetate three times. The organic layer was washed with brine and dried over anhydrous magnesium sulfate, and the solvent was distilled off under reduced pressure. The obtained residue was purified by silica gel column chromatography [elute: hexane/ethyl acetate=95/5-50/50] to obtain the title compound (34 mg, yield: 58%).

$^1$H-NMR (400 MHz, DMSO-d$_6$) δ: 11.22 (1H, s), 7.75 (1H, d, J=10 Hz), 7.41 (1H, d, J=10 Hz), 7.34-7.24 (8H, m), 7.17-7.13 (2H, m), 6.75 (1H, s), 5.81 (1H, d, J=4 Hz), 4.61-4.48 (3H, m), 4.24-4.11 (1H, m), 3.22-3.09 (2H, m), 3.05-2.94 (1H, m), 2.03-1.94 (1H, m), 1.87-1.79 (1H, m), 1.76-1.63 (1H, m), 1.62-1.51 (1H, m).

(Reference Example 18) trans-1-(Diphenylmethyl)-5-hydroxy-3-{1-[2-isopropyl-6-(trifluoromethyl)pyrimidin-4-yl]piperidin-4-yl}-4-(trifluoromethyl)-1,4,5,7-tetrahydro-6H-pyrazolo[3,4-b]pyridin-6-one

[Formula 25]

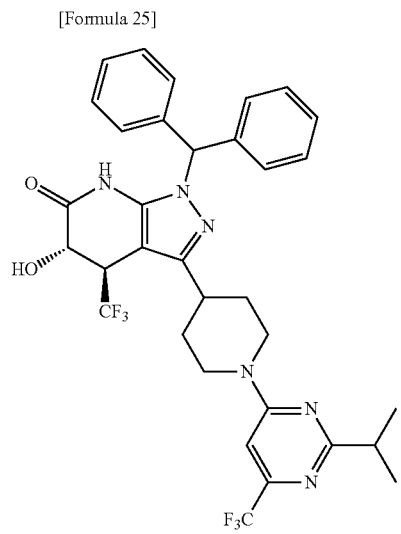

+

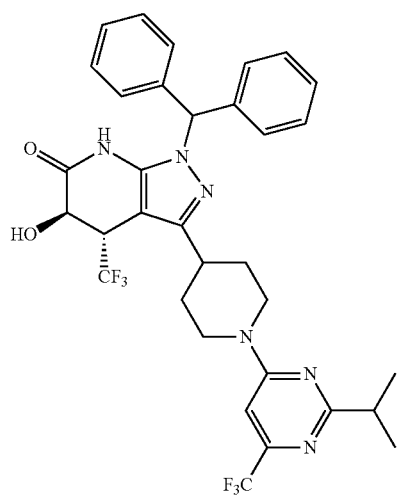

The title compound (300 mg, yield: 96%) was obtained through the same reaction as in the method described in Reference Example 15 using 4-chloro-2-isopropyl-6-(trifluoromethyl)pyrimidine (compound described in the pamphlet of WO2010/134478, 270 mg, 1.20 mmol) instead of 3-chloro-6-(trifluoromethyl)pyridazine.

$^1$H-NMR (400 MHz, DMSO-d$_6$) δ: 11.27 (1H, s), 7.38-7.23 (9H, m), 7.18 (2H, d, J=7 Hz), 7.07 (1H, s), 6.82 (1H, s), 6.69 (1H, d, J=6 Hz), 4.20 (1H, d, J=6 Hz), 4.03-3.89 (1H, m), 3.19-2.86 (5H, m), 1.98-1.41 (4H, m), 1.21 (6H, d, J=7 Hz).

(Reference Example 19) trans-1-(Diphenylmethyl)-5-hydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one

[Formula 26]

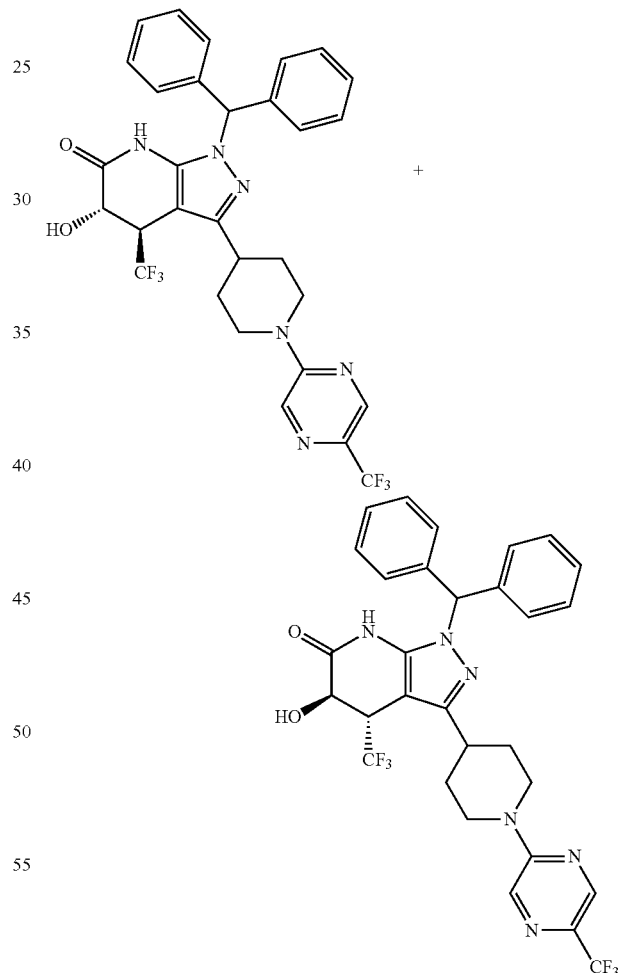

The title compound (106 mg, yield: 62%) was obtained through the same reaction as in the method described in Reference Example 15 using 2-chloro-5-(trifluoromethyl)pyrazine (120 mg, 0.657 mmol) instead of 3-chloro-6-(trifluoromethyl)pyridazine.

39

¹H-NMR (400 MHz, DMSO-d₆) δ: 11.27 (1H, s), 8.45 (1H, s), 8.43 (1H, s), 7.35-7.17 (10H, m), 6.82 (1H, s), 6.70 (1H, d, J=5 Hz), 4.52-4.46 (2H, m), 4.21-4.19 (1H, m), 3.99-3.92 (1H, m), 3.19-3.14 (2H, m), 3.02-2.95 (1H, m), 1.94-1.85 (2H, m), 1.72-1.51 (2H, m).

(Reference Example 20) 6-{4-[cis-1-(Diphenylmethyl)-5-hydroxy-6-oxo-4-(trifluoromethyl)-4,5,6,7-tetrahydro-1H-pyrazolo[3,4-b]pyridin-3-yl]piperidin-1-yl}-4-(trifluoromethyl)pyridine-3-carbonitrile

[Formula 27]

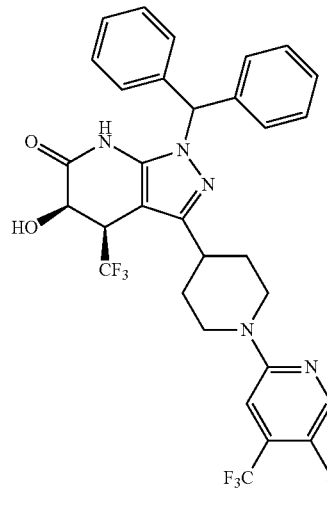

+

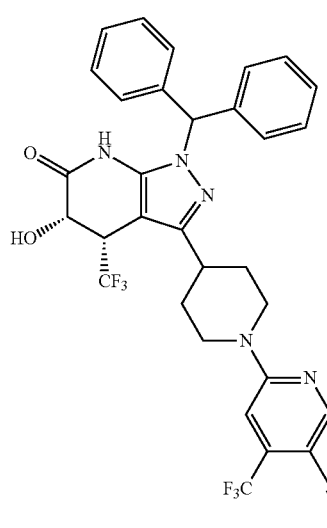

The title compound (47 mg, yield: 70%) was obtained through the same reaction as in the method described in Reference Example 17 using 6-chloro-4-(trifluoromethyl)pyridine-3-carbonitrile (26 mg, 0.12 mmol) instead of 3-chloro-6-(trifluoromethyl)pyridazine.

40

¹H-NMR (400 MHz, DMSO-d₆) δ: 11.23 (1H, s), 8.67 (1H, s), 7.37-7.12 (11H, m), 6.75 (1H, s), 5.82 (1H, d, J=4 Hz), 4.69-4.44 (3H, m), 4.24-4.12 (1H, m), 3.26-3.10 (2H, m), 3.05-2.94 (1H, m), 1.91-1.80 (2H, m), 1.71-1.50 (2H, m).

(Reference Example 21) cis-3-{1-[3-Chloro-5-(trifluoromethyl)pyridin-2-yl]piperidin-4-yl}-1-(diphenylmethyl)-5-hydroxy-4-(trifluoromethyl)-1,4,5,7-tetrahydro-6H-pyrazolo[3,4-b]pyridin-6-one

[Formula 28]

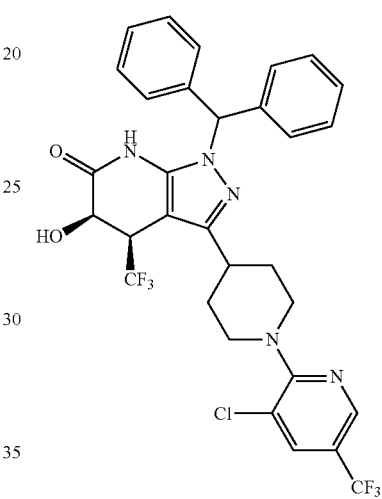

+

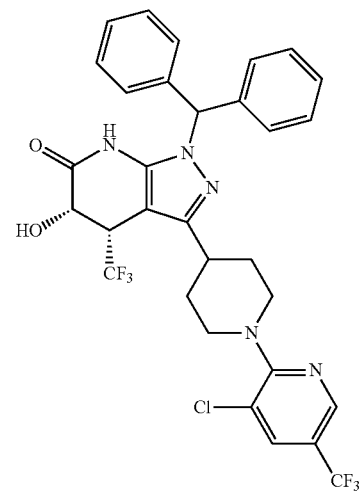

The title compound (40 mg, yield: 58%) was obtained through the same reaction as in the method described in Reference Example 17 using 3-chloro-2-fluoro-5-(trifluoromethyl)pyridine (25 mg, 0.13 mmol) instead of 3-chloro-6-(trifluoromethyl)pyridazine.

¹H-NMR (400 MHz, DMSO-d₆) δ: 11.22 (1H, s), 8.54 (1H, d, J=2 Hz), 8.16 (1H, d, J=2 Hz), 7.39-7.25 (8H, m), 7.18-7.14 (2H, m), 6.76 (1H, s), 5.81 (1H, d, J=4 Hz), 4.61-4.55 (1H, m), 4.22-4.10 (1H, m), 4.09-3.97 (2H, m), 3.07-2.83 (3H, m), 2.02-1.93 (1H, m), 1.87-1.79 (2H, m), 1.77-1.65 (1H, m).

(Reference Example 22) cis-1-(Diphenylmethyl)-5-hydroxy-4-(trifluoromethyl)-3-{1-[4-(trifluoromethyl)-1,3-thiazol-2-yl]piperidin-4-yl}-1,4,5,7-tetrahydro-6H-pyrazolo[3,4-b]pyridin-6-one

[Formula 29]

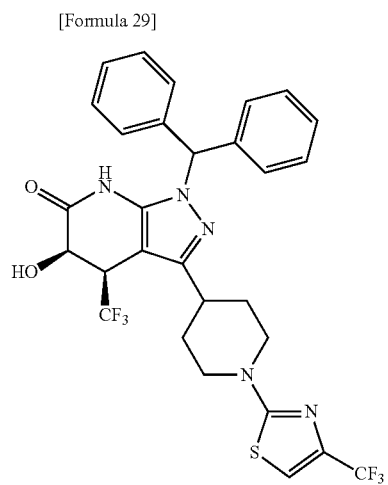

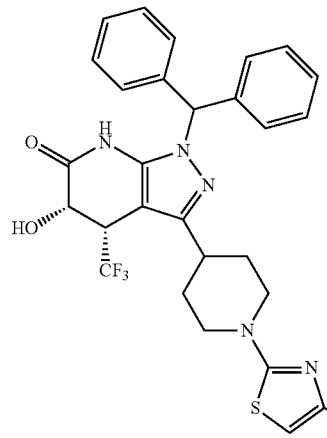

The title compound (12 mg, yield: 15%) was obtained through the same reaction as in the method described in Reference Example 17 using 2-chloro-4-(trifluoromethyl)-1,3-thiazole (45 mg, 0.13 mmol) instead of 3-chloro-6-(trifluoromethyl)pyridazine.

¹H-NMR (400 MHz, CDCl₃) δ: 7.39-7.33 (7H, m), 7.08-7.02 (4H, m), 6.90 (1H, d, J=1 Hz), 6.81 (1H, brs), 6.67 (1H, s), 4.49 (1H, d, J=7 Hz), 4.07-3.96 (2H, m), 3.65 (1H, d, J=2 Hz), 3.18-3.09 (2H, m), 2.83-2.74 (1H, m), 1.99-1.76 (4H, m).

(Reference Example 23) cis-1-(Diphenylmethyl)-5-hydroxy-4-(trifluoromethyl)-3-{1-[6-(trifluoromethyl)pyridin-2-yl]piperidin-4-yl}-1,4,5,7-tetrahydro-6H-pyrazolo[3,4-b]pyridin-6-one

[Formula 30]

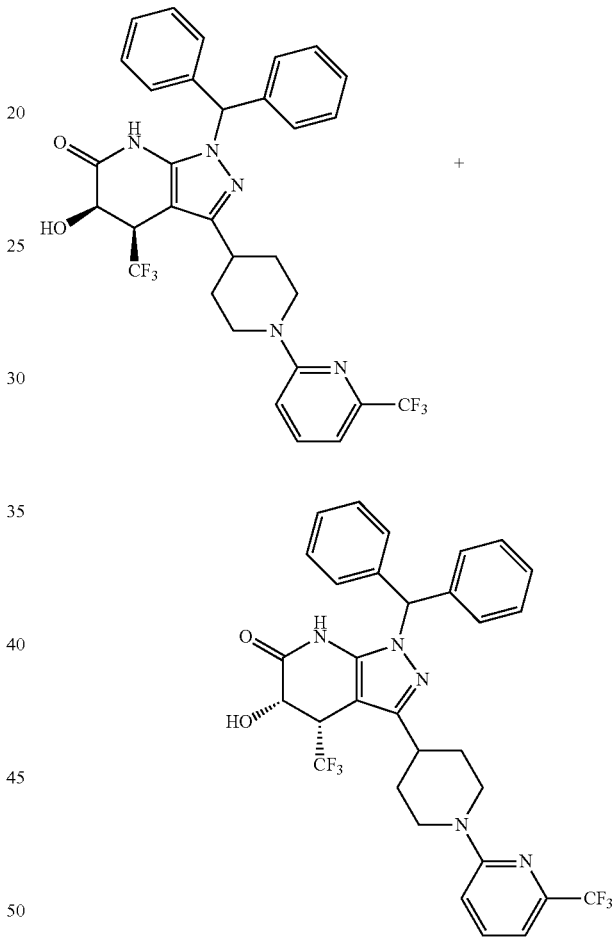

The title compound (18 mg, yield: 24%) was obtained through the same reaction as in the method described in Reference Example 17 using 2-fluoro-6-(trifluoromethyl)pyridine (24 mg, 0.15 mmol) instead of 3-chloro-6-(trifluoromethyl)pyridazine.

¹H-NMR (400 MHz, DMSO-d₆) δ: 11.21 (1H, s), 7.70 (1H, t, J=8 Hz), 7.37-7.23 (8H, m), 7.18-7.10 (3H, m), 6.97 (1H, d, J=7 Hz), 6.74 (1H, s), 5.80 (1H, d, J=4 Hz), 4.60-4.55 (1H, m), 4.41-4.31 (2H, m), 4.20-4.10 (1H, m), 3.04-2.85 (3H, m), 1.98-1.90 (1H, m), 1.85-1.75 (1H, m), 1.72-1.60 (1H, m), 1.60-1.48 (1H, m).

(Reference Example 24) cis-1-(Diphenylmethyl)-5-hydroxy-4-(trifluoromethyl)-3-{1-[4-(trifluoromethyl)pyridin-2-yl]piperidin-4-yl}-1,4,5,7-tetrahydro-6H-pyrazolo[3,4-b]pyridin-6-one

[Formula 31]

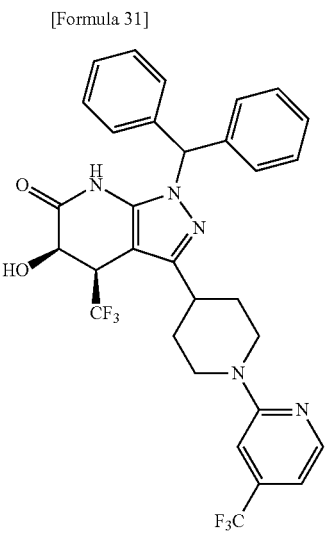

+

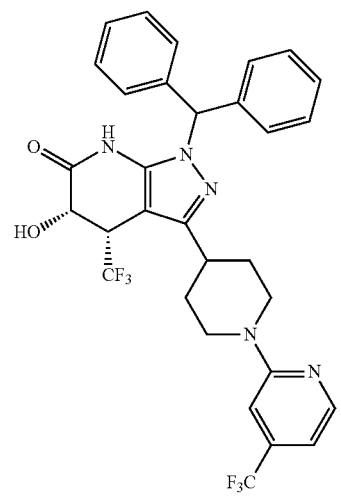

The title compound (29 mg, yield: 36%) was obtained through the same reaction as in the method described in Reference Example 17 using 2-fluoro-4-(trifluoromethyl)pyridine (42 μL, 0.34 mmol) instead of 3-chloro-6-(trifluoromethyl)pyridazine.

$^1$H-NMR (400 MHz, DMSO-$d_6$) δ: 11.21 (1H, s), 8.29 (1H, d, J=5 Hz), 7.37-7.23 (8H, m), 7.18-7.13 (2H, m), 7.08 (1H, s), 6.81 (1H, d, J=5 Hz), 6.74 (1H, s), 5.80 (1H, d, J=4 Hz), 4.61-4.54 (1H, m), 4.47-4.36 (2H, m), 4.22-4.10 (1H, m), 3.06-2.86 (3H, m), 1.97-1.88 (1H, m), 1.83-1.74 (1H, m), 1.72-1.60 (1H, m), 1.60-1.47 (1H, m).

(Example 1) trans-5-Hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one

[Formula 32]

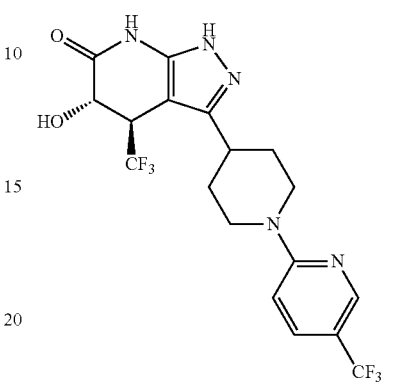

+

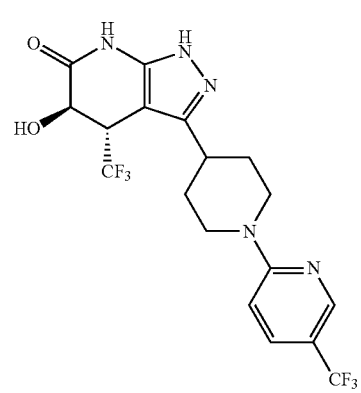

Triethylsilane (0.02 mL, 0.13 mmol) and trifluoroacetic acid (2 mL) were added to a solution of trans-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one (34 mg, 0.0552 mmol) produced in Reference Example 3 in dichloromethane (2 mL), and the mixture was stirred at room temperature for 15 minutes. To the reaction solution, a saturated sodium bicarbonate aqueous solution was added, followed by extraction with ethyl acetate three times. The organic layer was washed with brine and dried over anhydrous magnesium sulfate, and the solvent was distilled off under reduced pressure. The obtained residue was purified by silica gel column chromatography [elute: hexane/ethyl acetate=60/40-0/100 (gradient)] to obtain the title compound (20 mg, yield: 81%).

$^1$H-NMR (400 MHz, DMSO-$d_6$) δ: 12.13 (1H, s), 10.52 (1H, s), 8.42 (1H, s), 7.79 (1H, t, J=6 Hz), 6.54 (1H, d, J=5 Hz), 4.63-4.52 (2H, m), 4.16 (1H, d, J=5 Hz), 3.94-3.85 (1H, m), 3.14-2.92 (3H, m), 1.83-1.62 (4H, m), 1.29-1.21 (1H, m);

MS (ESI) m/z: 450 (M+H)$^+$.

(Example 2) cis-5-Hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one

[Formula 33]

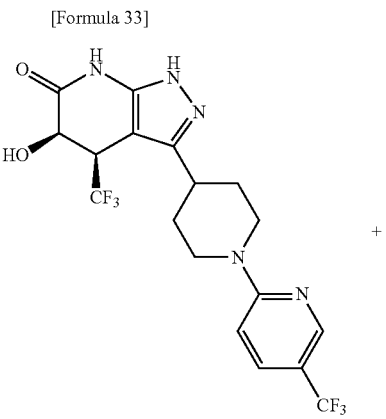

Triethylsilane (0.05 mL, 0.3 mmol) and trifluoroacetic acid (3 mL) were added to a solution of cis-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one (95 mg, 0.154 mmol) produced in Reference Example 4 in dichloromethane (3 mL), and the mixture was stirred at room temperature for 1 hour. To the reaction solution, a saturated sodium bicarbonate aqueous solution was added, followed by extraction with ethyl acetate three times. The organic layer was washed with brine and dried over anhydrous magnesium sulfate, and the solvent was distilled off under reduced pressure. The obtained residue was purified by silica gel column chromatography [NH-silica gel, elute: ethyl acetate/methanol=100/0-95/5 (gradient)] to obtain the title compound (45 mg, yield: 65%).

$^1$H-NMR (400 MHz, DMSO-$d_6$) δ: 12.18 (1H, s), 10.53 (1H, s), 8.42 (1H, s), 7.79 (1H, dd, J=9 Hz, 2 Hz), 7.01 (1H, d, J=9 Hz), 5.51 (1H, d, J=4 Hz), 4.62-4.52 (2H, m), 4.46-4.42 (1H, m), 4.20-4.11 (1H, m), 3.13-2.93 (3H, m), 1.89-1.56 (4H, m);

MS (ESI) m/z: 450 (M+H)$^+$.

(Example 3) (+)-cis-5-Hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one

[Formula 34]

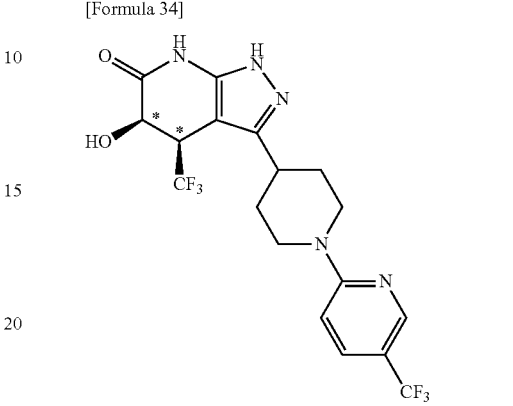

cis-5-Hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one (0.14 g, 0.31 mmol) produced in Example 2 was dissolved in ethanol (30 mL) under heating. To the solution, hexane (10 mL) was then added, and the resulting solution was purified in 10 divided portions by HPLC [column: Chiralpak IA (20 mm i.d.×250 mm); manufactured by Daicel Corporation, elute: hexane/ethanol=60/40, flow rate: 15 mL/min] to obtain the title compound (51 mg, yield: 36%, optically active form).

The optical purity was measured using HPLC [column: Chiralpak IA (4.6 mm i.d.×250 mm); manufactured by Daicel Corporation, elute: hexane/IPA=60/40, flow rate: 1.0 mL/min].

Optical purity: 99% or higher (retention time: 10.4 min); $[\alpha]_D^{25}$=+12° (DMF, c=1.01).

(Example 4) 4,5-Dihydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one

[Formula 35]

Triethylsilane (0.015 mL, 0.094 mmol) and trifluoroacetic acid (1 mL) were added to a solution of 1-(diphenylmethyl)-4,5-dihydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one (31 mg, 0.049 mmol) produced in Reference Example 6 in dichloromethane (1 mL), and the mixture was stirred for 30 minutes. To the reaction solution, a saturated sodium bicarbonate aqueous solution was added, followed by extraction with ethyl acetate three times. The organic layer was washed with brine and dried over anhydrous magnesium sulfate, and the solvent was distilled off under reduced pressure. The obtained residue was purified by silica gel column chromatography [elute: hexane/ethyl acetate=60/40-20/80] to obtain the title compound (15 mg, 0.032 mmol).

$^1$H-NMR (400 MHz, DMSO-$d_6$) δ: 12.22 (1H, s), 10.55 (1H, s), 8.42 (1H, s), 7.79 (1H, dd, J=9 Hz, 2 Hz), 7.00 (1H, d, J=9 Hz), 6.79 (1H, s), 5.66 (1H, d, J=4 Hz), 4.58 (2H, d, J=13 Hz), 4.35 (1H, s), 3.33-3.24 (1H, m), 2.94 (2H, t, J=12 Hz), 1.90 (1H, d, J=10 Hz), 1.76-1.55 (3H, m);

MS (ESI) m/z: 466 (M+H)$^+$.

(Example 5) cis-5-Hydroxy-3-[1-(5-isopropoxypyridin-2-yl)piperidin-4-yl]-4-(trifluoromethyl)-1,4,5,7-tetrahydro-6H-pyrazolo[3,4-b]pyridin-6-one The title compound (25 mg, yield: 54%) was obtained through the same reaction as in the method described in Example 2 using cis-1-(diphenylmethyl)-5-hydroxy-3-[1-(5-isopropoxypyridin-2-yl)piperidin-4-yl]-4-(trifluoromethyl)-1,4,5,7-tetrahydro-6H-pyrazolo[3,4-b]pyridin-6-one (64 mg, 0.11 mmol) produced in Reference Example 11 instead of cis-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.23 (1H, s), 10.54 (1H, s), 7.84 (1H, d, J=3 Hz), 7.25 (1H, dd, J=9 Hz, 3 Hz), 6.83 (1H, d, J=9 Hz), 5.51 (1H, d, J=4 Hz), 4.47-4.41 (2H, m), 4.32-4.21 (2H, m), 4.19-4.08 (1H, m), 2.98-2.87 (1H, m), 2.80-2.69 (2H, m), 1.86-1.62 (4H, m), 1.23 (6H, d, J=6 Hz);

MS (ESI) m/z: 440 (M+H)$^+$.

(Example 6) trans-5-Hydroxy-4-(trifluoromethyl)-3-{1-[6-(trifluoromethyl)pyridazin-3-yl]piperidin-4-yl}-1,4,5,7-tetrahydro-6H-pyrazolo[3,4-b]pyridin-6-one

[Formula 36]

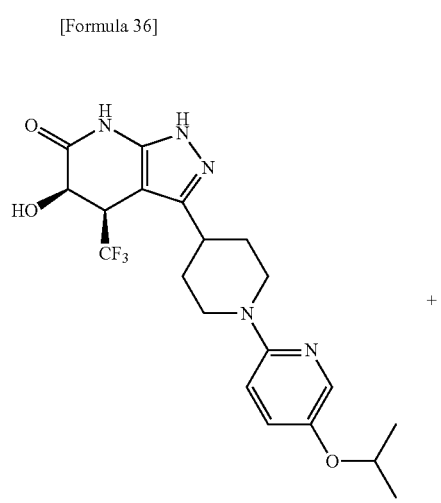

+

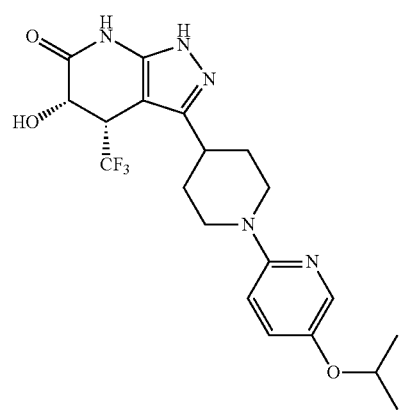

[Formula 37]

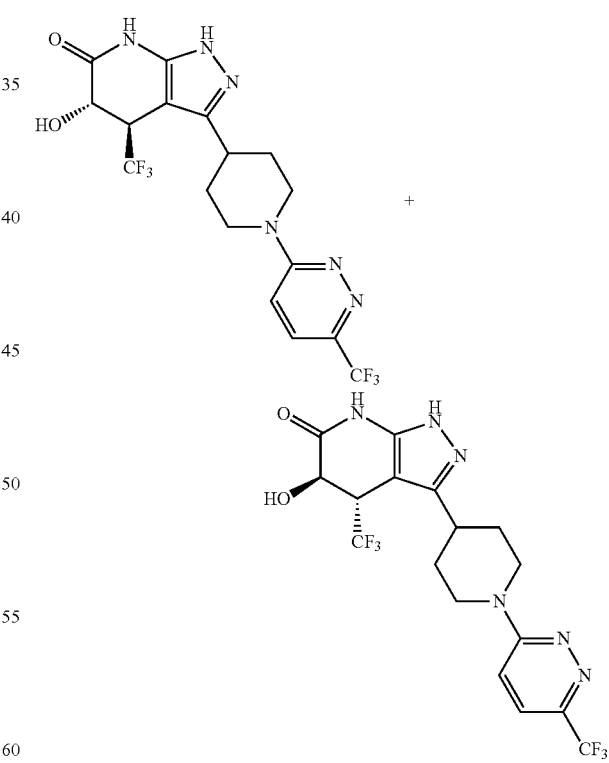

The title compound (14 mg, yield: 96%) was obtained through the same reaction as in the method described in Example 2 using trans-1-(diphenylmethyl)-5-hydroxy-4-(trifluoromethyl)-3-{1-[6-(trifluoromethyl)pyridazin-3-yl]piperidin-4-yl}-1,4,5,7-tetrahydro-6H-pyrazolo[3,4-b]pyridin-6-one (20 mg, 0.0324 mmol) produced in Reference Example 15 instead of cis-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.14 (1H, s), 10.53 (1H, s), 7.82 (1H, d, J=10 Hz), 7.47 (1H, d, J=10 Hz), 6.55 (1H, d, J=5 Hz), 4.69-4.62 (2H, m), 4.17-4.16 (1H, m), 3.94-3.86 (1H, m), 3.17-3.04 (3H, m), 1.86-1.69 (4H, m);
MS (ESI) m/z: 451 (M+H)$^+$.

(Example 7) cis-5-Hydroxy-4-(trifluoromethyl)-3-{1-[6-(trifluoromethyl)pyridazin-3-yl]piperidin-4-yl}-1,4,5,7-tetrahydro-6H-pyrazolo[3,4-b]pyridin-6-one

[Formula 38]

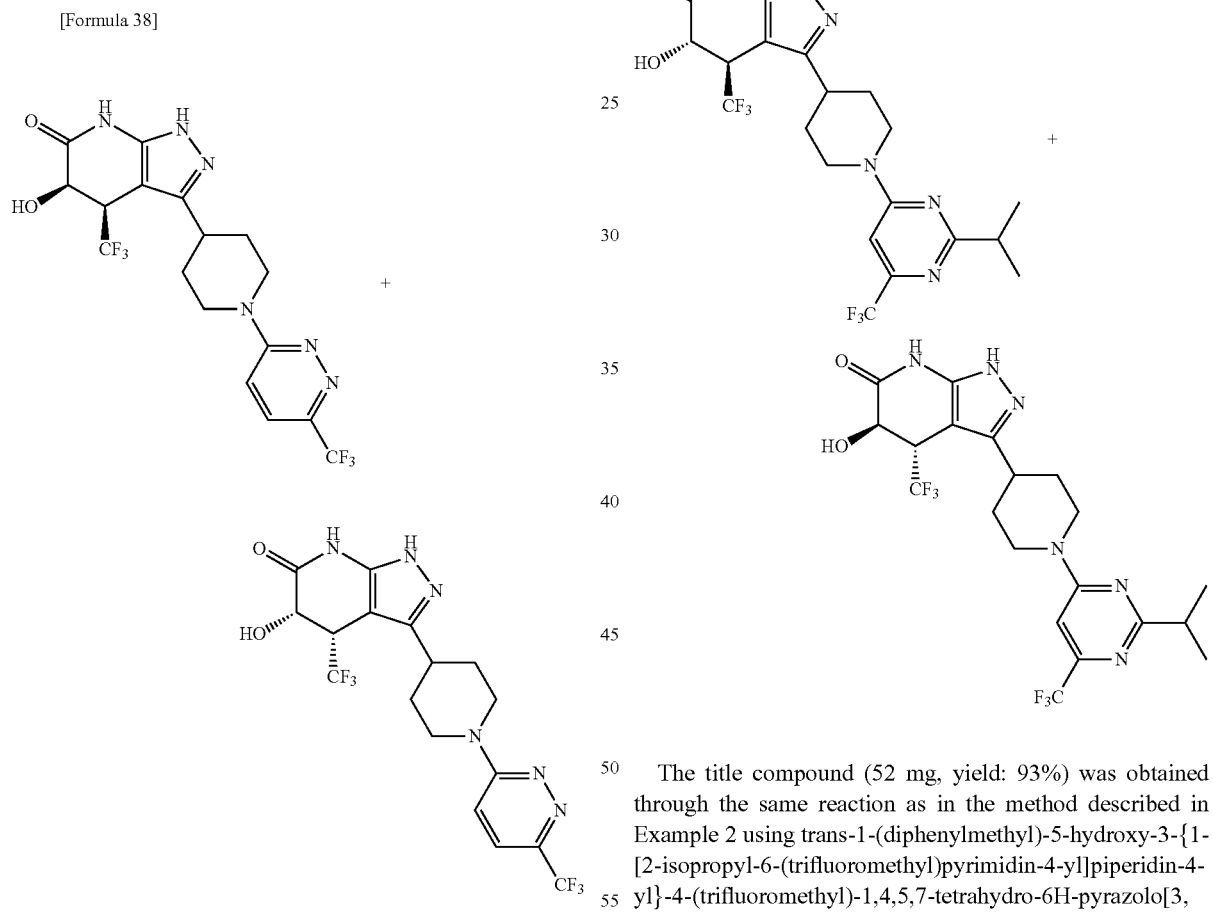

The title compound (17 mg, yield: 73%) was obtained through the same reaction as in the method described in Example 2 using cis-1-(diphenylmethyl)-5-hydroxy-4-(trifluoromethyl)-3-{1-[6-(trifluoromethyl)pyridazin-3-yl]piperidin-4-yl}-1,4,5,7-tetrahydro-6H-pyrazolo[3,4-b]pyridin-6-one (32 mg, 0.052 mmol) produced in Reference Example 17 instead of cis-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.19 (1H, s), 10.54 (1H, s), 7.81 (1H, d, J=10 Hz), 7.47 (1H, d, J=10 Hz), 5.53 (1H, d, J=4 Hz), 4.73-4.60 (2H, m), 4.48-4.41 (1H, m), 4.23-4.11 (1H, m), 3.19-3.03 (3H, m), 1.93-1.84 (1H, m), 1.82-1.61 (3H, m);
MS (ESI) m/z: 451 (M+H)$^+$.

(Example 8) trans-5-Hydroxy-3-{1-[2-isopropyl-6-(trifluoromethyl)pyrimidin-4-yl]piperidin-4-yl}-4-(trifluoromethyl)-1,4,5,7-tetrahydro-6H-pyrazolo[3,4-b]pyridin-6-one

[Formula 39]

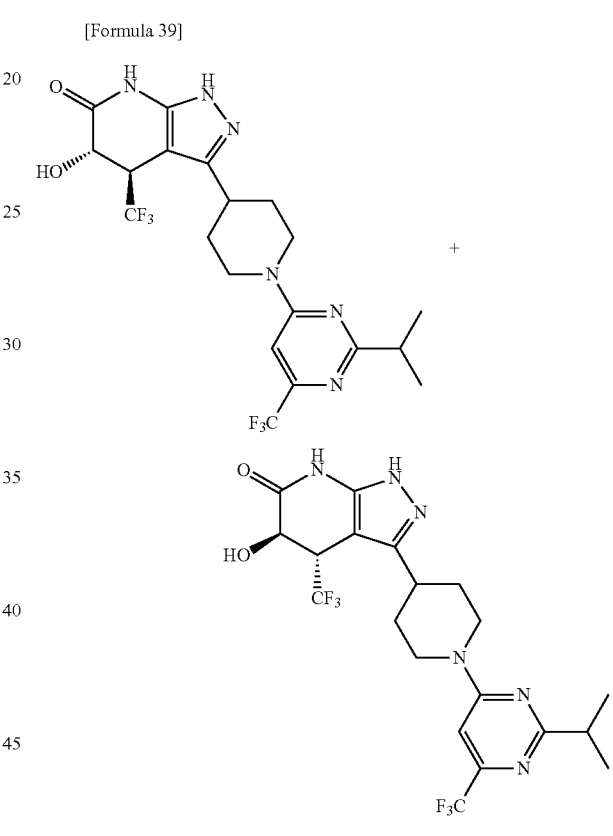

The title compound (52 mg, yield: 93%) was obtained through the same reaction as in the method described in Example 2 using trans-1-(diphenylmethyl)-5-hydroxy-3-{1-[2-isopropyl-6-(trifluoromethyl)pyrimidin-4-yl]piperidin-4-yl}-4-(trifluoromethyl)-1,4,5,7-tetrahydro-6H-pyrazolo[3,4-b]pyridin-6-one (75 mg, 0.114 mmol) produced in Reference Example 18 instead of cis-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.11 (1H, s), 10.53 (1H, s), 7.14 (1H, s), 6.55 (1H, brs), 5.34-4.58 (2H, m), 4.16 (1H, s), 3.90 (1H, q, J=10 Hz), 3.82-3.35 (2H, m), 3.17-2.87 (2H, m), 1.86-1.60 (4H, m), 1.23 (6H, d, J=7 Hz);
MS (ESI) m/z: 493 (M+H)$^+$.

(Example 9) cis-5-Hydroxy-3-{1-[2-isopropyl-6-(trifluoromethyl)pyrimidin-4-yl]piperidin-4-yl}-4-(trifluoromethyl)-1,4,5,7-tetrahydro-6H-pyrazolo[3,4-b]pyridin-6-one

[Formula 40]

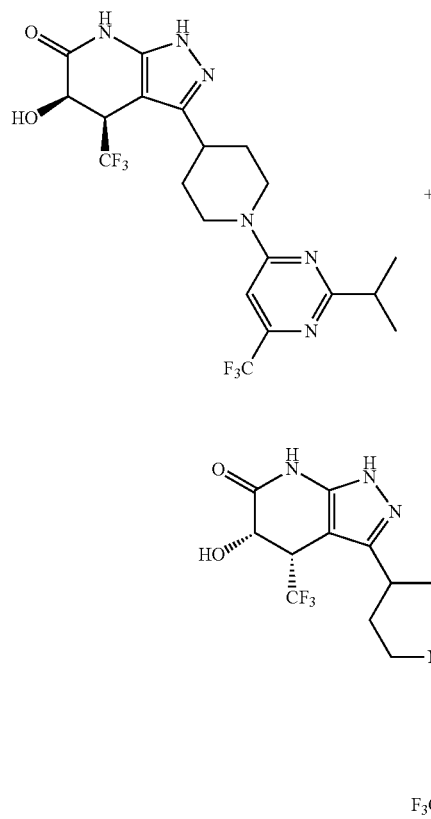

A protected form of diphenylmethyl was obtained through the same reaction as in the method described in Reference Example 4 using trans-1-(diphenylmethyl)-5-hydroxy-3-{1-[2-isopropyl-6-(trifluoromethyl)pyrimidin-4-yl]piperidin-4-yl}-4-(trifluoromethyl)-1,4,5,7-tetrahydro-6H-pyrazolo[3,4-b]pyridin-6-one (300 mg, 0.456 mmol) produced in Reference Example 18 instead of trans-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

The title compound (7 mg, yield: 9%) was obtained through the same reaction as in the method described in Example 2 using the protected form of diphenylmethyl obtained by the procedures described above instead of cis-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.12 (1H, s), 10.50 (1H, s), 7.10 (1H, s), 5.49 (1H, s), 4.41-4.39 (1H, m), 4.17-4.05 (1H, m), 3.10-2.84 (4H, m), 1.86-1.52 (4H, m), 1.19 (6H, d, J=7 Hz);

MS (ESI) m/z: 493 (M+H)$^+$.

(Example 10) trans-5-Hydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one

[Formula 41]

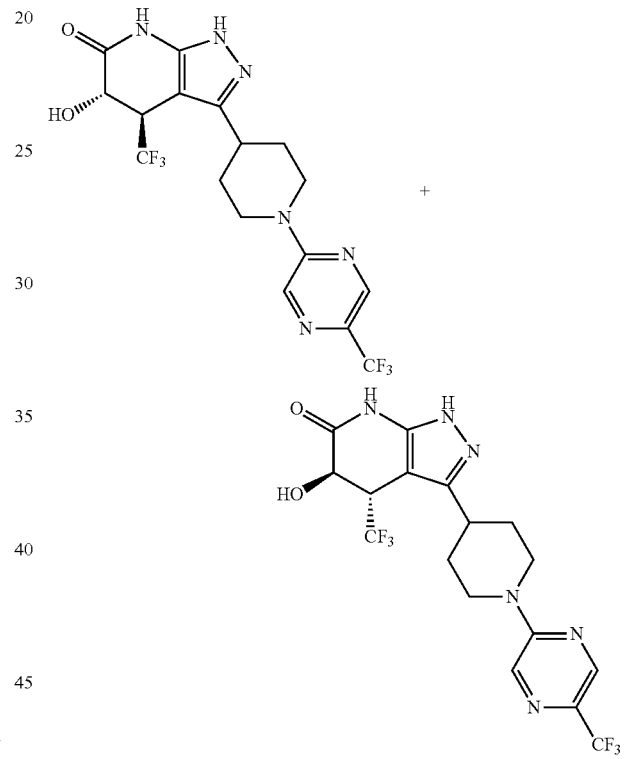

The title compound (70 mg, yield: 90%) was obtained through the same reaction as in the method described in Example 2 using trans-1-(diphenylmethyl)-5-hydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one (106 mg, 0.172 mmol) produced in Reference Example 19 instead of cis-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.13 (1H, s), 10.54 (1H, s), 8.51 (1H, s), 8.50 (1H, s), 6.59 (1H, d, J=5 Hz), 4.66-4.59 (2H, m), 4.17-4.16 (1H, m), 3.98-3.83 (1H, m), 3.18-2.98 (3H, m), 1.87-1.64 (4H, m);

MS (ESI) m/z: 451 (M+H)$^+$.

53

(Example 11) cis-5-Hydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one

[Formula 42]

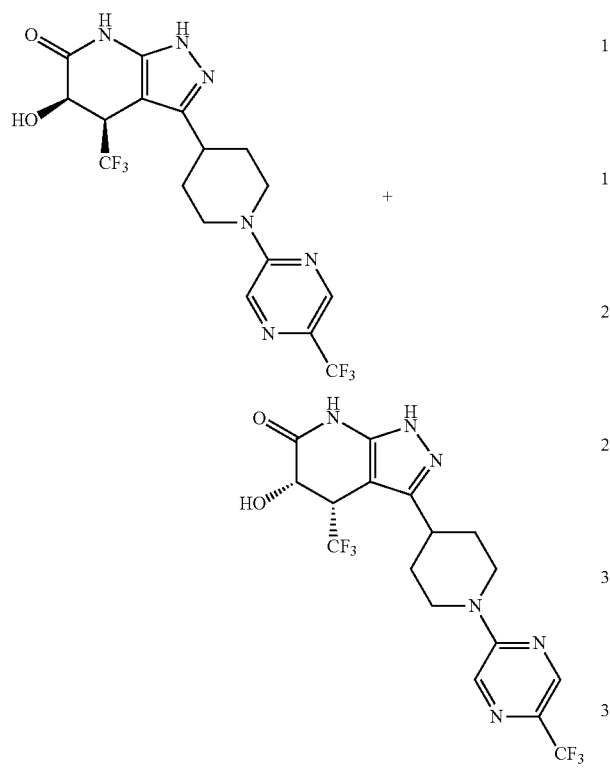

A synthesis intermediate was obtained through the same reaction as in the method described in Reference Example 15 using tert-butyl 4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidine-1-carboxylate (115 mg, 0.202 mmol) produced in Reference Example 16 instead of tert-butyl 4-[trans-1-(diphenylmethyl)-5-hydroxy-6-oxo-4-(trifluoromethyl)-4,5,6,7-tetrahydro-1H-pyrazolo[3,4-b]pyridin-3-yl]piperidine-1-carboxylate and 2-chloro-5-(trifluoromethyl)pyrazine (90 mg, 0.493 mmol) instead of 3-chloro-6-(trifluoromethyl)pyridazine.

The title compound (58 mg, yield: 99%) was obtained through the same reaction as in the method described in Example 2 using the synthesis intermediate obtained by the procedures described above instead of cis-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.18 (1H, s), 10.54 (1H, s), 8.51 (1H, s), 8.50 (1H, s), 5.54 (1H, d, J=4 Hz), 4.65-4.59 (2H, m), 4.46-4.43 (1H, m), 4.22-4.13 (1H, m), 3.16-3.03 (3H, m), 1.90-1.61 (4H, m);

MS (ESI) m/z: 451 (M+H)$^+$.

54

(Example 12) cis-5-Hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one

[Formula 43]

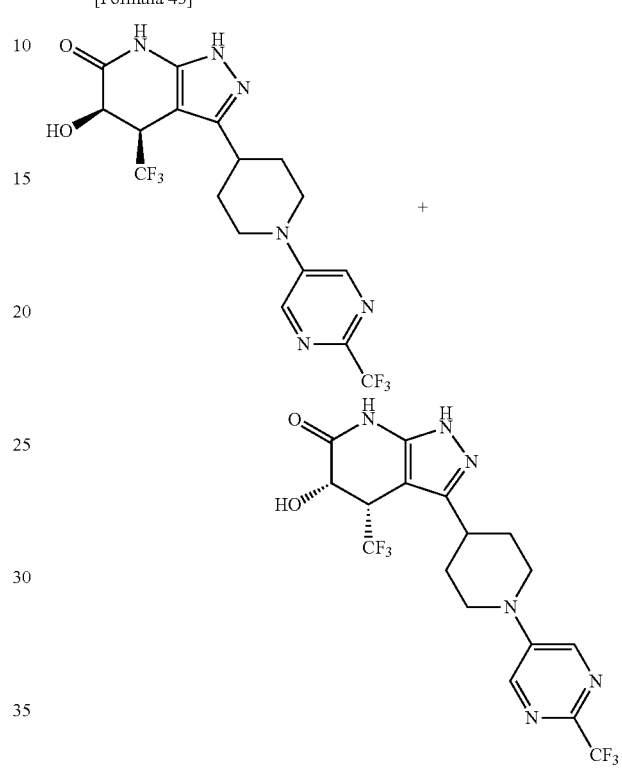

Chlorotrimethylsilane (25 μL, 0.20 mmol) and sodium iodide (25 mg, 0.17 mmol) were added at room temperature to a mixed solution of tert-butyl 4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidine-1-carboxylate (42 mg, 0.074 mmol) produced in Reference Example 16 in dichloromethane (3 mL) and acetonitrile (1 mL), and the mixture was stirred for 2 hours. The solvent in the reaction solution was distilled off under reduced pressure, and a saturated sodium bicarbonate aqueous solution was added to the residue, followed by extraction with ethyl acetate three times. The obtained organic layer was washed with brine and dried over anhydrous sodium sulfate, and the solvent was distilled off under reduced pressure to obtain a synthesis intermediate.

5-Chloro-2-(trifluoromethyl)pyrimidine (30 mg, 0.16 mmol) and 1,8-diazabicyclo[5.4.0]-7-undecene (0.050 mL, 0.33 mmol) were added to a solution of the synthesis intermediate obtained by the procedures described above in DMSO (3 mL), and the mixture was stirred at 70° C. for 18 hours. To the reaction solution, water was added, followed by extraction with ethyl acetate three times. The organic layer was washed with brine and dried over anhydrous magnesium sulfate, and the solvent was distilled off under reduced pressure. The obtained residue was purified by silica gel column chromatography [elute: hexane/ethyl acetate=80/20-0/100] to obtain a protected form of diphenylmethyl.

The title compound (6.7 mg, yield: 20%) was obtained through the same reaction as in the method described in Example 2 using the protected form of diphenylmethyl obtained by the procedures described above instead of cis-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.22 (1H, s), 10.55 (1H, s), 8.67 (2H, s), 5.53 (1H, d, J=3 Hz), 4.44 (1H, d, J=6 Hz), 4.25-4.10 (3H, m), 3.14-2.95 (3H, m), 1.93-1.38 (4H, m);

MS (ESI) m/z: 451 (M+H)$^+$.

(Example 13) 6-{4-[cis-5-Hydroxy-6-oxo-4-(trifluoromethyl)-4,5,6,7-tetrahydro-1H-pyrazolo[3,4-b]pyridin-3-yl]piperidin-1-yl}-4-(trifluoromethyl)pyridine-3-carbonitrile

[Formula 44]

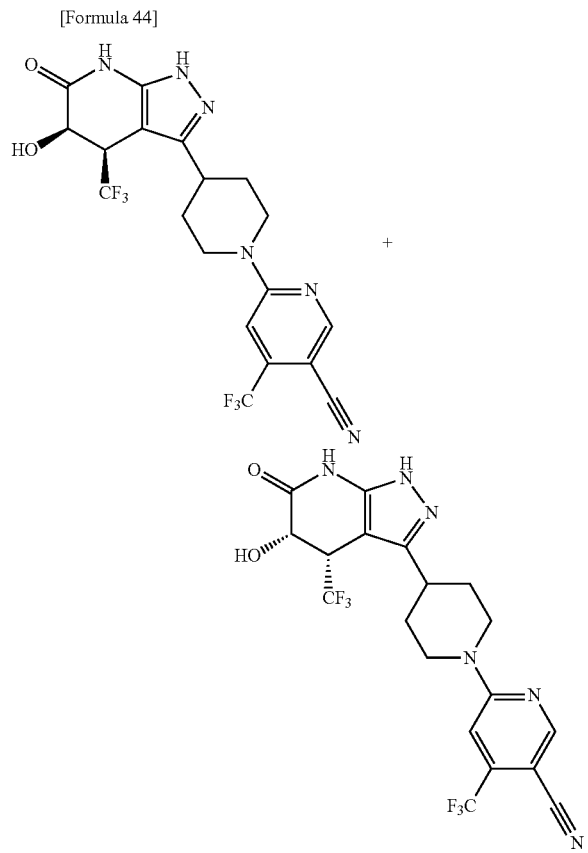

The title compound (23 mg, yield: 69%) was obtained through the same reaction as in the method described in Example 2 using 6-{4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidin-1-yl}-4-(trifluoromethyl)pyridine-3-carbonitrile (45 mg, 0.070 mmol) produced in Reference Example 20 instead of cis-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.17 (1H, s), 10.54 (1H, s), 8.73 (1H, s), 7.34 (1H, s), 5.54 (1H, d, J=4 Hz), 4.87-4.56 (2H, m), 4.48-4.41 (1H, m), 4.22-4.11 (1H, m), 3.20-3.01 (3H, m), 1.94-1.85 (1H, m), 1.82-1.57 (3H, m);

MS (ESI) m/z: 475 (M+H)$^+$.

(Example 14) cis-3-{1-[3-Chloro-5-(trifluoromethyl)pyridin-2-yl]piperidin-4-yl}-5-hydroxy-4-(trifluoromethyl)-1,4,5,7-tetrahydro-6H-pyrazolo[3,4-b]pyridin-6-one

[Formula 45]

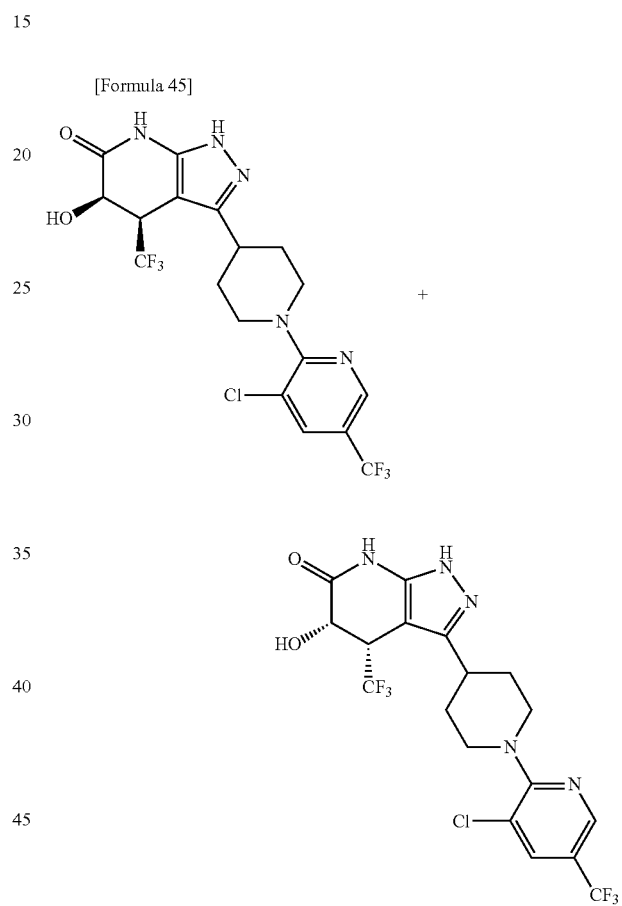

The title compound (21 mg, yield: 78%) was obtained through the same reaction as in the method described in Example 2 using cis-3-{1-[3-chloro-5-(trifluoromethyl)pyridin-2-yl]piperidin-4-yl}-1-(diphenylmethyl)-5-hydroxy-4-(trifluoromethyl)-1,4,5,7-tetrahydro-6H-pyrazolo[3,4-b]pyridin-6-one (36 mg, 0.055 mmol) produced in Reference Example 21 instead of cis-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.28 (1H, s), 10.54 (1H, s), 8.57 (1H, d, J=2 Hz), 8.20 (1H, d, J=2 Hz), 5.52 (1H, d, J=4 Hz), 4.47-4.42 (1H, m), 4.21-4.07 (3H, m), 3.07-2.91 (3H, m), 1.98-1.74 (4H, m);

MS (ESI) m/z: 484 (M+H)$^+$.

(Example 15) cis-5-Hydroxy-4-(trifluoromethyl)-3-{1-[4-(trifluoromethyl)-1,3-thiazol-2-yl]piperidin-4-yl}-1,4,5,7-tetrahydro-6H-pyrazolo[3,4-b]pyridin-6-one

[Formula 46]

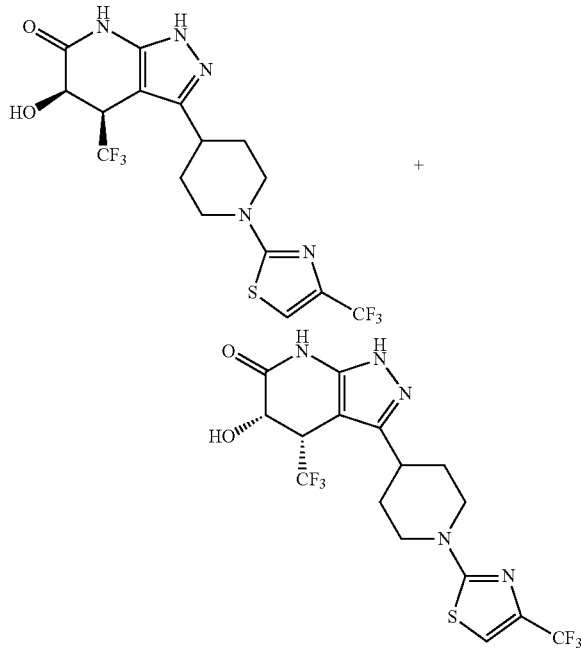

The title compound (6.4 mg, yield: 73%) was obtained through the same reaction as in the method described in Example 2 using cis-1-(diphenylmethyl)-5-hydroxy-4-(trifluoromethyl)-3-{1-[4-(trifluoromethyl)-1,3-thiazol-2-yl]piperidin-4-yl}-1,4,5,7-tetrahydro-6H-pyrazolo[3,4-b]pyridin-6-one (12 mg, 0.019 mmol) produced in Reference Example 22 instead of cis-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.26 (1H, s), 10.55 (1H, s), 7.55 (1H, d, J=1 Hz), 5.53 (1H, d, J=3 Hz), 4.45 (1H, dd, J=7 Hz, 4 Hz), 4.20-4.11 (1H, m), 4.04-3.95 (2H, m), 3.21-2.99 (3H, m), 1.92-1.67 (4H, m);
MS (ESI) m/z: 456 (M+H)$^+$.

(Example 16) cis-5-Hydroxy-4-(trifluoromethyl)-3-{1-[6-(trifluoromethyl)pyridin-2-yl]piperidin-4-yl}-1,4,5,7-tetrahydro-6H-pyrazolo[3,4-b]pyridin-6-one

[Formula 47]

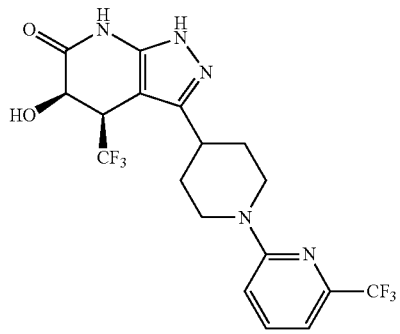

+

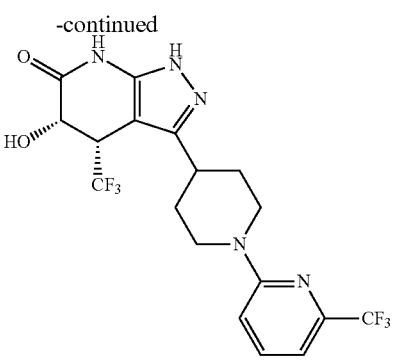

The title compound (16 mg, yield: 71%) was obtained through the same reaction as in the method described in Example 2 using cis-1-(diphenylmethyl)-5-hydroxy-4-(trifluoromethyl)-3-{1-[6-(trifluoromethyl)pyridin-2-yl]piperidin-4-yl}-1,4,5,7-tetrahydro-6H-pyrazolo[3,4-b]pyridin-6-one (31 mg, 0.050 mmol) produced in Reference Example 23 instead of cis-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.21 (1H, s), 10.54 (1H, s), 7.74 (1H, t, J=9 Hz), 7.17 (1H, d, J=9 Hz), 7.01 (1H, d, J=7 Hz), 5.51 (1H, d, J=4 Hz), 4.54-4.41 (3H, m), 4.22-4.09 (1H, m), 3.09-2.86 (3H, m), 1.92-1.82 (1H, m), 1.81-1.58 (3H, m);
MS (ESI) m/z: 450 (M+H)$^+$.

(Example 17) cis-5-Hydroxy-4-(trifluoromethyl)-3-{1-[4-(trifluoromethyl)pyridin-2-yl]piperidin-4-yl}-1,4,5,7-tetrahydro-6H-pyrazolo[3,4-b]pyridin-6-one

[Formula 48]

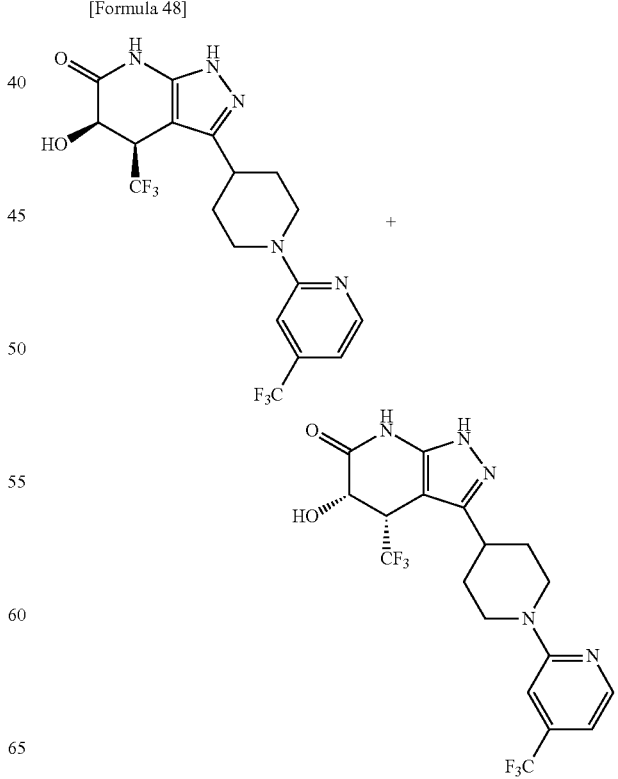

The title compound (14 mg, yield: 74%) was obtained through the same reaction as in the method described in Example 2 using cis-1-(diphenylmethyl)-5-hydroxy-4-(trifluoromethyl)-3-{1-[4-(trifluoromethyl)pyridin-2-yl]piperidin-4-yl}-1,4,5,7-tetrahydro-6H-pyrazolo[3,4-b]pyridin-6-one (26 mg, 0.042 mmol) produced in Reference Example 24 instead of cis-1-(diphenylmethyl)-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.19 (1H, s), 10.53 (1H, s), 8.33 (1H, d, J=5 Hz), 7.13 (1H, s), 6.85 (1H, d, J=5 Hz), 5.51 (1H, d, J=4 Hz), 4.62-4.49 (2H, m), 4.47-4.41 (1H, m), 4.21-4.10 (1H, m), 3.10-3.00 (1H, m), 3.00-2.86 (2H, m), 1.89-1.80 (1H, m), 1.78-1.57 (3H, m);

MS (ESI) m/z: 450 (M+H)$^+$.

(Reference Example 25) Methyl 3-[1-(tert-butoxycarbonyl)piperidin-4-yl]-1-(diphenylmethyl)-5-hydroxy-6-oxo-4-(trifluoromethyl)-4,5,6,7-tetrahydro-1H-pyrazolo[3,4-b]pyridine-5-carboxylate

[Formula 49]

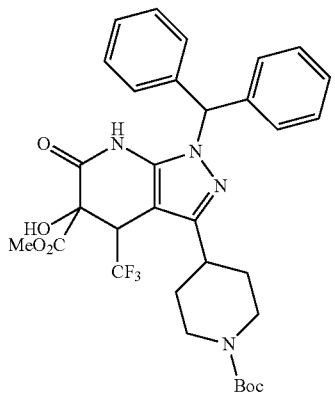

Lithium diisopropylamide (solution in hexane and THF, 14.5 mL, 15.8 mmol) was added dropwise at −78° C. to a solution of tert-butyl 4-[1-(diphenylmethyl)-6-oxo-4-(trifluoromethyl)-4,5,6,7-tetrahydro-1H-pyrazolo[3,4-b]pyridin-3-yl]piperidine-1-carboxylate (2.92 g, 5.27 mmol) produced in Reference Example 13 and dimethyl carbonate (0.665 mL, 7.90 mmol) in THF (50 mL). After removal of the cooling bath, the mixture was stirred for 30 minutes while its temperature was spontaneously raised. To the reaction solution, a saturated ammonium chloride aqueous solution was added, followed by extraction with ethyl acetate three times. The obtained organic layer was dried over magnesium sulfate, and the solvent was distilled off under reduced pressure. The obtained residue was purified by silica gel chromatography [NH-silica gel, elute: dichloromethane/methanol=100/0-90/10 (gradient)] to obtain a synthesis intermediate.

1,8-Diazabicyclo[5.4.0]-7-undecene (hereinafter, referred to as DBU; 1.57 mL, 10.5 mmol), (1S)-(+)-(10-camphorsulfonyl)oxaziridine (0.725 g, 3.16 mmol), and (1R)-(−)-(10-camphorsulfonyl)oxaziridine (0.725 g, 3.16 mmol) were added to a solution of the synthesis intermediate obtained by the procedures described above in THF (50 mL), and the mixture was stirred at room temperature for 2 hours. To the reaction solution, a saturated ammonium chloride aqueous solution was added, followed by extraction with ethyl acetate. The obtained organic layer was washed with a saturated sodium bicarbonate aqueous solution and brine in this order and dried over anhydrous sodium sulfate, and the solvent was distilled off under reduced pressure. The obtained residue was purified by silica gel column chromatography [elute: dichloromethane/methanol=99/1-90/10 (gradient)] to obtain the title compound (2.77 g, yield: 84%).

$^1$H-NMR (400 MHz, DMSO-$d_6$) δ: 11.52 (1H, s), 7.38-7.17 (10H, m), 6.86 (1H, s), 4.12-3.89 (3H, m), 3.73 (3H, s), 2.89-2.67 (3H, m), 1.81-1.29 (4H, m), 1.39 (9H, s).

(Reference Example 26) tert-Butyl (+)-4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidine-1-carboxylate

[Formula 50]

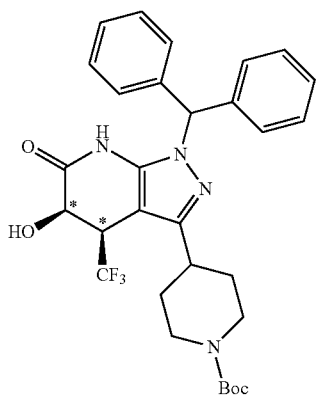

Lithium hydroxide monohydrate (0.873 g, 20.8 mmol) was added to a mixed solution of methyl 3-[1-(tert-butoxycarbonyl)piperidin-4-yl]-1-(diphenylmethyl)-5-hydroxy-6-oxo-4-(trifluoromethyl)-4,5,6,7-tetrahydro-1H-pyrazolo[3,4-b]pyridine-5-carboxylate (4.36 g, 6.94 mmol) produced in Reference Example 25 in 1,4-dioxane (50 mL) and water (20 mL), and the mixture was stirred at 50° C. for 1 hour. The reaction solution was cooled to room temperature, and a saturated ammonium chloride aqueous solution was added thereto, followed by extraction with ethyl acetate. The obtained organic layer was washed with a saturated sodium bicarbonate aqueous solution and brine in this order and dried over anhydrous sodium sulfate, and the solvent was distilled off under reduced pressure. The obtained residue was purified by silica gel column chromatography [elute: hexane/ethyl acetate=95/5-50/50 (gradient)] to obtain a synthesis intermediate.

A portion (1.23 g) of the synthesis intermediate obtained by the procedures described above was dissolved in ethyl acetate. To the solution, a neutral silica gel was added for adsorption, and the solvent was distilled off under reduced pressure. The obtained powder was purified by flash LC [column: Chiralflash IC (30 mm i.d.×100 mm); manufactured by Daicel Corporation, elute: hexane/ethanol=91/9, flow rate: 12 mL/min] to obtain the title compound (0.55 g, yield: 27%, optically active form).

The optical purity was measured using HPLC [column: Chiralpak IA (4.6 mm i.d.×250 mm); manufactured by Daicel Corporation, elute: hexane/IPA=70/30, flow rate: 1.0 mL/min].

Optical purity: 99% or higher (retention time: 4.3 min); $[α]_D^{25}$=+35° (DMF, c=1.00).

(Example 18) (+)-cis-5-Hydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one

[Formula 51]

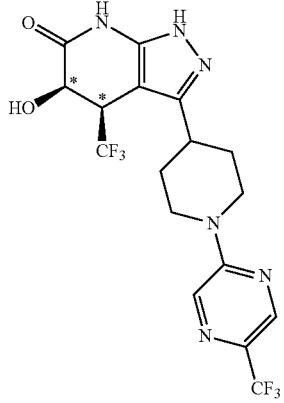

Chlorotrimethylsilane (72.3 µL, 0.573 mmol) and sodium iodide (73.1 mg, 0.488 mmol) were added to a mixed solution of tert-butyl (+)-4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidine-1-carboxylate (121 mg, 0.212 mmol) produced in Reference Example 26 in dichloromethane (5 mL) and acetonitrile (2 mL), and the mixture was stirred at room temperature for 4 hours. The solvent in the reaction solution was distilled off under reduced pressure, and the residue was separated into organic and aqueous layers by the addition of a saturated sodium bicarbonate aqueous solution and ethyl acetate. The obtained organic layer was washed with brine and dried over anhydrous sodium sulfate, and the solvent was distilled off under reduced pressure.

2-Chloro-5-(trifluoromethyl)pyrazine (31.4 µL, 0.254 mmol) and N,N-diisopropylethylamine (54.1 µL, 0.318 mmol) were added to a solution of the obtained residue in DMSO (2 mL), and the mixture was stirred at room temperature for 1 hour and then left overnight as it was. The reaction solution was diluted with ethyl acetate, washed with water and brine in this order, and dried over anhydrous sodium sulfate, and the solvent was distilled off under reduced pressure. The obtained residue was purified by silica gel column chromatography [elute: hexane/ethyl acetate=95/5-50/50 (gradient)] to obtain a synthesis intermediate.

Triethylsilane (0.113 mL, 0.707 mmol) and trifluoroacetic acid (1.35 mL, 17.7 mmol) were added to a solution of the synthesis intermediate obtained by the procedures described above in dichloromethane (2 mL), and the mixture was stirred at room temperature for 1 hour. The solvent in the reaction solution was distilled off, and the residue was separated into organic and aqueous layers by the addition of ethyl acetate and a saturated sodium bicarbonate aqueous solution. The obtained organic layer was washed with brine and dried over anhydrous sodium sulfate, and the solvent was distilled off under reduced pressure. The obtained residue was purified by silica gel column chromatography [elute: ethyl acetate/methanol=100/0-95/5 (gradient)] to obtain the title compound (66 mg, yield: 71%, optically active form).

$[\alpha]_D^{25}$=+13° (DMF, c=1.00)

(Example 19) (+)-cis-5-Hydroxy-4-(trifluoromethyl)-3-{1-[6-(trifluoromethyl)pyridazin-3-yl]piperidin-4-yl}-1,4,5,7-tetrahydro-6H-pyrazolo[3,4-b]pyridin-6-one

[Formula 52]

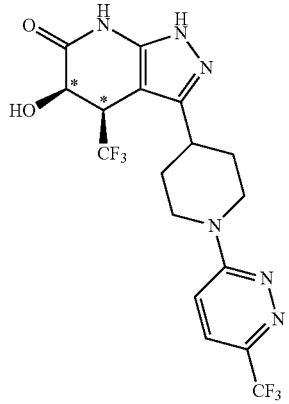

The title compound (70 mg, yield: 69%, optically active form) was obtained through the same reaction as in the method described in Example 18 using 3-chloro-6-(trifluoromethyl)pyridazine (50.6 mg, 0.277 mmol) instead of 2-chloro-5-(trifluoromethyl)pyrazine.

$[\alpha]_D^{25}$=+12° (DMF, c=1.00)

(Example 20) (+)-6-{4-[cis-5-Hydroxy-6-oxo-4-(trifluoromethyl)-4,5,6,7-tetrahydro-1H-pyrazolo[3,4-b]pyridin-3-yl]piperidin-1-yl}-4-(trifluoromethyl)pyridine-3-carbonitrile

[Formula 53]

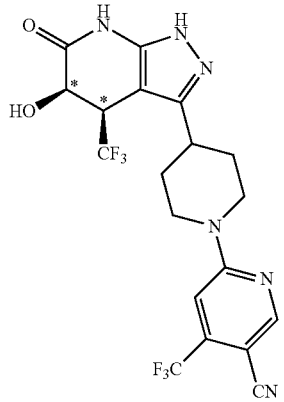

The title compound (56 mg, yield: 68%, optically active form) was obtained through the same reaction as in the method described in Example 18 using 6-chloro-4-(trifluoromethyl)pyridine-3-carbonitrile (43.9 mg, 0.212 mmol) instead of 2-chloro-5-(trifluoromethyl)pyrazine.

$[\alpha]_D^{25}$=+18° (DMF, c=1.00).

(Example 21) (+)-cis-5-Hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one

[Formula 54]

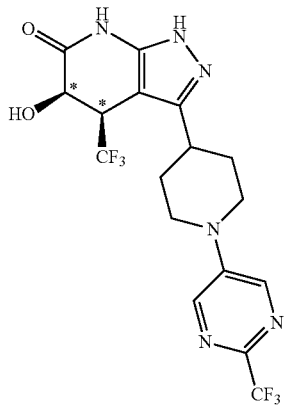

Chlorotrimethylsilane (0.31 mL, 2.5 mmol) and sodium iodide (0.31 g, 2.1 mmol) were added to a mixed solution of tert-butyl (+)-4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidine-1-carboxylate (0.52 g, 0.91 mmol) produced in Reference Example 26 in dichloromethane (25 mL) and acetonitrile (10 mL), and the mixture was stirred at room temperature for 2 hours. The solvent in the reaction solution was distilled off under reduced pressure, and the residue was separated into organic and aqueous layers by the addition of a saturated sodium bicarbonate aqueous solution and ethyl acetate. The obtained organic layer was washed with brine and dried over anhydrous sodium sulfate, and the solvent was distilled off under reduced pressure.

5-Chloro-2-(trifluoromethyl)pyrimidine (0.37 mL, 2.0 mmol) and DBU (0.62 mL, 4.2 mmol) were added to a solution of the obtained residue in DMSO (30 mL), and the mixture was stirred at 70° C. for 18 hours. The reaction solution was diluted with ethyl acetate, washed with water and brine in this order, and dried over anhydrous sodium sulfate, and the solvent was distilled off under reduced pressure. The obtained residue was purified by silica gel column chromatography [elute: hexane/ethyl acetate=95/5-50/50 (gradient)] to obtain a synthesis intermediate.

Triethylsilane (0.200 mL, 1.26 mmol) and trifluoroacetic acid (1.0 mL, 13 mmol) were added to a solution of the synthesis intermediate obtained by the procedures described above in dichloromethane (3 mL), and the mixture was stirred at room temperature for 1 hour. The solvent in the reaction solution was distilled off, and the residue was separated into organic and aqueous layers by the addition of ethyl acetate and a saturated sodium bicarbonate aqueous solution. The obtained organic layer was washed with brine and dried over anhydrous sodium sulfate, and the solvent was distilled off under reduced pressure. The obtained residue was purified by silica gel column chromatography [elute: ethyl acetate/methanol=50/50-0/100 (gradient)] to obtain the title compound (0.11 g, yield: 26%, optically active form).

$[\alpha]_D^{25}$2=+7.2° (DMF, c=1.00)

(Example 22) (+)-cis-3-[1-(5-Chloropyridin-2-yl)piperidin-4-yl]-5-hydroxy-4-(trifluoromethyl)-1,4,5,7-tetrahydro-6H-pyrazolo[3,4-b]pyridin-6-one

[Formula 55]

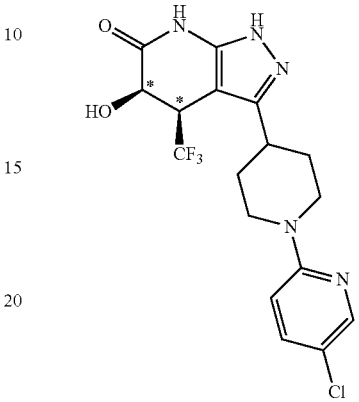

The title compound (39 mg, yield: 44%, optically active form) was obtained through the same reaction as in the method described in Example 21 except that 5-chloro-2-fluoropyridine (55.8 μL, 0.556 mmol) was used instead of 5-chloro-2-(trifluoromethyl)pyrimidine and the mixture was stirred at room temperature for 1 hour and left instead of stirring at 70° C. for 18 hours.

$^1$H-NMR (400 MHz, DMSO-d$_6$) δ: 12.20 (1H, s), 10.53 (1H, s), 8.11 (1H, d, J=3 Hz), 7.58 (1H, dd, J=9 Hz, 3 Hz), 6.91 (1H, d, J=9 Hz), 5.51 (1H, brs), 4.45-4.37 (3H, m), 4.18-4.10 (1H, m), 3.04-2.97 (1H, m), 2.92-2.81 (2H, m), 1.84-1.58 (4H, m);

MS (ESI) m/z: 416 (M+H)$^+$.

$[\alpha]_D^{25}$=+12° (DMF, c=1.01).

(Reference Example 27) Optically active form of cis-1-(diphenylmethyl)-5-hydroxy-3-(piperidin-4-yl)-4-(trifluoromethyl)-1,4,5,7-tetrahydro-6H-pyrazolo[3,4-b]pyridin-6-one

[Formula 56]

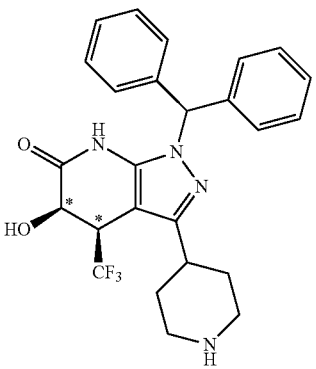

Chlorotrimethylsilane (1.42 mL, 11.2 mmol) and sodium iodide (1.68 g, 11.2 mmol) were added to a mixed solution of tert-butyl (+)-4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidine-1-carboxylate (3.20 g, 5.61 mmol) produced in Reference Example 26 in dichloromethane (100 mL) and acetonitrile (30 mL), and the mixture was stirred at room temperature for 2 hours. To the reaction solution, N-diisopropylethylamine (2.86 mL, 16.8 mmol) and water (15 mL) were added, and the solvent was distilled off under reduced pressure. To the obtained residue, dichloromethane (150 mL) was added, and the mixture was stirred. The precipitate was collected by filtration to obtain the title compound (2.00 g, yield: 76%, optically active form).

$^1$H-NMR (400 MHz, DMSO-$d_6$) δ: 7.41-7.11 (10H, m), 6.80 (1H, s), 5.86 (1H, d, J=4 Hz), 4.60-4.55 (1H, m), 4.16-4.07 (1H, m), 3.33-3.21 (2H, m), 2.99-2.87 (3H, m), 2.03-1.66 (4H, m).

(Reference Example 28) Optically active form of cis-1-(diphenylmethyl)-5-hydroxy-4-(trifluoromethyl)-3-{1-[6-(trifluoromethyl)pyridin-3-yl]piperidin-4-yl}-1,4,5,7-tetrahydro-6H-pyrazolo[3,4-b]pyridin-6-one

[Formula 57]

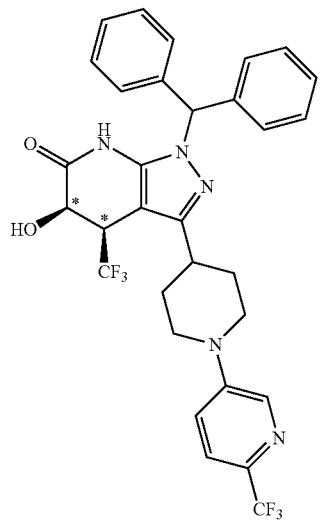

DBU (87.6 μL, 0.587 mmol) and 5-fluoro-2-(trifluoromethyl)pyridine (51.9 μL, 0.440 mmol) were added at room temperature to a suspension of the optically active form of cis-1-(diphenylmethyl)-5-hydroxy-3-(piperidin-4-yl)-4-(trifluoromethyl)-1,4,5,7-tetrahydro-6H-pyrazolo[3,4-b]pyridin-6-one (0.138 g, 0.293 mmol) produced in Reference Example 27 in DMSO (3 mL), and the mixture was stirred at room temperature for 3 hours and then at 60° C. for 8 hours in an oil bath. The reaction solution was brought back to room temperature, then diluted with ethyl acetate, and washed with water and brine in this order. The organic layer was dried over anhydrous sodium sulfate, and the solvent was distilled off under reduced pressure. The obtained residue was purified by silica gel column chromatography [elute: hexane/ethyl acetate=93/7-55/45 (gradient)] to obtain the title compound (0.135 g, yield: 75%, optically active form).

$^1$H-NMR (400 MHz, CDCl$_3$) δ: 8.32 (1H, d, J=3 Hz), 7.90 (1H, s), 7.50 (1H, d, J=9 Hz), 7.39-7.34 (6H, m), 7.19 (1H, dd, J=9 Hz, 3 Hz), 7.15-7.10 (4H, m), 6.66 (1H, s), 4.55 (1H, d, J=7 Hz), 3.96-3.81 (3H, m), 3.72 (1H, s), 3.04-2.97 (2H, m), 2.87-2.79 (1H, m), 2.04-1.85 (4H, m).

(Example 23) (+)-cis-5-Hydroxy-4-(trifluoromethyl)-3-{1-[6-(trifluoromethyl)pyridin-3-yl]piperidin-4-yl}-1,4,5,7-tetrahydro-6H-pyrazolo[3,4-b]pyridin-6-one

[Formula 58]

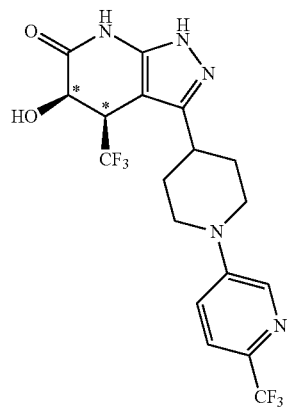

Trifluoroacetic acid (0.8 mL, 10 mmol) was added at room temperature to a solution of the optically active form of cis-1-(diphenylmethyl)-5-hydroxy-4-(trifluoromethyl)-3-{1-[6-(trifluoromethyl)pyridin-3-yl]piperidin-4-yl}-1,4,5,7-tetrahydro-6H-pyrazolo[3,4-b]pyridin-6-one (0.135 g, 0.219 mmol) produced in Reference Example 28 and triethylsilane (0.140 mL, 0.877 mmol) in dichloromethane (4 mL), and the mixture was stirred for 45 minutes. The solvent in the reaction solution was distilled off under reduced pressure, and the obtained residue was separated into organic and aqueous layers by the addition of ethyl acetate and a saturated sodium bicarbonate aqueous solution. The organic layer was washed with brine and dried over anhydrous sodium sulfate, and the solvent was distilled off under reduced pressure. The obtained residue was purified by silica gel column chromatography [elute: hexane/ethyl acetate=83/17-0/100 (gradient)] to obtain the title compound (88.9 mg, yield: 90%, optically active form).

$^1$H-NMR (400 MHz, DMSO-$d_6$) δ: 12.24 (1H, s), 10.54 (1H, s), 8.46 (1H, d, J=3 Hz), 7.64 (1H, d, J=9 Hz), 7.47 (1H, dd, J=9 Hz, 3 Hz), 5.52 (1H, d, J=4 Hz), 4.45 (1H, dd, J=7 Hz, 4 Hz), 4.20-4.05 (3H, m), 3.06-2.91 (3H, m), 1.87-1.73 (4H, m);

MS (ESI) m/z: 450 (M+H)$^+$;

$[α]_D^{25}$=+7.5° (DMF, c=0.958).

67

(Example 24) (+)-3-Fluoro-5-{4-[cis-5-hydroxy-6-oxo-4-(trifluoromethyl)-4,5,6,7-tetrahydro-1H-pyrazolo[3,4-b]pyridin-3-yl]piperidin-1-yl}pyridine-2-carbonitrile

[Formula 59]

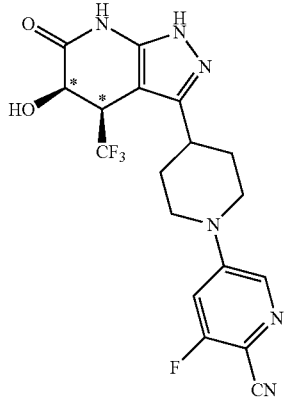

DBU (0.135 mL, 0.901 mmol) and 3,5-difluoropyridine-2-carbonitrile (94.7 g, 0.676 mmol) were added at room temperature to a suspension of the optically active form of cis-1-(diphenylmethyl)-5-hydroxy-3-(piperidin-4-yl)-4-(trifluoromethyl)-1,4,5,7-tetrahydro-6H-pyrazolo[3,4-b]pyridin-6-one (0.212 g, 0.451 mmol) produced in Reference Example 27 in DMSO (2 mL), and the mixture was stirred for 66 hours. The reaction solution was diluted with ethyl acetate and washed with water and brine in this order. The organic layer was dried over anhydrous sodium sulfate, and the solvent was distilled off under reduced pressure. The obtained residue was purified by silica gel column chromatography [elute: hexane/ethyl acetate=93/7-50/50 (gradient)] to obtain a synthesis intermediate.

The title compound (84.8 g, yield: 44%, optically active form) was obtained through the same reaction as in the method described in Example 23 using the synthesis intermediate obtained by the procedures described above instead of the optically active form of cis-1-(diphenylmethyl)-5-hydroxy-4-(trifluoromethyl)-3-{1-[6-(trifluoromethyl)pyridin-3-yl]piperidin-4-yl}-1,4,5,7-tetrahydro-6H-pyrazolo[3,4-b]pyridin-6-one.

$^1$H-NMR (400 MHz, DMSO-$d_6$) δ: 12.20 (1H, s), 10.54 (1H, s), 8.36-8.35 (1H, m), 7.45 (1H, dd, J=14 Hz, 2 Hz), 5.53 (1H, d, J=4 Hz), 4.46-4.43 (1H, m), 4.23-4.11 (3H, m), 3.12-3.04 (3H, m), 1.88-1.65 (4H, m);

MS (ESI) m/z: 425 (M+H)$^+$;

$[α]_D^{25}$=+14° (DMF, c=1.01).

68

(Example 25) (+)-cis-5-Hydroxy-4-(trifluoromethyl)-3-{1-[2-(trifluoromethyl)pyrimidin-4-yl]piperidin-4-yl}-1,4,5,7-tetrahydro-6H-pyrazolo[3,4-b]pyridin-6-one

[Formula 60]

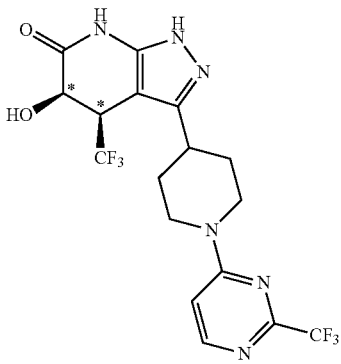

The title compound (0.121 g, yield: 60%, optically active form) was obtained through the same reaction as in the method described in Example 24 using 4-chloro-2-trifluoromethylpyrimidine (0.123 g, 0.676 mmol) instead of 3,5-difluoropyridine-2-carbonitrile.

$^1$H-NMR (400 MHz, DMSO-$d_6$) δ: 12.17 (1H, s), 10.54 (1H, s), 8.34 (1H, d, J=7 Hz), 7.13 (1H, d, J=7 Hz), 5.52 (1H, d, J=4 Hz), 4.74-4.30 (3H, m), 4.21-4.12 (1H, m), 3.16-2.99 (3H, m), 1.91-1.57 (4H, m);

MS (ESI) m/z: 451 (M+H)$^+$;

$[α]_D^{25}$=+12° (DMF, c=1.01).

(Reference Example 29) Optically active form of cis-1-(diphenylmethyl)-5-hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one

[Formula 61]

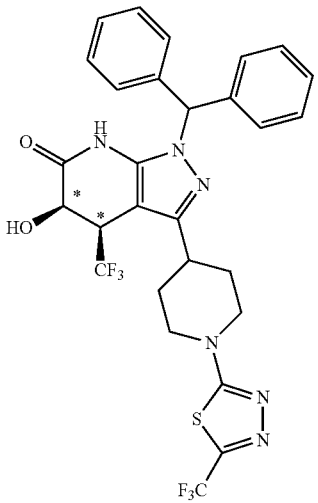

DBU (0.135 mL, 0.901 mmol) and 2-chloro-5-trifluoromethyl-1,3,4-thiadiazole (0.127 g, 0.676 mmol) were added at room temperature to a suspension of the optically active form of cis-1-(diphenylmethyl)-5-hydroxy-3-(piperidin-4-yl)-4-(trifluoromethyl)-1,4,5,7-tetrahydro-6H-pyrazolo[3,4-b]pyridin-6-one (0.212 g, 0.451 mmol) produced in Reference Example 27 in DMSO (1 mL), and the mixture was stirred for 18 hours. The reaction solution was diluted with ethyl acetate and washed with brine three times. The obtained organic layer was dried over anhydrous sodium sulfate, and the solvent was distilled off under reduced pressure. The obtained residue was purified by silica gel column chromatography [elute: hexane/ethyl acetate=95/5-50/50 (gradient)] to obtain the title compound (0.207 g, yield: 74%, optically active form).

$^1$H-NMR (400 MHz, CDCl$_3$) δ: 7.40-7.37 (6H, m), 7.13-7.06 (5H, m), 6.68 (1H, s), 4.53 (1H, d, J=7 Hz), 4.08-4.00 (2H, m), 3.93-3.85 (1H, m), 3.69 (1H, d, J=3 Hz), 3.39-3.32 (2H, m), 2.92-2.85 (1H, m), 2.04-1.88 (4H, m).

(Example 26) (+)-cis-5-Hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one

[Formula 62]

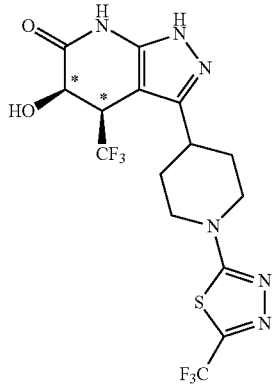

Trifluoroacetic acid (0.8 mL, 10 mmol) was added at room temperature to a solution of the optically active form of cis-1-(diphenylmethyl)-5-hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one (0.196 g, 0.315 mmol) produced in Reference Example 29 and triethylsilane (0.201 mL, 1.26 mmol) in dichloromethane (4 mL), and the mixture was stirred for 45 minutes. The solvent in the reaction solution was distilled off under reduced pressure, and the obtained residue was separated into organic and aqueous layers by the addition of ethyl acetate and a saturated sodium bicarbonate aqueous solution. The organic layer was washed with brine and dried over anhydrous sodium sulfate, and the solvent was distilled off under reduced pressure. The obtained residue was purified by silica gel column chromatography [elute: hexane/ethyl acetate=80/20-0/100 (gradient)] to obtain the title compound (0.109 g, yield: 76%, optically active form).

$^1$H-NMR (400 MHz, DMSO-d$_6$) δ: 12.25 (1H, s), 10.56 (1H, s), 5.54 (1H, brs), 4.45 (1H, d, J=7 Hz), 4.21-4.12 (1H, m), 4.09-4.01 (2H, m), 3.42-3.35 (2H, m), 3.14-3.06 (1H, m), 1.93-1.76 (4H, m);

MS (ESI) m/z: 457 (M+H)$^+$;

$[α]_D^{25}$=+8.7° (DMF, c=1.01)

(Reference Example 30) Optically active form of 5-{4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidin-1-yl}-3-methylpyridine-2-carbonitrile

[Formula 63]

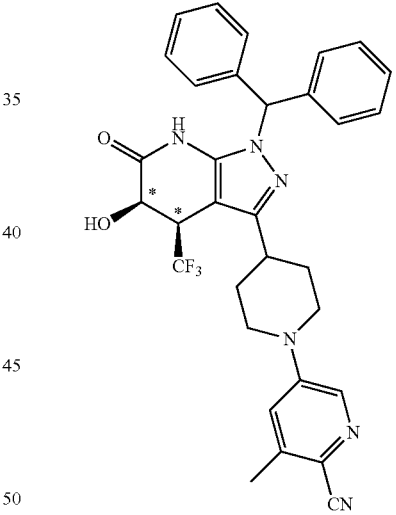

Cesium carbonate (0.734 g, 2.25 mmol) and 5-chloro-3-methylpyridine-2-carbonitrile (0.206 g, 1.35 mmol) were added at room temperature to a suspension of the optically active form of cis-1-(diphenylmethyl)-5-hydroxy-3-(piperidin-4-yl)-4-(trifluoromethyl)-1,4,5,7-tetrahydro-6H-pyrazolo[3,4-b]pyridin-6-one (0.212 g, 0.451 mmol) produced in Reference Example 27 in DMSO (2 mL), and the mixture was stirred at 150° C. for 2 hours. The reaction suspension was cooled to room temperature, then diluted with ethyl acetate, and washed with brine. The obtained organic layer was dried over anhydrous sodium sulfate, and the solvent was distilled off under reduced pressure. The obtained residue was purified by silica gel column chromatography [elute: hexane/ethyl acetate=92/8-50/50 (gradient)] to obtain the title compound (0.226 g, yield: 86%, optically active form).

¹H-NMR (400 MHz, CDCl₃) δ: 8.14 (1H, d, J=3 Hz), 7.40-7.36 (6H, m), 7.12-7.06 (5H, m), 6.91 (1H, d, J=3 Hz), 6.69 (1H, s), 4.53 (1H, d, J=7 Hz), 3.94-3.86 (3H, m), 3.69 (1H, d, J=3 Hz), 3.08-3.00 (2H, m), 2.89-2.81 (1H, m), 2.45 (3H, s), 2.02-1.80 (4H, m).

(Example 27) (+)-5-{4-[cis-5-Hydroxy-6-oxo-4-(trifluoromethyl)-4,5,6,7-tetrahydro-1H-pyrazolo[3,4-b]pyridin-3-yl]piperidin-1-yl}-3-methylpyridine-2-carbonitrile

[Formula 64]

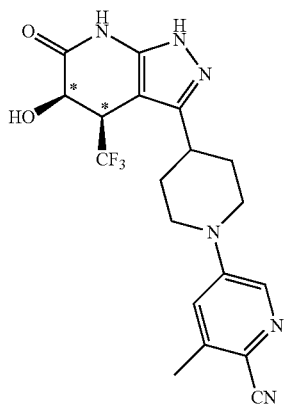

The title compound (0.115 g, yield: 73%, optically active form) was obtained through the same reaction as in the method described in Example 26 using the optically active form of 5-{4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidin-1-yl}-3-methylpyridine-2-carbonitrile (0.221 g, 0.377 mmol) produced in Reference Example 30 instead of cis-1-(diphenylmethyl)-5-hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one.

¹H-NMR (400 MHz, DMSO-d₆) δ: 12.21 (1H, s), 10.53 (1H, s), 8.30 (1H, d, J=3 Hz), 7.33 (1H, d, J=3 Hz), 5.52 (1H, d, J=4 Hz), 4.45-4.43 (1H, m), 4.17-4.11 (3H, m), 3.07-2.94 (3H, m), 2.39 (3H, s), 1.87-1.65 (4H, m);

MS (ESI) m/z: 421 (M+H)⁺;

$[\alpha]_D^{25}$=+12° (DMF, c=0.984).

(Reference Example 31) Optically active form of 5-{4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidin-1-yl}pyrazine-2-carbonitrile

[Formula 65]

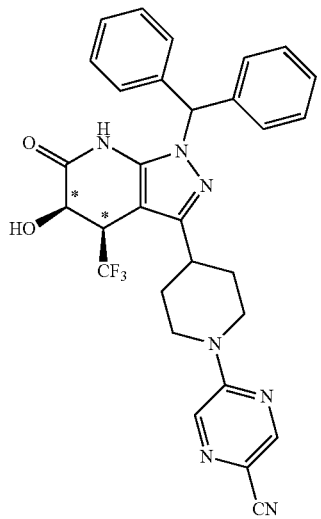

The title compound (132 mg, yield: 66%, optically active form) was obtained through the same reaction as in the method described in Reference Example 28 using 5-chloro-2-cyanopyrazine (73.4 mg, 0.526 mmol) instead of 5-fluoro-2-(trifluoromethyl)pyridine.

¹H-NMR (400 MHz, CDCl₃) δ: 8.31 (1H, s), 8.12 (1H, s), 7.40-7.36 (6H, m), 7.12-7.06 (4H, m), 6.67 (1H, s), 4.54 (1H, d, J=7 Hz), 4.50-4.45 (2H, m), 3.95-3.86 (1H, m), 3.70 (1H, s), 3.24-3.16 (2H, m), 2.94 (1H, tt, J=11 Hz, 4 Hz), 2.04-1.74 (4H, m).

(Example 28) (+)-5-{4-[cis-5-Hydroxy-6-oxo-4-(trifluoromethyl)-4,5,6,7-tetrahydro-1H-pyrazolo[3,4-b]pyridin-3-yl]piperidin-1-yl}pyrazine-2-carbonitrile

[Formula 66]

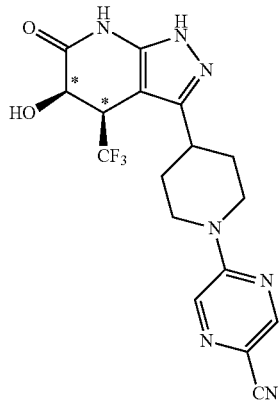

The title compound (78 mg, yield: 86%, optically active form) was obtained through the same reaction as in the method described in Example 26 using the optically active form of 5-{4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidin-1-yl}pyrazine-2-carbonitrile (128 mg, 0.223 mmol) produced in Reference Example 31 instead of cis-1-(diphenylmethyl)-5-hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.18 (1H, s), 10.54 (1H, s), 8.58 (1H, s), 8.50 (1H, s), 5.53 (1H, brs), 4.68-4.61 (2H, m), 4.45-4.42 (1H, m), 4.20-4.11 (1H, m), 3.14-3.05 (3H, m), 1.92-1.61 (4H, m);

MS (ESI) m/z: 408 (M+H)$^+$;

$[\alpha]_D^{25}$=+17° (DMF, c=1.00).

(Example 29) Optically active form of cis-5-hydroxy-3-[1-(6-phenylpyridazin-3-yl)piperidin-4-yl]-4-(trifluoromethyl)-1,4,5,7-tetrahydro-6H-pyrazolo[3,4-b]pyridin-6-one

[Formula 67]

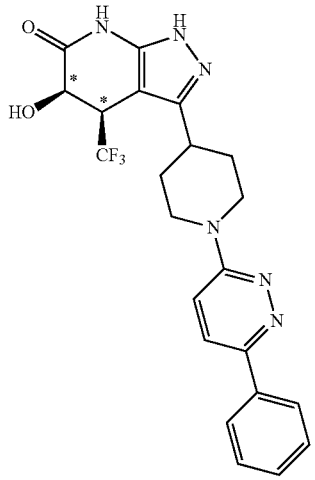

A synthesis intermediate was obtained through the same reaction as in the method described in Reference Example 28 using 3-chloro-6-phenylpyridazine (0.167 g, 0.876 mmol) instead of 5-fluoro-2-(trifluoromethyl)pyridine.

The title compound (29 mg, yield: 14%, optically active form) was obtained through the same reaction as in the method described in Example 26 using the synthesis intermediate obtained by the procedures described above instead of cis-1-(diphenylmethyl)-5-hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.22 (1H, s), 10.54 (1H, s), 8.05-7.94 (3H, m), 7.51-7.40 (4H, m), 5.52 (1H, d, J=4 Hz), 4.64-4.57 (2H, m), 4.47-4.44 (1H, m), 4.22-4.13 (1H, m), 3.53-3.51 (4H, m), 3.08-2.98 (3H, m);

MS (ESI) m/z: 459 (M+H)$^+$.

(Example 30) (+)-cis-5-Hydroxy-4-(trifluoromethyl)-3-{1-[6-(trifluoromethyl)pyrimidin-4-yl]piperidin-4-yl}-1,4,5,7-tetrahydro-6H-pyrazolo[3,4-b]pyridin-6-one

[Formula 68]

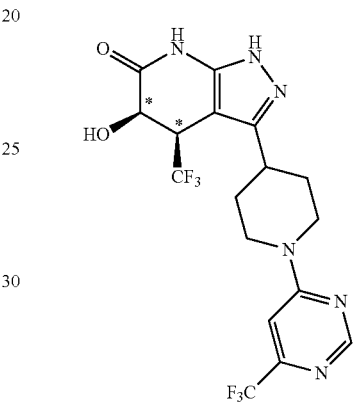

Cesium carbonate (0.582 g, 1.79 mmol) and 4-chloro-6-(trifluoromethyl)pyrimidine (0.163 g, 0.893 mmol) were added at room temperature to a suspension of the optically active form of cis-1-(diphenylmethyl)-5-hydroxy-3-(piperidin-4-yl)-4-(trifluoromethyl)-1,4,5,7-tetrahydro-6H-pyrazolo[3,4-b]pyridin-6-one (210 mg, 0.446 mmol) produced in Reference Example 27 in DMSO (5 mL), and the mixture was stirred at 80° C. for 8 hours. To the reaction solution, water was added, followed by extraction with ethyl acetate three times. The obtained organic layer was washed with brine and dried over anhydrous sodium sulfate, and the solvent was distilled off under reduced pressure. The obtained residue was purified by silica gel column chromatography [elute: hexane/ethyl acetate=100/0-60/40 (gradient)] to obtain a synthesis intermediate.

Trifluoroacetic acid (2 mL, 26.1 mmol) was added at room temperature to a solution of the synthesis intermediate obtained by the procedures described above and triethylsilane (0.116 mL, 0.727 mmol) in dichloromethane (2 mL), and the mixture was stirred for 7.5 hours. The solvent in the reaction solution was distilled off under reduced pressure, and ethyl acetate was added to the obtained residue. The organic layer was washed with a saturated sodium bicarbonate aqueous solution, water, and brine in this order and dried over anhydrous sodium sulfate, and the solvent was distilled off under reduced pressure. The obtained residue was purified by preparative silica gel thin-layer chromatography [elute: dichloromethane/methanol=10/1] to obtain the title compound (48 mg, yield: 24%, optically active form).

$^1$H-NMR (400 MHz, DMSO-$d_6$) δ: 12.17 (1H, s), 10.55 (1H, s), 8.64 (1H, s), 7.34 (1H, s), 5.54 (1H, d, J=4 Hz), 4.46-4.43 (1H, m), 4.21-4.12 (1H, m), 3.13-2.97 (3H, m), 1.91-1.58 (4H, m);

MS (ESI) m/z: 451 (M+H)$^+$;

$[α]_D^{25}$=+10° (DMF, c=1.02).

(Reference Example 32) Optically active form of 5-{4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidin-1-yl}pyridine-3-carbonitrile

[Formula 69]

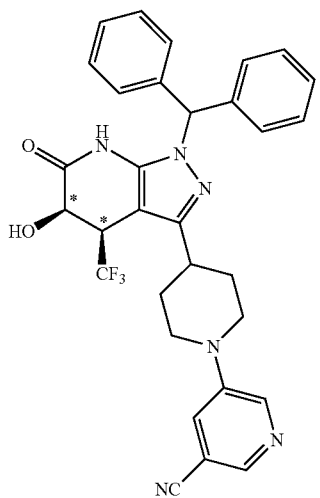

The title compound (42.7 g, yield: 70%, optically active form) was obtained through reaction at 80° C. for 1 hour and then at 100° C. for 5 hours by the method described in Reference Example 30 using 5-fluoropyridine-3-carbonitrile (26.0 mg, 0.213 mmol) instead of 5-chloro-3-methylpyridine-2-carbonitrile.

$^1$H-NMR (400 MHz, CDCl$_3$) δ: 8.46 (1H, d, J=3 Hz), 8.25 (1H, d, J=2 Hz), 7.43-7.04 (10H, m), 6.91 (1H, s), 6.71 (1H, s), 4.56-4.51 (1H, m), 3.96-3.86 (1H, m), 3.83-3.73 (2H, m), 3.72-3.67 (1H, m), 3.02-2.93 (2H, m), 2.87-2.76 (1H, m), 2.08-1.85 (4H, m).

(Example 31) (+)-5-{4-[cis-5-Hydroxy-6-oxo-4-(trifluoromethyl)-4,5,6,7-tetrahydro-1H-pyrazolo[3,4-b]pyridin-3-yl]piperidin-1-yl}pyridine-3-carbonitrile

[Formula 70]

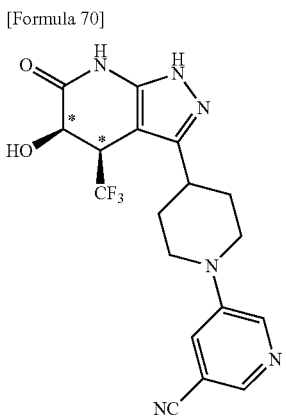 [SMILES: O=C1Nc2[nH]nc(C3CCN(c4cncc(C(F)(F)F)c4)CC3)c2[C@@H](C(F)(F)F)[C@H]1O]

The title compound (0.134 g, yield: 85%, optically active form) was obtained through the same reaction as in the method described in Example 26 using the optically active form of 5-{4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidin-1-yl}pyridine-3-carbonitrile (0.222 g, 0.388 mmol) produced in Reference Example 32 instead of cis-1-(diphenylmethyl)-5-hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one.

$^1$H-NMR (400 MHz, DMSO-$d_6$) δ: 12.24 (1H, s), 10.54 (1H, s), 8.62 (1H, d, J=3 Hz), 8.31 (1H, d, J=2 Hz), 7.81 (1H, dd, J=3 Hz, 2 Hz), 5.65-5.34 (1H, m), 4.48-4.38 (1H, m), 4.21-4.09 (1H, m), 4.07-3.92 (2H, m), 3.06-2.78 (3H, m), 1.90-1.63 (4H, m);

MS (ESI) m/z: 407 (M+H)$^+$;

$[α]_D^{25}$=+9.3° (DMF, c=1.01).

(Reference Example 33) Benzyl 2-chloro-5-(trifluoromethyl)pyridine-4-carboxylate

[Formula 71]

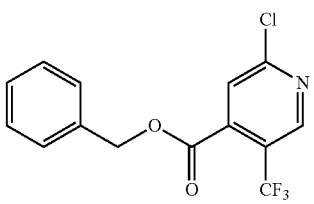

Benzyl bromide (0.634 mL, 3.86 mmol) was added under ice cooling to a solution of 2-chloro-5-(trifluoromethyl)pyridine-4-carboxylic acid (0.870 g, 3.86 mmol) and potassium carbonate (0.640 g, 4.63 mmol) in DMF (10 mL), and the mixture was stirred at the same temperature as above for 10 minutes and then at room temperature for 3 days. To the reaction solution, an ice-cold saturated sodium bicarbonate aqueous solution was added, followed by extraction with ethyl acetate twice. The obtained organic layer was washed with water and dried over anhydrous sodium sulfate, and the solvent was distilled off under reduced pressure. The obtained residue was purified by silica gel column chromatography [elute: hexane:ethyl acetate=100/0-90/10 (gradient)] to obtain the title compound (1.22 g, yield: quantitative).

$^1$H-NMR (400 MHz, CDCl$_3$) δ: 8.78 (1H, s), 7.68 (1H, s), 7.46-7.36 (5H, m), 5.39 (2H, s).

(Reference Example 34) Benzyl 2-{4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidin-1-yl}-5-(trifluoromethyl)pyridine-4-carboxylate

[Formula 72]

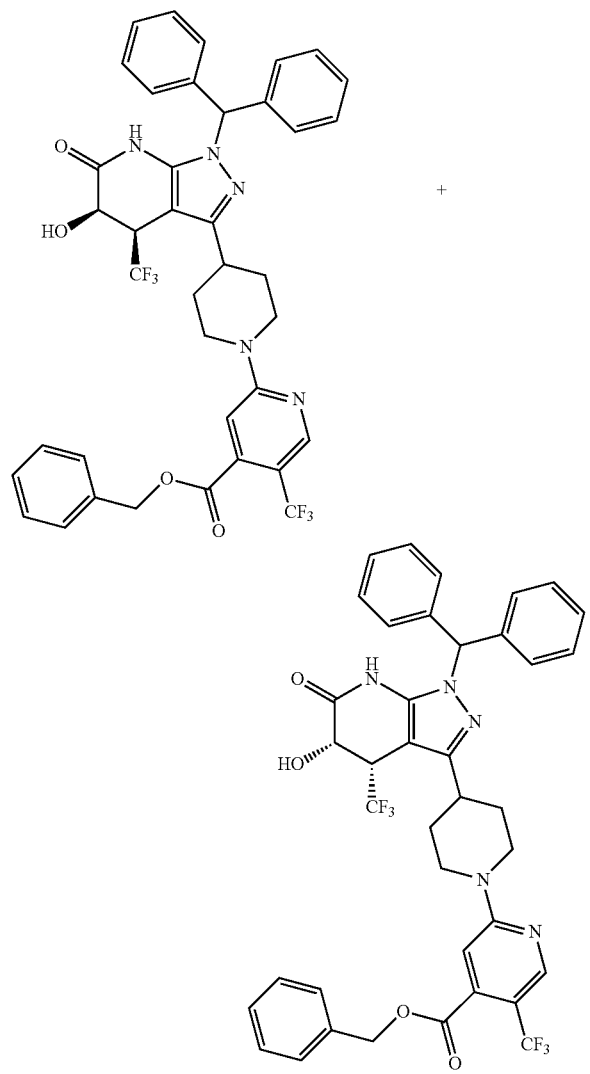

The title compound (1.06 g, yield: 73%) was obtained through the same reaction as in the method described in Reference Example 17 using benzyl 2-chloro-5-(trifluoromethyl)pyridine-4-carboxylate (0.913 g, 2.83 mmol) produced in Reference Example 33 instead of 3-chloro-6-(trifluoromethyl)pyridazine.

$^1$H-NMR (400 MHz, CDCl$_3$) δ: 8.43 (1H, s), 7.44-7.33 (11H, m), 7.11-7.06 (5H, m), 6.86 (1H, s), 6.68 (1H, s), 5.34 (2H, s), 4.54-4.51 (1H, m), 4.47-4.41 (2H, m), 3.94-3.86 (1H, m), 3.69 (1H, d, J=3 Hz), 3.12-3.05 (2H, m), 2.89 (1H, tt, J=11 Hz, 4 Hz), 2.01-1.69 (4H, m).

(Reference Example 35) Optically active form of benzyl 2-{4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidin-1-yl}-5-(trifluoromethyl)pyridine-4-carboxylate

[Formula 73]

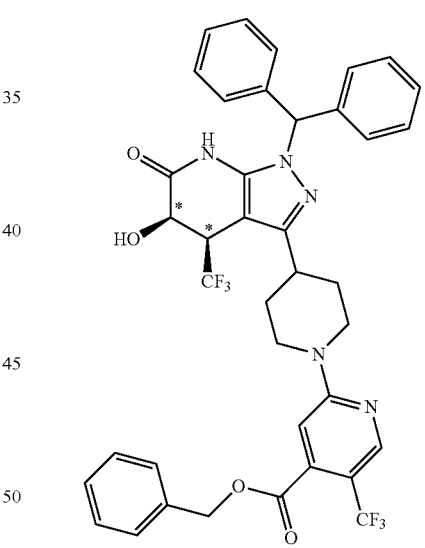

A mixed solution of benzyl 2-{4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidin-1-yl}-5-(trifluoromethyl)pyridine-4-carboxylate (250 mg, 0.333 mmol) produced in Reference Example 34 in hexane (4 mL) and IPA (2 mL) was purified by HPLC [column: Chiralpak IA (20 mm i.d.×250 mm); manufactured by Daicel Corporation, elute: hexane/IPA=70/30, flow rate: 18 mL/min] to obtain the title compound (100 mg, yield: 40%, optically active form).

The optical purity was measured using HPLC [column: Chiralpak IA (4.6 mm i.d.×150 mm); manufactured by Daicel Corporation, elute: hexane/IPA=70/30, flow rate: 1.0 mL/min].

Optical purity: 99% (retention time: 4.4 min).

(Example 32) Benzyl (+)-2-{4-[cis-5-hydroxy-6-oxo-4-(trifluoromethyl)-4,5,6,7-tetrahydro-1H-pyrazolo[3,4-b]pyridin-3-yl]piperidin-1-yl}-5-(trifluoromethyl)pyridine-4-carboxylate

[Formula 74]

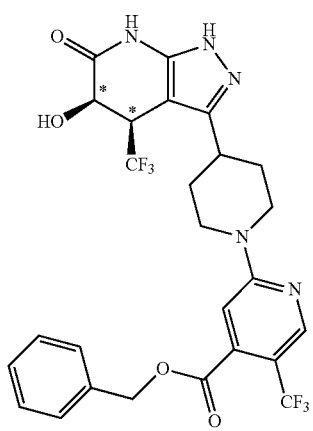

The title compound (60.2 mg, yield: 77%, optically active form) was obtained through the same reaction as in the method described in Example 26 using the optically active form of benzyl 2-{4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidin-1-yl}-5-(trifluoromethyl)pyridine-4-carboxylate (100 mg, 0.133 mmol, optically active form) produced in Reference Example 35 instead of cis-1-(diphenylmethyl)-5-hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one, followed by purification by preparative silica gel thin-layer chromatography [elute: dichloromethane/methanol=10/1].

$^1$H-NMR (400 MHz, DMSO-d$_6$) δ: 12.16 (1H, s), 10.53 (1H, s), 8.49 (1H, s), 7.46-7.34 (5H, m), 7.20 (1H, s), 5.52 (1H, d, J=4 Hz), 5.34 (2H, s), 4.63-4.56 (2H, m), 4.45-4.42 (1H, m), 4.20-4.11 (1H, m), 3.13-2.99 (3H, m), 1.87-1.57 (4H, m);

MS (ESI) m/z: 584 (M+H);

$[α]_D^{25}$=+12° (DMF, c=1.01).

(Reference Example 36) Benzyl 2-{4-[cis-5-{[tert-butyl(dimethyl)silyl]oxy}-1-(diphenylmethyl)-6-oxo-4-(trifluoromethyl)-4,5,6,7-tetrahydro-1H-pyrazolo[3,4-b]pyridin-3-yl]piperidin-1-yl}-5-(trifluoromethyl)pyridine-4-carboxylate

[Formula 75]

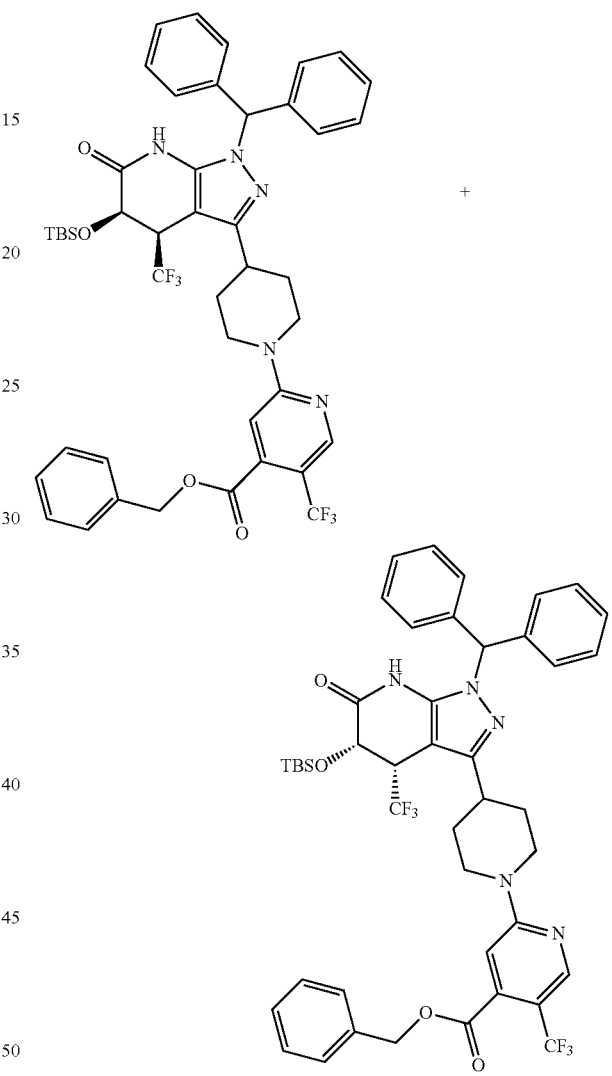

tert-Butyldimethylchlorosilane (0.404 g, 2.68 mmol) and imidazole (0.243 g, 3.57 mmol) were added to a solution of benzyl 2-{4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidin-1-yl}-5-(trifluoromethyl)pyridine-4-carboxylate (670 mg, 0.894 mmol) produced in Reference Example 34 in DMF (5 mL), and the mixture was stirred overnight at room temperature. To the reaction solution, water was added, followed by extraction with ethyl acetate twice. The obtained organic layer was dried over anhydrous sodium sulfate, and the solvent was distilled off under reduced pressure. The obtained residue was purified by silica gel column chromatography [elute: hexane/ethyl acetate=100/0-85/15 (gradient)] to obtain the title compound (673 mg, yield: 87%).

¹H-NMR (400 MHz, CDCl₃) δ: 8.43 (1H, s), 7.74 (1H, brs), 7.45-7.32 (11H, m), 7.19-7.16 (2H, m), 7.13-7.10 (2H, m), 6.87 (1H, s), 6.62 (1H, s), 5.35 (2H, s), 4.59 (1H, d, J=7 Hz), 4.49-4.38 (2H, m), 3.68-3.60 (1H, m), 3.14-3.04 (2H, m), 2.86 (1H, tt, J=11 Hz, 4 Hz), 1.99-1.72 (4H, m), 0.91 (9H, s), 0.14 (3H, s), 0.08 (3H, s).

(Reference Example 37) cis-1-(Diphenylmethyl)-5-hydroxy-3-{1-[4-(piperidin-1-ylcarbonyl)-5-(trifluoromethyl)pyridin-2-yl]piperidin-4-yl}-4-(trifluoromethyl)-1,4,5,7-tetrahydro-6H-pyrazolo[3,4-b]pyridin-6-one

[Formula 76]

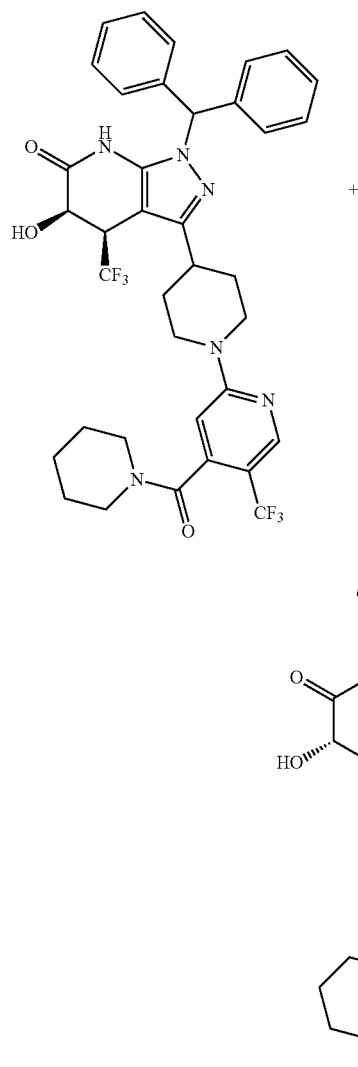

10% palladium-active carbon (300 mg) was added to a solution of benzyl 2-{4-[cis-5-{[tert-butyl(dimethyl)silyl]oxy}-1-(diphenylmethyl)-6-oxo-4-(trifluoromethyl)-4,5,6,7-tetrahydro-1H-pyrazolo[3,4-b]pyridin-3-yl]piperidin-1-yl}-5-(trifluoromethyl)pyridine-4-carboxylate (670 mg, 0.775 mmol) produced in Reference Example 36 in ethyl acetate (20 mL), and the mixture was stirred at room temperature for 5 hours under the hydrogen atmosphere. After filtration through Celite, the solvent was distilled off under reduced pressure to obtain a crude product (600 mg).

Piperidine (35.5 μL, 0.388 mmol), 0-(7-azabenzotriazol-1-yl)-N,N,N',N'-tetramethyluronium hexafluorophosphate (0.147 g, 0.388 mmol), and N,N-diisopropylethylamine (0.133 mL, 0.775 mmol) were added at room temperature to a solution of a portion (150 mg) of the crude product obtained by the procedures described above in DMF (3 mL), and the mixture was stirred overnight at room temperature. To the reaction solution, water was added, followed by extraction with ethyl acetate three times. The obtained organic layer was dried over anhydrous sodium sulfate, and the solvent was distilled off under reduced pressure. The obtained residue was purified by preparative silica gel thin-layer chromatography [elute: hexane/ethyl acetate=2/3] to obtain the title compound (79 mg, yield: 56%).

¹H-NMR (400 MHz, CDCl₃) δ: 8.37 (1H, s), 7.44 (1H, d, J=25 Hz. 4 Hz), 7.37-7.32 (6H, m), 7.11-7.06 (4H, m), 6.67 (1H, s), 6.40 (1H, d, J=4 Hz), 4.50 (1H, d, J=7 Hz), 4.45-4.32 (2H, m), 3.92-3.84 (1H, m), 3.77-3.59 (3H, m), 3.16-3.14 (2H, m), 3.09-2.99 (2H, m), 2.89-2.82 (1H, m), 1.98-1.37 (10H, m).

(Example 33) cis-5-Hydroxy-3-{1-[4-(piperidin-1-ylcarbonyl)-5-(trifluoromethyl)pyridin-2-yl]piperidin-4-yl}-4-(trifluoromethyl)-1,4,5,7-tetrahydro-6H-pyrazolo[3,4-b]pyridin-6-one

[Formula 77]

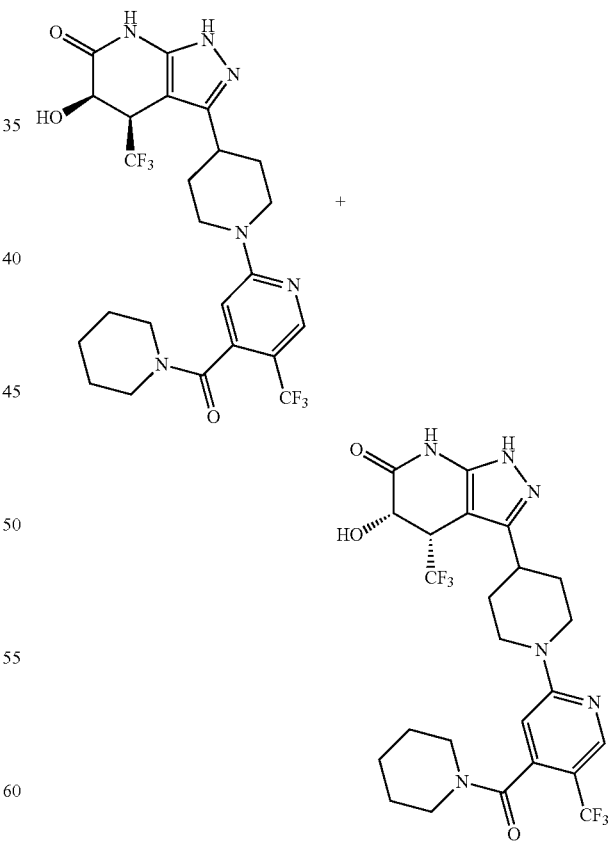

The title compound (44 mg, yield: 51%) was obtained through the same reaction as in the method described in Example 32 using cis-1-(diphenylmethyl)-5-hydroxy-3-{1-[4-(piperidin-1-ylcarbonyl)-5-(trifluoromethyl)pyridin-2-yl]

piperidin-4-yl}-4-(trifluoromethyl)-1,4,5,7-tetrahydro-6H-pyrazolo[3,4-b]pyridin-6-one (112 mg, 0.154 mmol) produced in Reference Example 37 instead of the optically active form of benzyl 2-{4-[cis-1-(diphenylmethyl)-5-hydroxy-6-oxo-4-(trifluoromethyl)-4,5,6,7-tetrahydro-1H-pyrazolo[3,4-b]pyridin-3-yl]piperidin-1-yl}-5-(trifluoromethyl)pyridine-4-carboxylate.

$^1$H-NMR (400 MHz, CDCl$_3$) δ: 10.72 (1H, brs), 8.44 (1H, s), 6.51 (1H, s), 4.74-4.69 (1H, m), 4.55 (1H, d, J=7 Hz), 4.44-4.38 (1H, m), 4.16-4.07 (1H, m), 3.97-3.89 (1H, m), 3.78-3.73 (1H, m), 3.63-3.56 (1H, m), 3.21-3.17 (2H, m), 3.13-2.94 (3H, m), 2.01-1.42 (10H, m);

MS (ESI) m/z: 561 (M+H)$^+$.

(Reference Example 38) tert-Butyl 4-[4,5-dihydroxy-6-oxo-4-(trifluoromethyl)-4,5,6,7-tetrahydro-1H-pyrazolo[3,4-b]pyridin-3-yl]piperidine-1-carboxylate

[Formula 78]

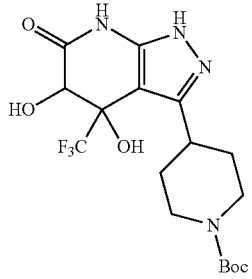

A solution of ethyl 2-triethylsilyloxyacetate (compound described in the literature J. Org. Chem., 2008, Vol. 73, p. 6268-6278, 18.37 g, 84.13 mmol) and ethanol (0.1474 mL, 2.524 mmol) in toluene (40 mL) was added at room temperature to a suspension of sodium hydride (63% dispersion in oil, 5.127 g, 134.6 mmol) in toluene (80 mL), subsequently a solution of ethyl trifluoroacetate (15.07 mL, 126.2 mmol) in toluene (20 mL) was added thereto, and the mixture was stirred for 5 minutes and then stirred at 80° C. for 30 minutes. To the reaction solution, a saturated ammonium chloride aqueous solution was added under ice cooling, followed by extraction with ethyl acetate. The obtained organic layer was washed with brine and dried over anhydrous sodium sulfate, and the solvent was distilled off under reduced pressure to obtain a crude oil product (23.6 g).

A mixed solution of the crude oil product (23.6 g) obtained by the procedures described above and tert-butyl 4-[5-amino-1-(diphenylmethyl)-1H-pyrazol-3-yl]piperidine-1-carboxylate (10.83 g, 25.04 mmol) produced in Reference Example 12 in ethanol (150 mL) and acetic acid (50 mL) was stirred for 4 hours under heating to reflux. The solvent in the reaction solution was distilled off under reduced pressure, and ethyl acetate was added to the obtained residue. The organic layer was washed with a saturated sodium bicarbonate aqueous solution and brine in this order and dried over anhydrous sodium sulfate, and the solvent was distilled off under reduced pressure. Ethyl acetate and hexane were added to the obtained residue, and the resulting precipitate was collected by filtration to obtain a solid. The solvent in the filtrate was further distilled off under reduced pressure. The obtained residue was purified by silica gel column chromatography [elute: hexane/ethyl acetate=90/10-50/50 (gradient)] and combined with the preliminarily obtained solid to obtain a synthesis intermediate.

Triethylsilane (10.7 mL, 67.4 mmol) and trifluoroacetic acid (90 mL, 1176 mmol) were added to a suspension of the synthesis intermediate obtained by the procedures described above in dichloromethane (300 mL), and the mixture was stirred at room temperature for 2 hours. The solvent in the reaction solution was distilled off under reduced pressure. To the obtained residue, diethyl ether and hexane were added, and the mixture was stirred for 30 minutes. The resulting precipitate was collected by filtration to obtain a colorless solid.

A solution of di-t-butyl dicarbonate (5.53 g, 25.4 mmol) and triethylamine (4.69 mL, 33.8 mmol) in ethyl acetate (30 mL) was added at room temperature to a mixed suspension of the colorless solid obtained by the procedures described above in ethyl acetate (120 mL) and THF (40 mL), and the mixture was stirred at room temperature for 3 hours and left overnight at room temperature as it was. The reaction solution was washed with a saturated sodium bicarbonate aqueous solution and brine in this order and dried over anhydrous sodium sulfate, and the solvent was distilled off under reduced pressure. The obtained residue was purified by silica gel column chromatography [elute: hexane/ethyl acetate=50:50-0:100 (gradient)] to obtain the title compound (3.09 g, yield: 44%).

$^1$H-NMR (400 MHz, DMSO-d$_6$) δ: 12.24 (1H, s), 10.55 (1H, s), 6.76 (1H, s), 5.65 (1H, d, J=4 Hz), 4.33 (1H, brs), 4.13-3.99 (2H, m), 3.20-3.09 (1H, m), 2.84-2.59 (2H, m), 1.84-1.76 (1H, m), 1.66-1.46 (3H, m), 1.42 (9H, s).

(Reference Example 39) Optically active form of tert-butyl 4-[4,5-dihydroxy-6-oxo-4-(trifluoromethyl)-4,5,6,7-tetrahydro-1H-pyrazolo[3,4-b]pyridin-3-yl]piperidine-1-carboxylate

[Formula 79]

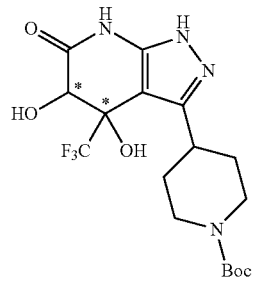

A mixed solution of tert-butyl 4-[4,5-dihydroxy-6-oxo-4-(trifluoromethyl)-4,5,6,7-tetrahydro-1H-pyrazolo[3,4-b]pyridin-3-yl]piperidine-1-carboxylate (0.79 g, 1.9 mmol) produced in Reference Example 38 in ethyl acetate and methanol was adsorbed onto a silica gel, and the solvent was distilled off under reduced pressure. The obtained powder was purified by flash LC [column: Chiralflash IA (30 mm i.d.×100 mm); manufactured by Daicel Corporation, elute: hexane/IPA=90/10, flow rate: 12 mL/min] to obtain the title compound (0.34 g, yield: 43%, optically active form).

(Example 34) (+)-4,5-Dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one

[Formula 80]

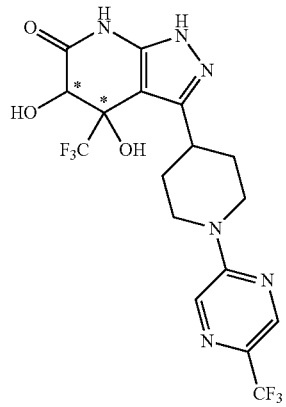

Trifluoroacetic acid (2 mL) was added at room temperature to a suspension of the optically active form of tert-butyl 4-[4,5-dihydroxy-6-oxo-4-(trifluoromethyl)-4,5,6,7-tetrahydro-1H-pyrazolo[3,4-b]pyridin-3-yl]piperidine-1-carboxylate (0.34 g, 0.81 mmol) produced in Reference Example 39 in dichloromethane (6 mL), and the mixture was stirred for 2 hours. The solvent in the reaction solution was distilled off under reduced pressure, and the obtained residue was solidified by the addition of diethyl ether and hexane. The solvent was removed by decantation, and the obtained solid was dried under reduced pressure to obtain a synthesis intermediate.

2-Chloro-5-(trifluoromethyl)pyrazine (0.15 mL, 1.2 mmol) and N,N-diisopropylethylamine (0.41 mL, 2.4 mmol) were added at room temperature to a solution of the synthesis intermediate obtained by the procedures described above in DMSO (5 mL), and the mixture was stirred for 1 hour and then left overnight as it was. To the reaction solution, ethyl acetate was added. The organic layer was washed with water and brine in this order and dried over anhydrous sodium sulfate, and the solvent was distilled off under reduced pressure. The obtained residue was purified by silica gel column chromatography [elute: hexane/ethyl acetate=50/50-0/1000 (gradient)] to obtain the title compound (0.31 g, yield: 82%, optically active form).

The optical purity was measured using HPLC [column: Chiralpak IA (4.6 mm i.d.×250 mm); manufactured by Daicel Corporation, elute: hexane/IPA=60/40, flow rate: 1.0 mL/min].

Optical purity: 99% or higher (retention time: 6.7 min);
$^1$H-NMR (400 MHz, DMSO-$d_6$) δ: 12.21 (1H, s), 10.57 (1H, s), 8.51 (1H, s), 8.50 (1H, s), 6.81 (1H, s), 5.68 (1H, d, J=4 Hz), 4.69-4.56 (2H, m), 4.37-4.31 (1H, m), 3.46-3.34 (1H, m), 3.11-2.97 (2H, m), 1.98-1.88 (1H, m), 1.83-1.58 (3H, m);

MS (ESI) m/z: 467 (M+H)$^+$;
$[α]_D^{25}$=+3.9° (DMF, c=0.924).

(Example 35) (+)-4,5-Dihydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one

[Formula 81]

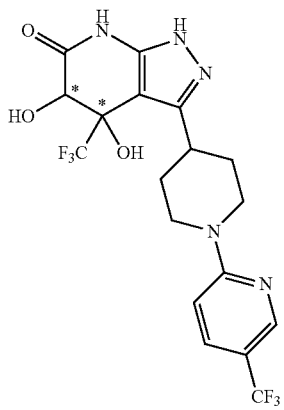

The title compound (890 mg, yield: 89%, optically active form) was obtained through the same reaction as in the method described in Example 34 using 2-fluoro-5-(trifluoromethyl)pyridine (0.468 mL, 3.89 mmol) instead of 2-chloro-5-(trifluoromethyl)pyrazine.

The optical purity was measured using HPLC [column: Chiralpak IA (4.6 mm i.d.×250 mm); manufactured by Daicel Corporation, elute: hexane/IPA=60/40, flow rate: 1.0 mL/min].

Optical purity: 99% or higher (retention time: 6.8 min);
$[α]_D^{25}$=+4.0° (DMF, c=1.00)

(Example 36) (+)-cis-5-Hydroxy-3-[1-(5-isopropoxypyridin-2-yl)piperidin-4-yl]-4-(trifluoromethyl)-1,4,5,7-tetrahydro-6H-pyrazolo[3,4-b]pyridin-6-one

[Formula 82]

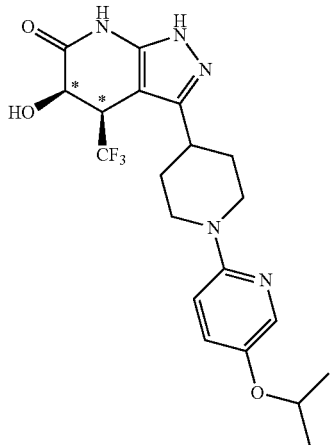

(+)-Menthyl chloroformate (0.139 mL, 0.655 mmol) was added at 0° C. to a mixed suspension of cis-5-hydroxy-3-[1-(5-isopropoxypyridin-2-yl)piperidin-4-yl]-4-(trifluoromethyl)-1,4,5,7-tetrahydro-6H-pyrazolo[3,4-b]pyridin-6-one (0.240 g, 0.546 mmol) produced in Example 5 and triethylamine (83.3 μL, 0.601 mmol) in THF (24 mL) and ethyl acetate (6 mL), and the mixture was stirred at 0° C. for 2 hours and then at room temperature for 16 hours. THF (24 mL) was further added thereto, then triethylamine (83.3 μL, 0.601 mmol) and (+)-menthyl chloroformate (0.139 mL, 0.655 mmol) were further added thereto at 0° C., and the mixture was stirred at room temperature for 3 hours. Triethylamine (41.6 μL, 0.300 mmol) and (+)-menthyl chloroformate (69.6 μL, 0.328 mmol) were further added thereto, and the mixture was stirred at room temperature for 2 hours. To the reaction mixture, water was added, followed by extraction with ethyl acetate. The obtained organic layer was washed with brine and dried over anhydrous sodium sulfate, and the solvent was concentrated under reduced pressure. The obtained residue was purified by silica gel column chromatography [elute: hexane/ethyl acetate=93/7-40/60 (gradient)] to obtain each of a compound (0.156 g) eluted first and a compound (0.139 g) eluted second.

Morpholine (43.7 μL, 0.502 mmol) was added at room temperature to a solution of the compound eluted first obtained by the procedures described above in acetonitrile (4 mL), and the mixture was stirred for 16 hours. Dichloromethane (3 mL) was added thereto, and the mixture was stirred for 10 minutes. Then, the resulting precipitate was collected by filtration to obtain the title compound (70.2 mg, yield: 29%, optically active form).

$[\alpha]_D^{25}$=+8.3° (DMF, c=0.922).

(Reference Example 40) 3-{1-[5-(Difluoromethoxy)pyridin-2-yl]piperidin-4-yl}-1-(diphenylmethyl)-1H-pyrazol-5-amine

[Formula 83]

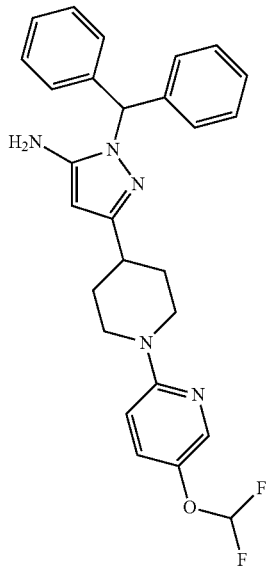

The title compound (2.04 g, yield: 83%) was obtained through the same reaction as in the method described in Reference Example 1 using ethyl 1-[5-(difluoromethoxy)pyridin-2-yl]piperidine-4-carboxylate (compound described in the pamphlet of WO2013/187462, 1.56 g, 5.19 mmol) instead of ethyl 1-[5-(trifluoromethyl)pyridin-2-yl]piperidine-4-carboxylate and diphenylmethyl hydrazine acetate (1.38 g, 5.34 mmol) instead of diphenylmethyl hydrazine hydrochloride.

$^1$H-NMR (400 MHz, DMSO-d$_6$) δ: 7.99 (1H, d, J=3 Hz), 7.41 (1H, dd, J=9 Hz, 3 Hz), 7.33-7.19 (10H, m), 6.95 (1H, d, J=75 Hz), 6.87 (1H, d, J=9 Hz), 6.59 (1H, s), 5.31 (1H, brs), 5.17 (1H, s), 4.23-4.20 (2H, m), 2.91-2.84 (2H, m), 2.68-2.58 (1H, m), 1.85-1.80 (2H, m), 1.54-1.44 (2H, m).

(Reference Example 41) 3-{1-[5-(Difluoromethoxy)pyridin-2-yl]piperidin-4-yl}-1-(diphenylmethyl)-4-(trifluoromethyl)-1,4,5,7-tetrahydro-6H-pyrazolo[3,4-b]pyridin-6-one

[Formula 84]

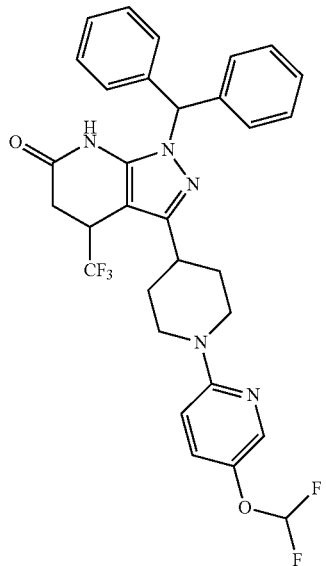

1,4-Diazabicyclo[2.2.2]octane (530 mg, 4.72 mmol), Meldrum's acid (1.35 g, 9.37 mmol), and trifluoroacetaldehyde ethyl hemiacetal (1.30 g, 9.02 mmol) were added to a solution of 3-{1-[5-(difluoromethoxy)pyridin-2-yl]piperidin-4-yl}-1-(diphenylmethyl)-1H-pyrazol-5-amine (1.17 g, 2.46 mmol) produced in Reference Example 40 in ethanol (20 mL), and the mixture was stirred for 6 hours under heating to reflux. The solvent in the reaction solution was distilled off under reduced pressure. To the obtained residue, acetic acid (10 mL) was added, and the mixture was stirred at room temperature for 1 hour. The solvent was distilled off under reduced pressure. To the obtained residue, a saturated sodium bicarbonate aqueous solution was added, followed by extraction with ethyl acetate three times. The obtained organic layer was washed with brine and dried over anhydrous magnesium sulfate, and the solvent was distilled off under reduced pressure. The obtained residue was purified by silica gel column chromatography [elute: hexane/ethyl acetate=100/0-50/50 (gradient)] and further purified by silica gel column chromatography [NH-silica gel, elute: hexane/ethyl acetate=100/0-50/50 (gradient)] to obtain the title compound (1.35 g, yield: 92%).

$^1$H-NMR (400 MHz, DMSO-d$_6$) δ: 11.18 (1H, s), 7.99 (1H, d, J=3 Hz), 7.41 (1H, dd, J=9 Hz, 3 Hz), 7.36-7.17 (10H, m), 6.95 (1H, d, J=74 Hz), 6.88 (1H, d, J=9 Hz), 6.81 (1H, s), 4.30-4.25 (2H, m), 4.09-3.98 (1H, m), 3.15-3.08 (1H, m), 2.94-2.81 (4H, m), 1.91-1.77 (2H, m), 1.72-1.51 (2H, m).

(Reference Example 42) Methyl 3-{1-[5-(difluoromethoxy)pyridin-2-yl]piperidin-4-yl}-1-(diphenylmethyl)-5-hydroxy-6-oxo-4-(trifluoromethyl)-4,5,6,7-tetrahydro-1H-pyrazolo[3,4-b]pyridine-5-carboxylate

[Formula 85]

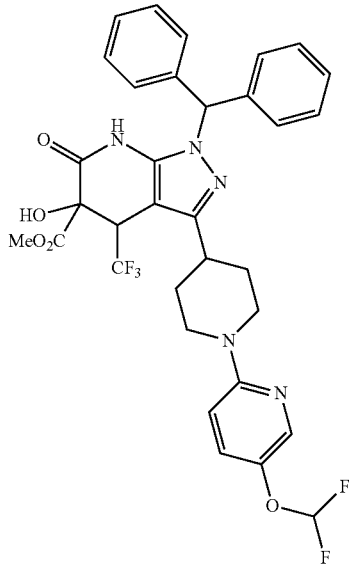

Dimethyl carbonate (0.30 mL, 3.6 mmol) was added to a solution of 3-{1-[5-(difluoromethoxy)pyridin-2-yl]piperidin-4-yl}-1-(diphenylmethyl)-4-(trifluoromethyl)-1,4,5,7-tetrahydro-6H-pyrazolo[3,4-b]pyridin-6-one (1.28 g, 2.14 mmol) produced in Reference Example 41 in THF (20 mL), and the mixture was cooled to −78° C. Then, lithium diisopropylamide (solution in hexane and THF, 5.90 mL, 6.43 mmol) was added dropwise thereto, and the mixture was heated to 0° C., and stirred for 30 minutes as it was. To the reaction solution, a saturated ammonium chloride aqueous solution was added, followed by extraction with ethyl acetate three times. The obtained organic layer was dried over magnesium sulfate, and the solvent was distilled off under reduced pressure. The obtained residue was purified by silica gel chromatography [NH-silica gel, elute: dichloromethane/methanol=100/0-90/10 (gradient)] to obtain a synthesis intermediate.

DBU (1.23 mL, 8.25 mmol), (1S)-(+)-(10-camphorsulfonyl)oxaziridine (157 mg, 0.684 mmol), and (1R)-(−)-(10-camphorsulfonyl)oxaziridine (155 mg, 0.676 mmol) were added to a solution of the synthesis intermediate obtained by the procedures described above in THF (10 mL), and the mixture was stirred at room temperature for 2 hours. To the reaction solution, a saturated ammonium chloride aqueous solution was added, followed by extraction with ethyl acetate three times. The obtained organic layer was washed with brine and dried over anhydrous magnesium sulfate, and the solvent was distilled off under reduced pressure. The obtained residue was purified by silica gel column chromatography [NH-silica gel, elute: dichloromethane/methanol=100/0-90/10 (gradient)] to obtain the title compound (558 mg, yield: 39%).

$^1$H-NMR (400 MHz, DMSO-d$_6$) δ: 11.48 (1H, s), 7.95 (1H, d, J=3 Hz), 7.36 (1H, dd, J=9 Hz, 3 Hz), 7.32-7.12 (10H, m), 6.91 (1H, d, J=75 Hz), 6.85-6.81 (2H, m), 4.28-4.17 (2H, m), 4.10-4.03 (1H, m), 3.69 (3H, s), 2.89-2.77 (3H, m), 1.86-1.82 (2H, m), 1.47-1.35 (2H, m).

(Reference Example 43) cis-3-{1-[5-(Difluoromethoxy)pyridin-2-yl]piperidin-4-yl}-1-(diphenylmethyl)-5-hydroxy-4-(trifluoromethyl)-1,4,5,7-tetrahydro-6H-pyrazolo[3,4-b]pyridin-6-one

[Formula 86]

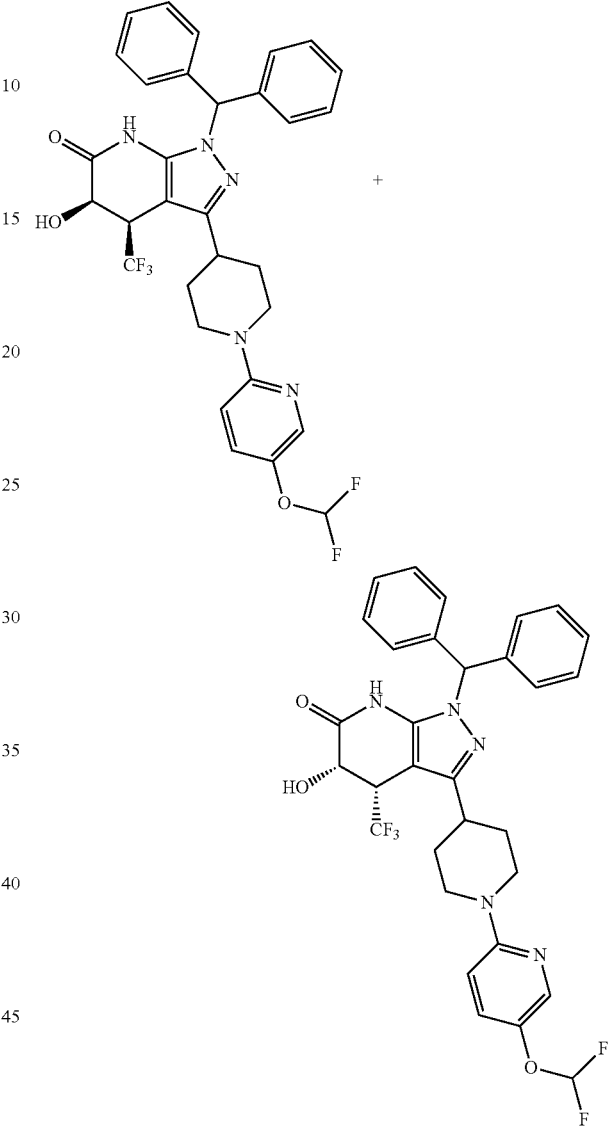

Lithium hydroxide (60 mg, 2.5 mmol) was added to a mixed solution of methyl 3-{1-[5-(difluoromethoxy)pyridin-2-yl]piperidin-4-yl}-1-(diphenylmethyl)-5-hydroxy-6-oxo-4-(trifluoromethyl)-4,5,6,7-tetrahydro-1H-pyrazolo[3,4-b]pyridine-5-carboxylate (558 mg, 0.831 mmol) produced in Reference Example 42 in ethanol (4 mL) and water (2 mL), and the mixture was stirred at 50° C. for 2 hours. The solvent in the reaction solution was distilled off under reduced pressure, and a saturated ammonium chloride aqueous solution and ethyl acetate were added to the obtained residue, followed by extraction with ethyl acetate three times. The obtained organic layer was washed with brine and dried over anhydrous magnesium sulfate, and the solvent was distilled off under reduced pressure. The obtained residue was purified by silica gel column chromatography [elute: hexane/ethyl acetate=100/0-50/50 (gradient)] to obtain the title compound (345 mg, yield: 68%).

$^1$H-NMR (400 MHz, DMSO-d$_6$) δ: 11.21 (1H, s), 7.99 (1H, d, J=3 Hz), 7.41 (1H, dd, J=9 Hz, 3 Hz), 7.36-7.14

(10H, m), 6.95 (1H, d, J=74 Hz), 6.88 (1H, d, J=9 Hz), 6.74 (1H, s), 5.79 (1H, d, J=4 Hz), 4.58-4.54 (1H, m), 4.31-4.24 (2H, m), 4.18-4.10 (1H, m), 2.95-2.82 (3H, m), 1.97-1.49 (4H, m).

(Example 37) cis-3-{1-[5-(Difluoromethoxy)pyridin-2-yl]piperidin-4-yl}-5-hydroxy-4-(trifluoromethyl)-1,4,5,7-tetrahydro-6H-pyrazolo[3,4-b]pyridin-6-one

[Formula 87]

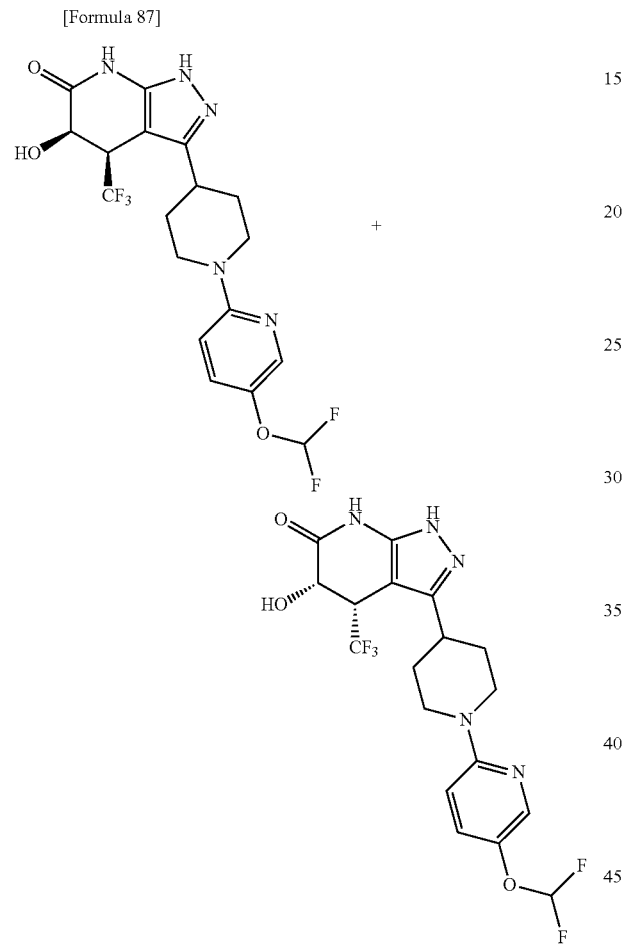

The title compound (103 mg, yield: 87%) was obtained through the same reaction as in the method described in Example 26 using cis-3-{1-[5-(difluoromethoxy)pyridin-2-yl]piperidin-4-yl}-1-(diphenylmethyl)-5-hydroxy-4-(trifluoromethyl)-1,4,5,7-tetrahydro-6H-pyrazolo[3,4-b]pyridin-6-one (162 mg, 0.264 mmol) produced in Reference Example 43 instead of cis-1-(diphenylmethyl)-5-hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one, followed by the purification of the obtained residue by silica gel column chromatography [elute: ethyl acetate/methanol=100/0-95/5 (gradient)].

¹H-NMR (400 MHz, DMSO-d₆) δ: 12.22 (1H, s), 10.53 (1H, s), 8.02 (1H, d, J=3 Hz), 7.44 (1H, dd, J=9 Hz, 3 Hz), 7.25 (1H, s), 6.97 (1H, d, J=74 Hz), 6.92 (1H, d, J=9 Hz), 5.51 (1H, d, J=4 Hz), 4.45-4.34 (2H, m), 4.19-4.10 (1H, m), 3.04-2.94 (1H, m), 2.90-2.80 (2H, m), 1.85-1.58 (4H, m); MS (ESI) m/z: 448 (M+H)⁺.

(Reference Example 44) 1-(Diphenylmethyl)-3-{1-[5-(trifluoromethyl)pyridin-3-yl]piperidin-4-yl}-1H-pyrazol-5-amine

[Formula 88]

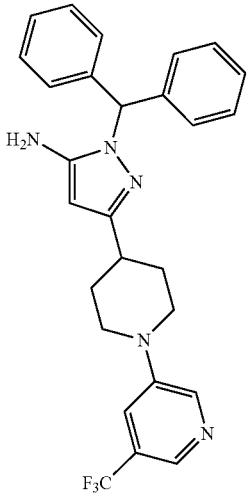

The title compound (2.55 g, yield: 80%) was obtained through the same reaction as in the method described in Reference Example 1 using ethyl 1-[5-(trifluoromethyl)pyridin-3-yl]piperidine-4-carboxylate (compound described in the pamphlet of WO2013/187462, 2.02 g, 6.68 mmol) instead of ethyl 1-[5-(trifluoromethyl)pyridin-2-yl]piperidine-4-carboxylate.

¹H-NMR (400 MHz, CDCl₃) δ: 8.45-8.41 (1H, m), 8.25-8.22 (1H, m), 7.37-7.14 (11H, m), 6.64 (1H, s), 3.78-3.69 (2H, m), 3.25-3.16 (2H, m), 2.94-2.84 (2H, m), 2.78-2.69 (1H, m), 2.06-1.98 (2H, m), 1.82-1.69 (2H, m).

(Reference Example 45) 1-(Diphenylmethyl)-4-(trifluoromethyl)-3-{1-[5-(trifluoromethyl)pyridin-3-yl]piperidin-4-yl}-1,4,5,7-tetrahydro-6H-pyrazolo[3,4-b]pyridin-6-one

[Formula 89]

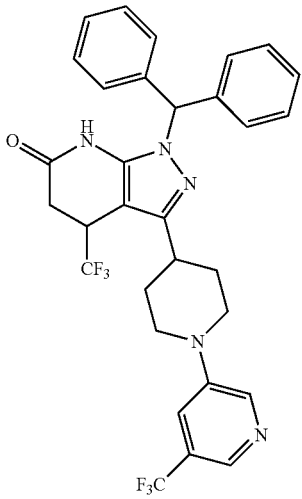

The same reaction as in the method described in Reference Example 41 was carried out using 1-(diphenylmethyl)-3-{1-[5-(trifluoromethyl)pyridin-3-yl]piperidin-4-yl}-1H-pyrazol-5-amine (2.55 g, 5.34 mmol) produced in Reference Example 44 instead of 3-{1-[5-(difluoromethoxy)pyridin-2-yl]piperidin-4-yl}-1-(diphenylmethyl)-1H-pyrazol-5-amine. To the obtained residue, diisopropyl ether was added, and the mixture was stirred. The precipitate was collected by filtration to obtain the title compound (2.85 g, yield: 89%).

$^1$H-NMR (400 MHz, CDCl$_3$) δ: 8.45 (1H, d, J=3 Hz), 8.31-8.25 (1H, m), 7.42-7.08 (10H, m), 7.06-6.99 (1H, m), 6.70 (1H, s), 3.86-3.75 (2H, m), 3.66-3.54 (1H, m), 3.01-2.74 (5H, m), 2.08-1.84 (4H, m).

(Reference Example 46) Methyl 1-(diphenylmethyl)-5-hydroxy-6-oxo-4-(trifluoromethyl)-3-{1-[5-(trifluoromethyl)pyridin-3-yl]piperidin-4-yl}-4,5,6,7-tetrahydro-1H-pyrazolo[3,4-b]pyridine-5-carboxylate

[Formula 90]

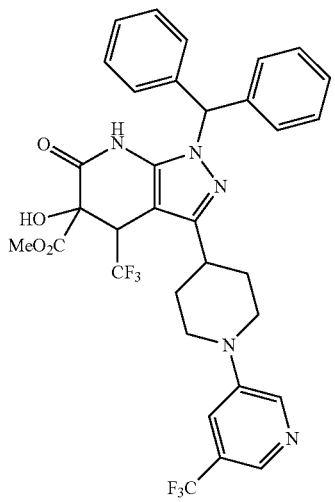

The same reaction as in the method described in Reference Example 42 was carried out using 1-(diphenylmethyl)-4-(trifluoromethyl)-3-{1-[5-(trifluoromethyl)pyridin-3-yl]piperidin-4-yl}-1,4,5,7-tetrahydro-6H-pyrazolo[3,4-b]pyridin-6-one (2.85 g, 4.7 mmol) produced in Reference Example 45 instead of 3-{1-[5-(difluoromethoxy)pyridin-2-yl]piperidin-4-yl}-1-(diphenylmethyl)-4-(trifluoromethyl)-1,4,5,7-tetrahydro-6H-pyrazolo[3,4-b]pyridin-6-one. To the obtained residue, methanol was added, and the mixture was stirred. The precipitate was collected by filtration to obtain the title compound (0.980 g, yield: 44%).

$^1$H-NMR (400 MHz, DMSO-d$_6$) δ: 11.54 (1H, s), 8.58 (1H, d, J=3 Hz), 8.26-8.23 (1H, m), 7.57-7.53 (1H, m), 7.37-7.24 (8H, m), 7.22-7.17 (2H, m), 6.88 (1H, s), 4.17-4.07 (1H, m), 3.97-3.84 (2H, m), 3.74 (3H, s), 2.98-2.78 (3H, m), 1.98-1.79 (3H, m), 1.68-1.56 (1H, m).

(Example 38) (+)-cis-5-Hydroxy-4-(trifluoromethyl)-3-{1-[5-(trifluoromethyl)pyridin-3-yl]piperidin-4-yl}-1,4,5,7-tetrahydro-6H-pyrazolo[3,4-b]pyridin-6-one

[Formula 91]

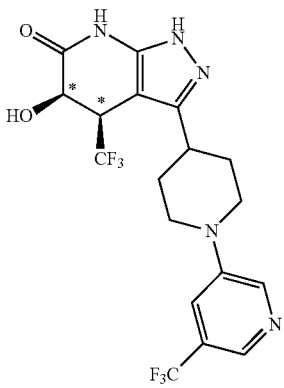

Lithium hydroxide monohydrate (0.183 g, 4.36 mmol) was added to a mixed solution of methyl 1-(diphenylmethyl)-5-hydroxy-6-oxo-4-(trifluoromethyl)-3-{1-[5-(trifluoromethyl)pyridin-3-yl]piperidin-4-yl}-4,5,6,7-tetrahydro-1H-pyrazolo[3,4-b]pyridine-5-carboxylate (0.980 g, 1.45 mmol) produced in Reference Example 46 in 1,4-dioxane (15 mL) and water (5 mL), and the mixture was stirred at 60° C. for 1 hour. To the reaction solution, an ammonium chloride aqueous solution was added, followed by extraction with ethyl acetate. The obtained organic layer was dried over anhydrous sodium sulfate, and the solvent was distilled off under reduced pressure to obtain a crude product (0.911 g).

A synthesis intermediate was obtained through the same reaction as in the method described in Example 26 using a portion (0.250 g) of the crude product obtained by the procedures described above instead of cis-1-(diphenylmethyl)-5-hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one.

A mixed solution of the synthesis intermediate obtained by the procedures described above in ethyl acetate and methanol was adsorbed onto a silica gel, and the solvent was distilled off under reduced pressure. The obtained powder was purified by flash LC [column: Chiralflash IA (30 mm i.d.×100 mm); manufactured by Daicel Corporation, elute: hexane/ethanol=20/80, flow rate: 10 mL/min] to obtain the title compound (63.5 mg, yield: 35%, optically active form).

The optical purity was measured using HPLC [column: Chiralpak IA (4.6 mm i.d.×150 mm); manufactured by Daicel Corporation, elute: ethanol, flow rate: 2.0 mL/min].

Optical purity: 98% (retention time: 5.0 min).

$^1$H-NMR (400 MHz, DMSO-d$_6$) δ: 12.26 (1H, s), 10.55 (1H, s), 8.62 (1H, d, J=3 Hz), 8.29-8.26 (1H, m), 7.63-7.59 (1H, m), 5.53 (1H, d, J=4 Hz), 4.47-4.42 (1H, m), 4.21-4.01 (3H, m), 3.03-2.85 (3H, m), 1.90-1.71 (4H, m);

MS (ESI) m/z: 450 (M+H)$^+$;

$[α]_D^{25}$=+5.4° (DMF, c=1.00)

(Reference Example 47) 1-(Diphenylmethyl)-3-[1-(6-isopropoxypyridin-3-yl)piperidin-4-yl]-1H-pyrazol-5-amine

[Formula 92]

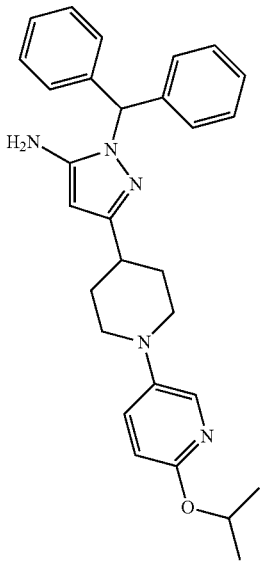

The title compound (531 mg, yield: 34%) was obtained through the same reaction as in the method described in Reference Example 1 using ethyl 1-(6-isopropoxypyridin-3-yl)piperidine-4-carboxylate (compound described in the pamphlet of WO2013/187462, 980 mg, 3.35 mmol) instead of ethyl 1-[5-(trifluoromethyl)pyridin-2-yl]piperidine-4-carboxylate.

$^1$H-NMR (CDCl$_3$) δ: 7.81 (1H, d, J=3 Hz), 7.37-7.28 (7H, m), 7.23-7.20 (4H, m), 6.67 (1H, s), 6.61 (1H, d, J=9 Hz), 5.46 (1H, s), 5.21-5.15 (1H, m), 3.52-3.47 (2H, m), 3.25 (2H, s), 2.72 (2H, td, J=12 Hz, 3 Hz), 2.67 (1H, tt, J=12 Hz, 4 Hz), 2.05-2.00 (2H, m), 1.88-1.77 (2H, m), 1.32 (6H, d, J=7 Hz).

(Reference Example 48) 1-(Diphenylmethyl)-3-[1-(6-isopropoxypyridin-3-yl)piperidin-4-yl]-4-(trifluoromethyl)-1,4,5,7-tetrahydro-6H-pyrazolo[3,4-b]pyridin-6-one

[Formula 93]

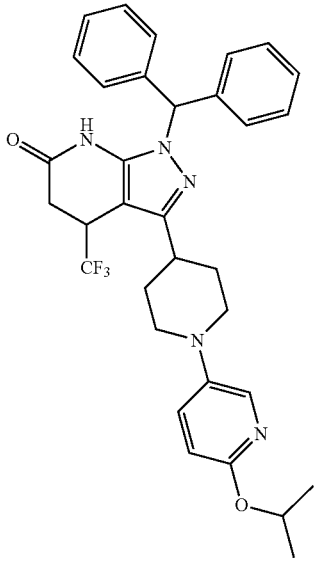

The title compound (512 mg, yield: 81%) was obtained through the same reaction as in the method described in Reference Example 41 using 1-(diphenylmethyl)-3-[1-(6-isopropoxypyridin-3-yl)piperidin-4-yl]-1H-pyrazol-5-amine (500 mg, 1.07 mmol) produced in Reference Example 47 instead of 3-{1-[5-(difluoromethoxy)pyridin-2-yl]piperidin-4-yl}-1-(diphenylmethyl)-1H-pyrazol-5-amine.

$^1$H-NMR (CDCl$_3$) δ: 8.32 (1H, brs), 7.80 (1H, d, J=3 Hz), 7.38-7.33 (6H, m), 7.28 (1H, dd, J=9 Hz, 3 Hz), 7.23-7.18 (4H, m), 6.67 (1H, s), 6.61 (1H, d, J=9 Hz), 5.21-5.15 (1H, m), 3.66-3.57 (1H, m), 3.56-3.48 (2H, m), 2.90-2.85 (2H, m), 2.77-2.66 (3H, m), 2.12-1.93 (4H, m), 1.33 (6H, d, J=6 Hz).

(Reference Example 49) Methyl 1-(diphenylmethyl)-5-hydroxy-6-oxo-3-[1-(6-isopropoxypyridin-3-yl)piperidin-4-yl]-4-(trifluoromethyl)-4,5,6,7-tetrahydro-1H-pyrazolo[3,4-b]pyridine-5-carboxylate

[Formula 94]

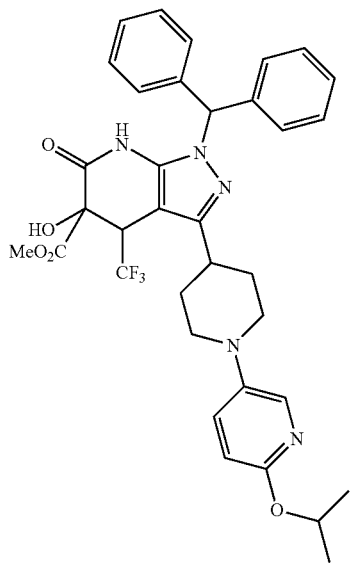

The title compound (285 mg, yield: 52%) was obtained through the same reaction as in the method described in Reference Example 42 using 1-(diphenylmethyl)-3-[1-(6-isopropoxypyridin-3-yl)piperidin-4-yl]-4-(trifluoromethyl)-1,4,5,7-tetrahydro-6H-pyrazolo[3,4-b]pyridin-6-one (490 mg, 0.831 mmol) produced in Reference Example 48 instead of 3-{1-[5-(difluoromethoxy)pyridin-2-yl]piperidin-4-yl}-1-(diphenylmethyl)-4-(trifluoromethyl)-1,4,5,7-tetrahydro-6H-pyrazolo[3,4-b]pyridin-6-one.

$^1$H-NMR (CDCl$_3$) δ: 7.78 (1H, d, J=3 Hz), 7.41-7.36 (6H, m), 7.28-7.26 (1H, m), 7.18-7.10 (5H, m), 6.76 (1H, s), 6.61 (1H, d, J=9 Hz), 5.21-5.15 (1H, m), 4.27 (1H, s), 3.89 (3H, s), 3.83-3.76 (1H, m), 3.55-3.46 (2H, m), 2.76-2.66 (3H, m), 2.15-1.82 (4H, m), 1.32 (6H, d, J=6 Hz).

(Example 39) Optically active form of cis-5-hydroxy-3-[1-(6-isopropoxypyridin-3-yl)piperidin-4-yl]-4-(trifluoromethyl)-1,4,5,7-tetrahydro-6H-pyrazolo[3,4-b]pyridin-6-one

[Formula 95]

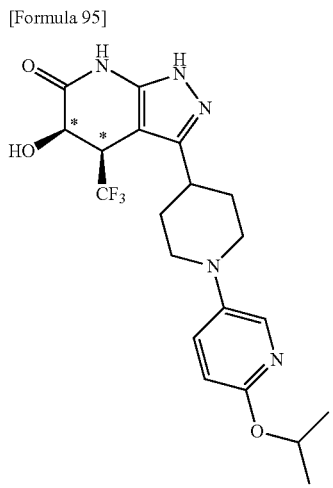 [SMILES: CC(C)Oc1ccc(N2CCC(c3n[nH]c4c3[C@@H](C(F)(F)F)[C@@H](O)C(=O)N4)CC2)cn1]

A crude product was obtained through the same reaction as in the method described in Reference Example 43 using methyl 1-(diphenylmethyl)-5-hydroxy-6-oxo-3-[1-(6-isopropoxypyridin-3-yl)piperidin-4-yl]-4-(trifluoromethyl)-4,5,6,7-tetrahydro-1H-pyrazolo[3,4-b]pyridine-5-carboxylate (282 mg, 0.425 mmol) produced in Reference Example 49 instead of methyl 3-{1-[5-(difluoromethoxy)pyridin-2-yl]piperidin-4-yl}-1-(diphenylmethyl)-5-hydroxy-6-oxo-4-(trifluoromethyl)-4,5,6,7-tetrahydro-1H-pyrazolo [3,4-b]pyridine-5-carboxylate.

A synthesis intermediate (187 mg) was obtained through the same reaction as in the method described in Example 26 using the crude product obtained by the procedures described above instead of cis-1-(diphenylmethyl)-5-hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one.

Triethylamine (0.0638 mL, 0.461 mmol) and (+)-menthyl chloroformate (0.107 mL, 0.502 mmol) were added at 0° C. to a mixed suspension of a portion (184 mg) of the synthesis intermediate obtained by the procedures described above in THF (15 mL) and ethyl acetate (5 mL), and the mixture was stirred at 0° C. for 1 hour and then at room temperature for 4 hours. Triethylamine (0.0697 mL, 0.502 mmol) and (+)-menthyl chloroformate (0.133 mL, 0.628 mmol) were further added thereto, and the mixture was stirred at room temperature for 3 hours. Triethylamine (0.0104 mL, 0.754 mmol) and (+)-menthyl chloroformate (0.178 mL, 0.837 mmol) were further added thereto, and the mixture was stirred overnight. To the reaction mixture, water was added, followed by extraction with ethyl acetate three times. The obtained organic layer was washed with brine and dried over anhydrous sodium sulfate, and the solvent was concentrated under reduced pressure. The obtained residue was purified by silica gel column chromatography [elute: hexane/ethyl acetate=100/0-70/30 (gradient)] to obtain each of a compound (70 mg) eluted first and a compound (67 mg) eluted second.

The title compound (39.3 mg, yield: 22%, optically active form) was obtained through the same reaction as in the method described in Example 36 using a portion (68 mg) of the compound eluted first obtained by the procedures described above instead of cis-5-hydroxy-3-[1-(5-isopropoxypyridin-2-yl)piperidin-4-yl]-4-(trifluoromethyl)-1,4,5,7-tetrahydro-6H-pyrazolo[3,4-b]pyridin-6-one.

The optical purity was measured using HPLC [column: Chiralpak IA (4.6 mm i.d.×150 mm); manufactured by Daicel Corporation, elute: hexane/ethanol=50/50, flow rate: 1.0 mL/min].

Optical purity: 98% (retention time: 8.9 min);

$^1$H-NMR (400 MHz, DMSO-$d_6$) δ: 12.28 (1H, s), 10.55 (1H, s), 7.80 (1H, d, J=3 Hz), 7.44 (1H, dd, J=9 Hz, 3 Hz), 6.63 (1H, d, J=9 Hz), 5.51 (1H, d, J=4 Hz), 5.15-5.09 (1H, m), 4.46-4.43 (1H, m), 4.19-4.10 (1H, m), 3.63-3.58 (2H, m), 2.87-2.79 (1H, m), 2.70-2.62 (2H, m), 1.94-1.75 (4H, m), 1.25 (6H, d, J=6 Hz);

MS (ESI) m/z: 440 (M+H)$^+$.

(Reference Example 50) 3-[1-(2-Cyclopropylpyrimidin-5-yl)piperidin-4-yl]-1-(diphenylmethyl)-1H-pyrazol-5-amine

[Formula 96]

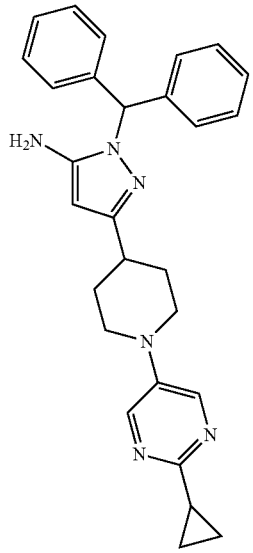

The title compound (0.878 g, yield: 34%) was obtained through the same reaction as in the method described in Reference Example 1 using ethyl 1-(2-cyclopropylpyrimidin-5-yl) piperidine-4-carboxylate (compound described in the pamphlet of WO2013/187462, 1.60 g, 5.81 mmol) instead of ethyl 1-[5-(trifluoromethyl)pyridin-2-yl]piperidine-4-carboxylate.

$^1$H-NMR (CDCl$_3$) δ: 8.25 (2H, s), 7.37-7.28 (6H, m), 7.22-7.20 (4H, m), 6.67 (1H, s), 5.44 (1H, s), 3.65-3.60 (2H, m), 3.26 (2H, s), 2.85-2.78 (2H, m), 2.75-2.68 (1H, m), 2.19-2.13 (1H, m), 2.06-2.01 (2H, m), 1.85-1.74 (2H, m), 1.04-0.95 (4H, m).

(Reference Example 51) 3-[1-(2-Cyclopropylpyrimidin-5-yl)piperidin-4-yl]-1-(diphenylmethyl)-4-(trifluoromethyl)-1,4,5,7-tetrahydro-6H-pyrazolo[3,4-b]pyridin-6-one

[Formula 97]

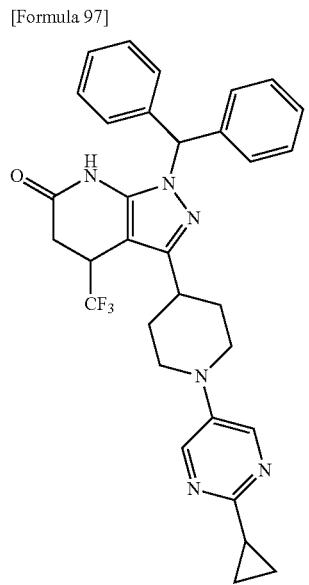 [SMILES: O=C1CC(C(F)(F)F)c2c(C3CCN(c4cnc(C5CC5)nc4)CC3)nn(C(c3ccccc3)c3ccccc3)c2N1]

The title compound (0.927 g, yield: 84%) was obtained through the same reaction as in the method described in Reference Example 41 using 3-[1-(2-cyclopropylpyrimidin-5-yl)piperidin-4-yl]-1-(diphenylmethyl)-1H-pyrazol-5-amine (0.873 g, 1.94 mmol) produced in Reference Example 50 instead of 3-{1-[5-(difluoromethoxy)pyridin-2-yl]piperidin-4-yl}-1-(diphenylmethyl)-1H-pyrazol-5-amine, followed by the purification of the obtained residue by silica gel column chromatography [elute: hexane/ethyl acetate=90/10-20/80 (gradient)].

$^1$H-NMR (400 MHz, CDCl$_3$) δ: 8.25 (2H, s), 7.78 (1H, s), 7.39-7.34 (6H, m), 7.18-7.14 (4H, m), 6.68 (1H, s), 3.69-3.56 (3H, m), 2.88-2.70 (5H, m), 2.20-2.13 (1H, m), 2.04-1.90 (4H, m), 1.04-0.96 (4H, m).

(Reference Example 52) Methyl 3-[1-(2-cyclopropylpyrimidin-5-yl)piperidin-4-yl]-1-(diphenylmethyl)-5-hydroxy-6-oxo-4-(trifluoromethyl)-4,5,6,7-tetrahydro-1H-pyrazolo[3,4-b]pyridine-5-carboxylate

[Formula 98]

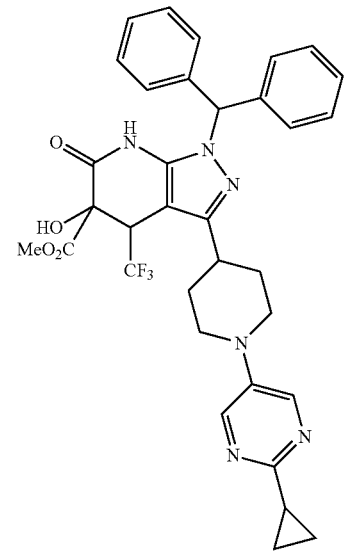

The same reaction as in the method described in Reference Example 42 was carried out using 3-[1-(2-cyclopropylpyrimidin-5-yl)piperidin-4-yl]-1-(diphenylmethyl)-4-(trifluoromethyl)-1,4,5,7-tetrahydro-6H-pyrazolo[3,4-b]pyridin-6-one (0.927 g, 1.62 mmol) produced in Reference Example 51 instead of 3-{1-[5-(difluoromethoxy)pyridin-2-yl]piperidin-4-yl}-1-(diphenylmethyl)-4-(trifluoromethyl)-1,4,5,7-tetrahydro-6H-pyrazolo[3,4-b]pyridin-6-one. To the obtained residue, dichloromethane was added, and the mixture was stirred. The precipitate was collected by filtration to obtain the title compound (0.404 g, yield: 39%).

$^1$H-NMR (400 MHz, DMSO-d$_6$) δ: 11.54 (1H, s), 8.34 (2H, s), 7.37-7.25 (9H, m), 7.21-7.19 (2H, m), 6.88 (1H, s), 4.11 (1H, q, J=10 Hz), 3.74-3.67 (5H, m), 2.80-2.70 (3H, m), 2.11-2.05 (1H, m), 1.94-1.77 (3H, m), 1.67-1.57 (1H, m), 0.94-0.84 (4H, m).

(Reference Example 53) cis-3-[1-(2-Cyclopropylpyrimidin-5-yl)piperidin-4-yl]-1-(diphenylmethyl)-5-hydroxy-4-(trifluoromethyl)-1,4,5,7-tetrahydro-6H-pyrazolo[3,4-b]pyridin-6-one

[Formula 99]

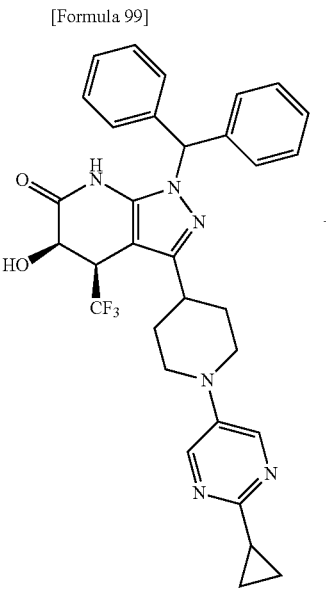

+

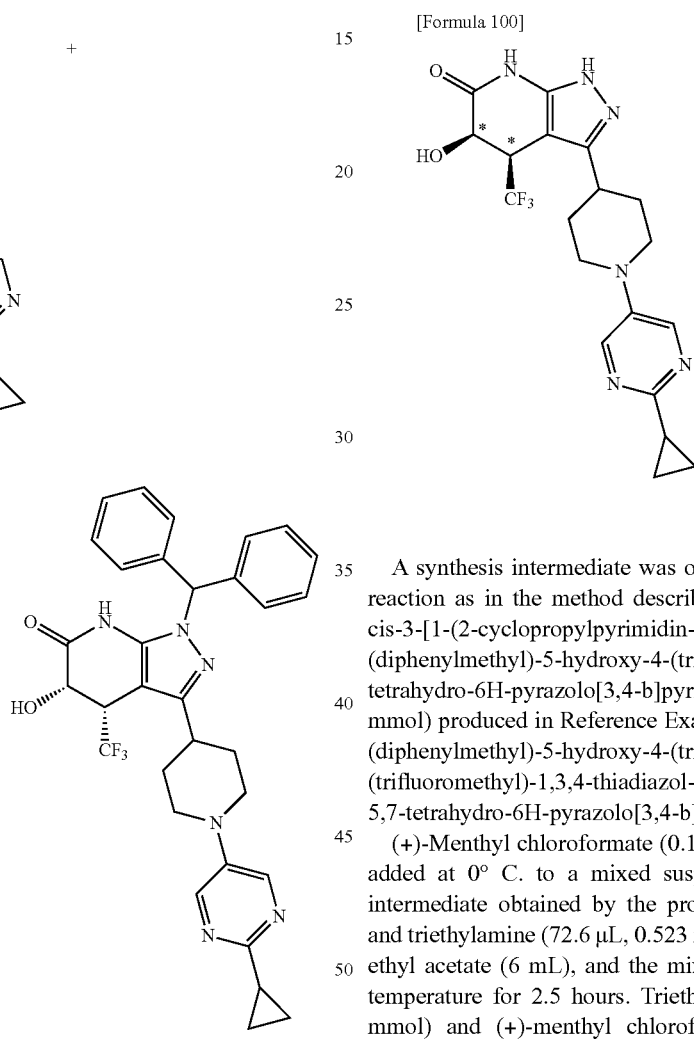

The title compound (0.307 g, yield: 84%) was obtained through the same reaction as in the method described in Reference Example 43 using methyl 3-[1-(2-cyclopropylpyrimidin-5-yl)piperidin-4-yl]-1-(diphenylmethyl)-5-hydroxy-6-oxo-4-(trifluoromethyl)-4,5,6,7-tetrahydro-1H-pyrazolo[3,4-b]pyridine-5-carboxylate (0.400 g, 0.619 mmol) produced in Reference Example 52 instead of methyl 3-{1-[5-(difluoromethoxy)pyridin-2-yl]piperidin-4-yl}-1-(diphenylmethyl)-5-hydroxy-6-oxo-4-(trifluoromethyl)-4,5,6,7-tetrahydro-1H-pyrazolo[3,4-b]pyridine-5-carboxylate.

$^1$H-NMR (400 MHz, DMSO-$d_6$) δ: 11.22 (1H, s), 8.35 (2H, s), 7.36-7.17 (10H, m), 6.75 (1H, s), 5.80 (1H, d, J=4 Hz), 4.57 (1H, dd, J=7 Hz, 4 Hz), 4.19-4.10 (1H, m), 3.75-3.68 (2H, m), 2.81-2.71 (3H, m), 2.11-2.05 (1H, m), 1.97-1.91 (1H, m), 1.83-1.65 (3H, m), 0.94-0.84 (4H, m).

(Example 40) Optically active form of cis-3-[1-(2-cyclopropylpyrimidin-5-yl)piperidin-4-yl]-5-hydroxy-4-(trifluoromethyl)-1,4,5,7-tetrahydro-6H-pyrazolo[3,4-b]pyridin-6-one

[Formula 100]

A synthesis intermediate was obtained through the same reaction as in the method described in Example 26 using cis-3-[1-(2-cyclopropylpyrimidin-5-yl)piperidin-4-yl]-1-(diphenylmethyl)-5-hydroxy-4-(trifluoromethyl)-1,4,5,7-tetrahydro-6H-pyrazolo[3,4-b]pyridin-6-one (0.302 g, 0.513 mmol) produced in Reference Example 53 instead of cis-1-(diphenylmethyl)-5-hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one.

(+)-Menthyl chloroformate (0.121 mL, 0.571 mmol) was added at 0° C. to a mixed suspension of the synthesis intermediate obtained by the procedures described above and triethylamine (72.6 μL, 0.523 mmol) in THF (6 mL) and ethyl acetate (6 mL), and the mixture was stirred at room temperature for 2.5 hours. Triethylamine (19.8 μL, 0.143 mmol) and (+)-menthyl chloroformate (40.4 μL, 0.190 mmol) were further added thereto at 0° C., and the mixture was stirred at room temperature for 1 hour. Triethylamine (13.2 μL, 0.0952 mmol) and (+)-menthyl chloroformate (30.3 μL, 0.143 mmol) were further added thereto at 0° C., and the mixture was stirred at room temperature for 1 hour. To the reaction mixture, ethyl acetate was added. The organic layer was washed with brine and dried over anhydrous sodium sulfate, and the solvent was concentrated under reduced pressure. The obtained residue was purified by silica gel column chromatography [elute: hexane/ethyl acetate=93/7-40/60 (gradient)] to obtain each of a compound (111 mg) eluted first and a compound (83.3 mg) eluted second.

The title compound (52.1 mg, yield: 24%, optically active form) was obtained through the same reaction as in the method described in Example 36 using the compound eluted first obtained by the procedures described above instead of cis-5-hydroxy-3-[1-(5-isopropoxypyridin-2-yl)piperidin-4-yl]-4-(trifluoromethyl)-1,4,5,7-tetrahydro-6H-pyrazolo[3,4-b]pyridin-6-one.

The optical purity was measured using HPLC [column: Chiralpak IA (4.6 mm i.d.×250 mm); manufactured by Daicel Corporation, elute: hexane/ethanol=10/90, flow rate: 1.0 mL/min].

Optical purity: 99% (retention time: 12.5 min);
$^1$H-NMR (400 MHz, DMSO-$d_6$) δ: 12.26 (1H, s), 10.54 (1H, s), 8.38 (2H, s), 5.51 (1H, d, J=4 Hz), 4.44 (1H, dd, J=7 Hz, 4 Hz), 4.19-4.10 (1H, m), 3.88-3.79 (2H, m), 2.96-2.86 (1H, m), 2.82-2.72 (2H, m), 2.12-2.06 (1H, m), 1.90-1.73 (4H, m), 0.95-0.85 (4H, m);
MS (ESI) m/z: 423 (M+H)$^+$.

(Reference Example 54) 1-(Diphenylmethyl)-3-[1-(6-isopropoxypyridazin-3-yl)piperidin-4-yl]-1H-pyrazol-5-amine

[Formula 101]

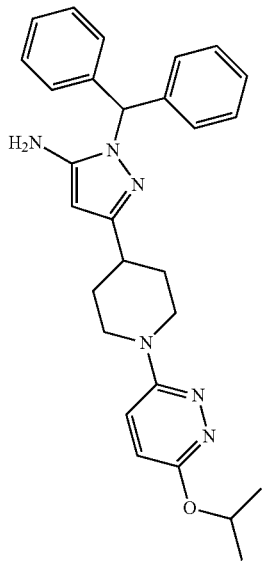

n-Butyllithium (1.6 M solution in hexane, 23 mL, 36.6 mmol) was added dropwise at −78° C. to a solution of anhydrous acetonitrile (1.92 mL, 36.6 mmol) in anhydrous THF (20 mL), and the mixture was stirred at the same temperature as above for 40 minutes. A solution of ethyl 1-[6-(isopropyloxy)pyridazin-3-yl]piperidine-4-carboxylate (compound described in the pamphlet of WO2013/187462, 4.30 g, 14.7 mmol) in anhydrous THF (20 mL) was added dropwise thereto at the same temperature as above, and the mixture was stirred for 40 minutes. Then, acetic acid (2.52 mL) was added thereto, and the temperature of the mixture was raised to room temperature. The reaction solution was separated into organic and aqueous layers by the addition of ethyl acetate and brine and further subjected to extraction with ethyl acetate three times. The obtained organic layer was dried over anhydrous sodium sulfate, and the solvent was distilled off under reduced pressure. The obtained residue was purified by silica gel column chromatography [elute: hexane/ethyl acetate=100/0-60/40 (gradient)] to obtain a synthesis intermediate (2.1 g).

The title compound (2.68 g, yield: 41%) was obtained through the same reaction as in the method described in Reference Example 12 using a portion (2.00 g) of the synthesis intermediate obtained by the procedures described above instead of the tert-butyl 4-(cyanoacetyl)piperidine-1-carboxylate.

$^1$H-NMR (400 MHz, CDCl$_3$) δ: 7.37-7.28 (6H, m), 7.22-7.20 (4H, m), 7.03 (1H, d, J=10 Hz), 6.75 (1H, d, J=10 Hz), 6.67 (1H, s), 5.44-5.38 (2H, m), 4.20-4.15 (2H, m), 3.23 (2H, s), 2.97 (2H, td, J=13 Hz, 3 Hz), 2.79 (1H, tt, J=12 Hz, 4 Hz), 2.04-1.98 (2H, m), 1.78-1.68 (2H, m), 1.37 (6H, d, J=6 Hz).

(Reference Example 55) 1-(Diphenylmethyl)-3-[1-(6-isopropoxypyridazin-3-yl)piperidin-4-yl]-4-(trifluoromethyl)-1,4,5,7-tetrahydro-6H-pyrazolo[3,4-b]pyridin-6-one

[Formula 102]

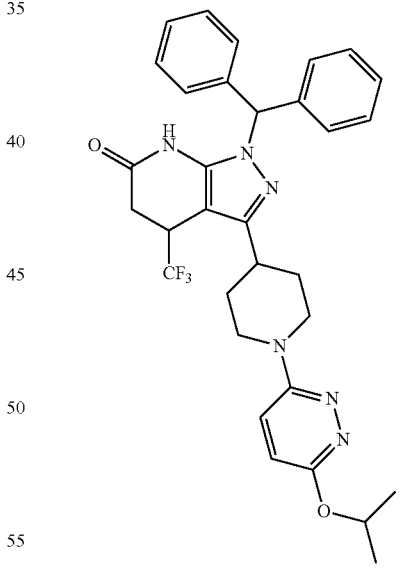

The same reaction as in the method described in Reference Example 41 was carried out using 1-(diphenylmethyl)-3-[1-(6-isopropoxypyridazin-3-yl)piperidin-4-yl]-1H-pyrazol-5-amine (2.28 g, 4.87 mmol) produced in Reference Example 54 instead of 3-{1-[5-(difluoromethoxy)pyridin-2-yl]piperidin-4-yl}-1-(diphenylmethyl)-1H-pyrazol-5-amine. To the obtained residue, diethyl ether and hexane were added, and the mixture was stirred. The precipitate was collected by filtration to obtain the title compound (2.38 g, yield: 83%).

$^1$H-NMR (400 MHz, CDCl$_3$) δ: 7.41-7.35 (6H, m), 7.14-7.10 (4H, m), 7.07 (1H, brs), 7.02 (1H, d, J=9 Hz), 6.76 (1H, d, J=9 Hz), 6.70 (1H, s), 5.43-5.36 (1H, m), 4.27-4.15 (2H, m), 3.65-3.56 (1H, m), 3.02-2.95 (2H, m), 2.86-2.78 (3H, m), 2.00-1.79 (4H, m), 1.37 (6H, d, J=6 Hz).

(Reference Example 56) Methyl 1-(diphenylmethyl)-5-hydroxy-6-oxo-3-[1-(6-isopropoxy-pyridazin-3-yl)piperidin-4-yl]-4-(trifluoromethyl)-4,5,6,7-tetrahydro-1H-pyrazolo[3,4-b]pyridine-5-carboxylate

[Formula 103]

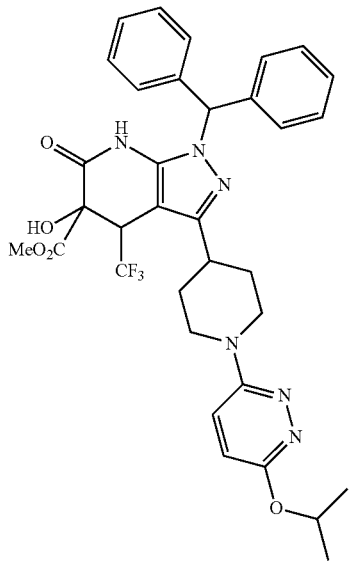

The same reaction as in the method described in Reference Example 42 was carried out using 1-(diphenylmethyl)-3-[1-(6-isopropoxypyridazin-3-yl)piperidin-4-yl]-4-(trifluoromethyl)-1,4,5,7-tetrahydro-6H-pyrazolo[3,4-b]pyridin-6-one (2.37 g, 4.01 mmol) produced in Reference Example 55 instead of 3-{1-[5-(difluoromethoxy)pyridin-2-yl]piperidin-4-yl}-1-(diphenylmethyl)-4-(trifluoromethyl)-1,4,5,7-tetrahydro-6H-pyrazolo[3,4-b]pyridin-6-one. To the obtained residue, methanol was added, and the mixture was stirred. The precipitate was collected by filtration to obtain the title compound (807 mg, yield: 31%).

$^1$H-NMR (400 MHz, CDCl$_3$) δ: 7.42-7.36 (6H, m), 7.16-7.14 (2H, m), 7.09-7.06 (2H, m), 7.01 (1H, d, J=10 Hz), 6.83 (1H, brs), 6.79 (1H, s), 6.75 (1H, d, J=9 Hz), 5.43-5.37 (1H, m), 4.26 (1H, s), 4.24-4.18 (2H, m), 3.90 (3H, s), 3.82-3.76 (1H, m), 3.00-2.92 (2H, m), 2.85-2.77 (2H, m), 2.03-1.73 (4H, m), 1.36 (6H, d, J=6 Hz).

(Reference Example 57) cis-1-(Diphenylmethyl)-5-hydroxy-3-[1-(6-isopropoxypyridazin-3-yl)piperidin-4-yl]-4-(trifluoromethyl)-1,4,5,7-tetrahydro-6H-pyrazolo[3,4-b]pyridin-6-one

[Formula 104]

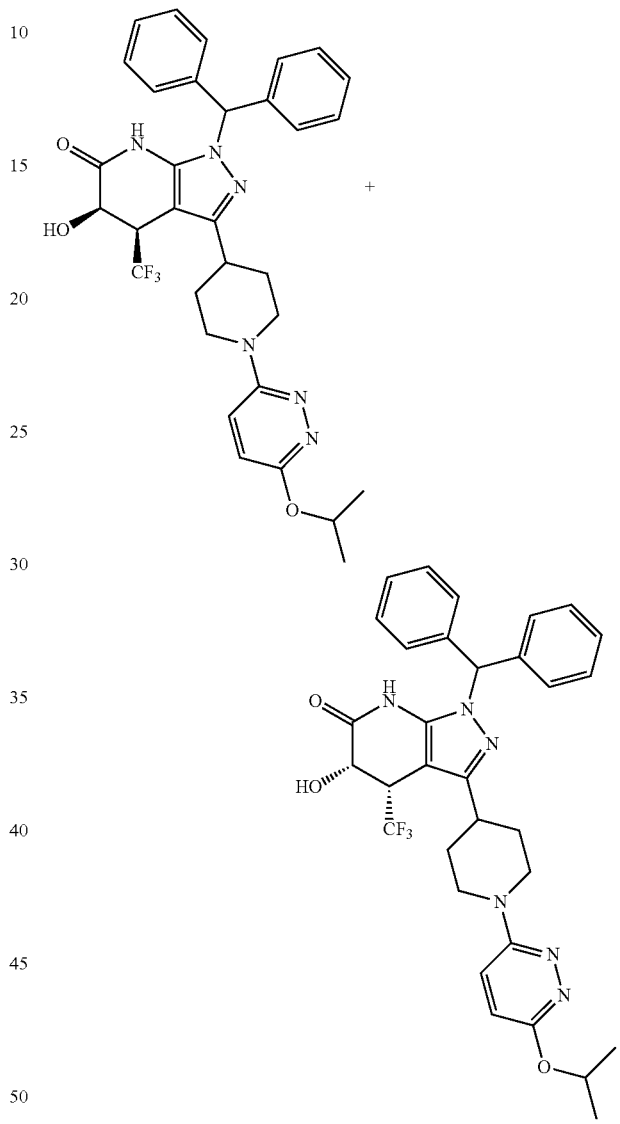

The title compound (716 mg, yield: 98%) was obtained through the same reaction as in the method described in Reference Example 43 using methyl 1-(diphenylmethyl)-5-hydroxy-6-oxo-3-[1-(6-isopropoxypyridazin-3-yl)piperidin-4-yl]-4-(trifluoromethyl)-4,5,6,7-tetrahydro-1H-pyrazolo[3,4-b]pyridine-5-carboxylate (804 mg, 1.21 mmol) produced in Reference Example 56 instead of methyl 3-{1-[5-(difluoromethoxy)pyridin-2-yl]piperidin-4-yl}-1-(diphenylmethyl)-5-hydroxy-6-oxo-4-(trifluoromethyl)-4,5,6,7-tetrahydro-1H-pyrazolo [3,4-b]pyridine-5-carboxylate.

$^1$H-NMR (400 MHz, CDCl$_3$) δ: 7.42-7.37 (6H, m), 7.12-7.06 (4H, m), 7.02 (1H, d, J=9 Hz), 6.76 (1H, d, J=9 Hz), 6.74-6.72 (2H, m), 5.44-5.37 (1H, m), 4.52 (1H, d, J=7 Hz), 4.28-4.17 (2H, m), 3.97-3.89 (1H, m), 3.69-3.67 (1H, m), 3.03-2.95 (2H, m), 2.86-2.78 (1H, m), 1.91 (4H, ddd, J=45 Hz, 15 Hz, 11 Hz), 1.37 (6H, d, J=6 Hz).

(Example 41) (+)-cis-5-Hydroxy-3-[1-(6-isopropoxypyridazin-3-yl)piperidin-4-yl]-4-(trifluoromethyl)-1,4,5,7-tetrahydro-6H-pyrazolo[3,4-b]pyridin-6-one

[Formula 105]

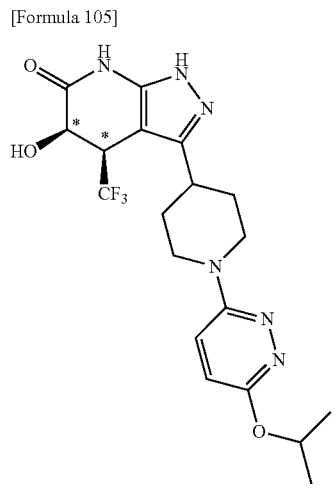 [SMILES: CC(C)Oc1ccc(N2CCC(c3n[nH]c4c3[C@@H](C(F)(F)F)[C@@H](O)C(=O)N4)CC2)nn1]

A synthesis intermediate (501 mg) was obtained through the same reaction as in the method described in Example 26 using cis-1-(diphenylmethyl)-5-hydroxy-3-[1-(6-isopropoxypyridazin-3-yl)piperidin-4-yl]-4-(trifluoromethyl)-1,4,5,7-tetrahydro-6H-pyrazolo[3,4-b]pyridin-6-one (714 mg, 1.18 mmol) produced in Reference Example 57 instead of cis-1-(diphenylmethyl)-5-hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one.

Triethylamine (0.172 mL, 1.24 mmol) and (+)-menthyl chloroformate (0.288 mL, 1.36 mmol) were added at 0° C. to a mixed suspension of a portion (498 mg) of the synthesis intermediate obtained by the procedures described above in THF (15 mL) and ethyl acetate (5 mL), and the mixture was stirred at the same temperature as above for 1 hour and then at room temperature for 3 hours. Triethylamine (23.5 µL, 0.170 mmol) and (+)-menthyl chloroformate (36.0 µL, 0.170 mmol) were further added thereto at room temperature, and the mixture was left overnight. To the reaction mixture, water was added, followed by extraction with ethyl acetate three times. The obtained organic layer was washed with brine and dried over anhydrous sodium sulfate, and the solvent was concentrated under reduced pressure. The obtained residue was purified by silica gel column chromatography [elute: hexane/ethyl acetate=100/0-60/40 (gradient)] to obtain each of a compound (107 mg) eluted first and a compound (119 mg) eluted second.

The title compound (64.7 mg, yield: 13%, optically active form) was obtained through the same reaction as in the method described in Example 36 using a portion (105 mg) of the compound eluted first obtained by the procedures described above instead of cis-5-hydroxy-3-[1-(5-isopropoxypyridin-2-yl)piperidin-4-yl]-4-(trifluoromethyl)-1,4,5,7-tetrahydro-6H-pyrazolo[3,4-b]pyridin-6-one.

$^1$H-NMR (400 MHz, DMSO-d$_6$) δ: 12.23 (1H, s), 10.54 (1H, s), 7.40 (1H, d, J=10 Hz), 6.94 (1H, d, J=10 Hz), 5.51 (1H, d, J=4 Hz), 5.28-5.21 (1H, m), 4.46-4.43 (1H, m), 4.33-4.26 (2H, m), 4.19-4.11 (1H, m), 3.02-2.95 (1H, m), 2.92-2.81 (2H, m), 1.86-1.65 (4H, m), 1.31 (6H, d, J=6 Hz); MS (ESI) m/z: 441 (M+H)$^+$;
$[α]_D^{25}$=+10° (DMF, c=1.01).

(Test Example 1) LCAT Activity Measurement (in Vitro)

A fraction composed of HDL3 (1.125 <specific gravity <1.210 g/mL) was obtained from the plasma of a healthy person by density gradient centrifugation. The obtained fraction was dialyzed against phosphate-buffered saline (pH 7.4) and used as an enzyme source and an acceptor for LCAT. Each test drug was prepared by dissolution in dimethyl sulfoxide. [$^{14}$C]Cholesterol containing DTNB (Ellman's reagent, final concentration: 0.5 mM), mercaptoethanol (final concentration: 12.5 mM), and 0.6% bovine serum albumin was added to phosphate-buffered saline (pH 7.4) containing 1 mg/mL HDL3, and the test drug was further added thereto at varying concentrations to adjust the whole amount to 80 µL. This mixture was incubated at 37° C. for approximately 16 hours. Then, a mixed solution of hexane and isopropanol (mixing ratio=3:2) was added thereto to stop the reaction. After stirring, the hexane layer was collected, and this layer was evaporated to dryness. A chloroform solution (concentration: 10 mg/mL) was added thereto, and the mixture was spotted onto a thin-layer silica gel plate and developed using a mixed solution of hexane, diethyl ether, and ethyl acetate (mixing ratio=85:15:2). The radioactivity of a portion corresponding to cholesterol oleate was measured using an imaging analyzer BAS-2500 (manufactured by Fujifilm Corp.). A sample non-supplemented with the test drug was similarly treated and assayed. The EC$_{50}$ value of LCAT activation was calculated according to the expression given below relative to LCAT activity in the sample non-supplemented with the test drug. The results are shown in Table 1.

$$Y = \text{Bottom} + \frac{(\text{Top} - \text{Bottom})}{1 + 10^{LogEC50-X}}$$ [Expression 1]

wherein X represents the logarithm of the concentration of the test drug;
Y represents the responsiveness (LCAT activity) of the test drug;
Top represents the maximum value (maximum plateau);
Bottom represents the minimum value (minimum plateau); and
EC$_{50}$ represents the 50% effective concentration.

TABLE 1

| Test compound | EC$_{50}$ (µM) |
| --- | --- |
| Compound of Example 1 | 0.88 |
| Compound of Example 2 | 0.040 |
| Compound of Example 3 | 0.013 |
| Compound of Example 4 | 0.022 |
| Compound of Example 5 | 0.16 |
| Compound of Example 6 | 2.22 |
| Compound of Example 7 | 0.11 |
| Compound of Example 8 | 0.63 |
| Compound of Example 9 | 0.027 |
| Compound of Example 10 | 0.34 |
| Compound of Example 11 | 0.029 |
| Compound of Example 12 | 0.035 |
| Compound of Example 13 | 0.037 |
| Compound of Example 14 | 0.38 |

TABLE 1-continued

| Test compound | EC$_{50}$ (μM) |
|---|---|
| Compound of Example 15 | 0.29 |
| Compound of Example 16 | 0.062 |
| Compound of Example 17 | 0.031 |
| Compound of Example 18 | 0.009 |
| Compound of Example 19 | 0.035 |
| Compound of Example 20 | 0.051 |
| Compound of Example 21 | 0.018 |
| Compound of Example 22 | 0.032 |
| Compound of Example 23 | 0.008 |
| Compound of Example 24 | 0.030 |
| Compound of Example 25 | 0.10 |
| Compound of Example 26 | 0.065 |
| Compound of Example 27 | 0.037 |
| Compound of Example 28 | 0.16 |
| Compound of Example 29 | 0.011 |
| Compound of Example 30 | 0.063 |
| Compound of Example 31 | 0.034 |
| Compound of Example 32 | 0.007 |
| Compound of Example 33 | 0.057 |
| Compound of Example 34 | 0.004 |
| Compound of Example 35 | 0.007 |
| Compound of Example 36 | 0.041 |
| Compound of Example 37 | 0.094 |
| Compound of Example 38 | 0.024 |
| Compound of Example 39 | 0.092 |
| Compound of Example 40 | 0.070 |
| Compound of Example 41 | 0.035 |

As seen from these results, the compound of the present invention has an excellent LCAT-activating effect and is useful as a medicament for the treatment or prophylaxis of diseases such as dyslipidemia and arteriosclerosis.

(Test Example 2) LCAT Activity Measurement (Plasma)

The plasma of a human, a cynomolgus monkey, or a human LCAT transgenic mouse is used as an enzyme source and an acceptor for LCAT. Each test drug is prepared by dissolution in dimethyl sulfoxide. [14C] Cholesterol containing DTNB (Ellman's reagent, final concentration: 0.5 mM), mercaptoethanol (final concentration: 12.5 mM), and 0.6% bovine serum albumin is added to 5 μL of each plasma and 45 μL of PBS, and the test drug is further added thereto at varying concentrations to adjust the whole amount to 80 μL. This mixture is incubated at 37° C. for approximately 16 hours. Then, a mixed solution of hexane and isopropanol (mixing ratio=3:2) is added thereto to stop the reaction. After addition of water and stirring, the hexane layer is collected, and this layer is evaporated to dryness. A chloroform solution (concentration: 10 mg/mL) is added thereto, and the mixture is spotted onto a thin-layer silica gel plate and developed using a mixed solution of hexane, diethyl ether, and ethyl acetate (mixing ratio=85:15:2). The radioactivity of a portion corresponding to cholesterol oleate is measured using an imaging analyzer BAS-2500 (manufactured by Fujifilm Corp.). A sample non-supplemented with the test drug is similarly treated and assayed. The EC$_{50}$ value of LCAT activation is calculated according to the expression given below relative to LCAT activity in the sample non-supplemented with the test drug.

$$Y = \text{Bottom} + \frac{(\text{Top} - \text{Bottom})}{1 + 10^{LogEC50-X}} \quad \text{[Expression 2]}$$

wherein X represents the logarithm of the concentration of the test drug;
Y represents the responsiveness (LCAT activity) of the test drug;
Top represents the maximum value (maximum plateau);
Bottom represents the minimum value (minimum plateau); and
EC$_{50}$ represents the 50% effective concentration.

(Test Example 3) LCAT Activity Measurement (Ex Vivo)

LCAT activity in the plasma of a cynomolgus monkey or a human LCAT transgenic mouse receiving each test drug is measured. [14C]Cholesterol containing DTNB (Ellman's reagent, final concentration: 0.26 mM), mercaptoethanol (final concentration: 2 mM), and 0.6% bovine serum albumin is added to 25 μL of each plasma to adjust the whole amount to 40 μL. This mixture is incubated at 37° C. for 1 hour. Then, a mixed solution of hexane and isopropanol (mixing ratio=3:2) is added thereto to stop the reaction. After addition of water and stirring, the hexane layer is collected, and this layer is evaporated to dryness. A chloroform solution (concentration: 10 mg/mL) is added thereto, and the mixture is spotted onto a thin-layer silica gel plate and developed using a mixed solution of hexane, diethyl ether, and ethyl acetate (mixing ratio=85:15:2). The radioactivity of a portion corresponding to cholesterol oleate is measured using an imaging analyzer BAS-2500 (manufactured by Fujifilm Corp.). The rate of change in LCAT activation at each point in time compared with LCAT activity before administration is calculated.

(Test Example 4) Drug Efficacy Test in Cynomolgus Monkeys

Each test drug was dissolved in a propylene glycol (Sigma-Aldrich Corp.)-Tween 80 (Sigma-Aldrich Corp.) mixed solution [4/1 (v/v)] or a 0.5% (w/v) methylcellulose aqueous solution, and the solution was orally administered to a cynomolgus monkey for 1 or 7 days. At day 1 or 7 of the administration period, blood was collected before administration and after administration, and plasma was obtained. The content of cholesterol in the plasma was measured using a commercially available assay kit (Cholesterol-E Wako, Wako Pure Chemical Industries, Ltd.). The lipoprotein profile was analyzed by HPLC (column: LipopropakXL, manufactured by Tosoh Corp.). The contents of HDL cholesterol and non-HDL cholesterol were calculated according to the following calculation expression:

Content of HDL cholesterol=Content of cholesterol in the plasma×(Peak area of HDL cholesterol/Total sum of peaks)

Content of non-HDL cholesterol=Content of cholesterol in the plasma×(Peak area of non-HDL cholesterol/Total sum of peaks)

The rate (%) of increase in HDL level after the administration of a single dose of 10 mg/kg compared with before administration was determined from AUC before administration and 24 hours after administration. The results are shown in Table 2.

TABLE 2

| Test compound | Rate of increase in HDL level after administration of single dose |
|---|---|
| Compound of Example 3 | 658 |
| Compound of Example 18 | 644 |
| Compound of Example 20 | 454 |
| Compound of Example 21 | 483 |
| Compound of Example 22 | 581 |

TABLE 2-continued

| Test compound | Rate of increase in HDL level after administration of single dose |
|---|---|
| Compound of Example 30 | 290 |
| Compound of Example 34 | 590 |
| Compound of Example 35 | 482 |

(Test Example 5) Drug Efficacy Test in Human LCAT Transgenic Mice

Each test drug is dissolved in a propylene glycol-Tween 80 mixed solution [4/1 (v/v)] or a 0.5% (w/v) methylcellulose aqueous solution, and the solution is orally administered to a human LCAT transgenic mouse for 1, 4, or 7 days. At day 1, 4, or 7 of the administration period, blood is collected before administration and after administration, and plasma is obtained. The content of cholesterol in the plasma is measured using a commercially available assay kit (Cholesterol-E Wako, Wako Pure Chemical Industries, Ltd.). The lipoprotein profile is analyzed by HPLC (column: LipopropakXL, manufactured by Tosoh Corp.). The contents of HDL cholesterol and non-HDL cholesterol are calculated according to the following calculation expression:

Content of HDL cholesterol=Content of cholesterol in the plasma×(Peak area of HDL cholesterol/Total sum of peaks)

Content of non-HDL cholesterol=Content of cholesterol in the plasma×(Peak area of non-HDL cholesterol/Total sum of peaks)

As seen from these results, the compound of the present invention exhibits an excellent LCAT-activating effect and is useful as a medicament for the treatment or prophylaxis of diseases such as dyslipidemia and arteriosclerosis.

(Formulation Example 1) Hard Capsule

Each standard two-piece hard gelatin capsule shell is filled with 100 mg of the compound of Example 1 in a powder form, 150 mg of lactose, 50 mg of cellulose, and 6 mg of magnesium stearate to produce a unit capsule, which is in turn washed and then dried.

(Formulation Example 2) Soft Capsule

A mixture of the compound of Example 2 put in a digestible oil, for example, soybean oil, cottonseed oil, or olive oil, is prepared and injected into a gelatin shell using a positive displacement pump to obtain a soft capsule containing 100 mg of the active ingredient, which is in turn washed and then dried.

(Formulation Example 3) Tablet

According to a routine method, a tablet is produced using 100 mg of the compound of Example 3, 0.2 mg of colloidal silicon dioxide, 5 mg of magnesium stearate, 275 mg of microcrystalline cellulose, 11 mg of starch, and 98.8 mg of lactose.

If desired, the tablet is coated.

(Formulation Example 4) Suspension

A suspension is produced to contain 100 mg of the compound of Example 4 pulverized into a fine powder, 100 mg of sodium carboxy methylcellulose, 5 mg of sodium benzoate, 1.0 g of a sorbitol solution (Japanese Pharmacopoeia), and 0.025 mL of vanillin in 5 mL.

(Formulation Example 5) Injection

The compound of Example 6 (1.5% by weight) is stirred in 10% by weight of propylene glycol, subsequently adjusted to a fixed volume with injectable water, and then sterilized to prepare an injection.

INDUSTRIAL APPLICABILITY

The compound represented by the general formula (I) of the present invention or a pharmacologically acceptable salt thereof has an excellent LCAT-activating effect and is particularly useful as an active ingredient in a therapeutic or prophylactic agent for arteriosclerosis, arteriosclerotic heart disease, coronary heart disease (including acute coronary syndromes, heart failure, myocardial infarction, angina pectoris, cardiac ischemia, cardiovascular disturbance, and restenosis caused by angiogenesis), cerebrovascular disease (including stroke and cerebral infarction), peripheral vascular disease (including peripheral arterial disease and diabetic vascular complications), dyslipidemia, LCAT deficiency, hypo-HDL-cholesterolemia, hyper-LDL-cholesterolemia, diabetes mellitus, hypertension, metabolic syndrome, Alzheimer's disease, cornea opacity, or renal disease, particularly, an anti-arteriosclerotic agent.

The invention claimed is:

1. A compound represented by the general formula (I) or a pharmacologically acceptable salt thereof:

[Formula 1]

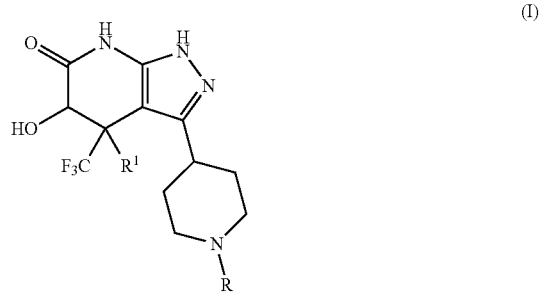

(I)

wherein R represents an optionally substituted aryl group (the substituent(s) is 1 to 3 identical or different groups selected from the group consisting of a halogen atom, a $C_{1-6}$ alkyl group, a $C_{3-7}$ cycloalkyl group, a trifluoromethyl group, a difluoromethoxy group, a trifluoromethoxy group, a cyano group, a $C_{1-6}$ alkoxy group, a $C_{3-7}$ cycloalkoxy group, a phenyl group, a $C_{2-7}$ alkoxycarbonyl group, a benzyloxycarbonyl group, a di($C_{1-6}$ alkyl)aminocarbonyl group, and a di($C_{1-6}$ alkyl) amino group) or an optionally substituted heteroaryl group (the heteroaryl is a 5- or 6-membered ring; the heteroatom(s) on the ring of the heteroaryl group is 1 or 2 nitrogen atoms, and the ring optionally further contains one nitrogen atom, oxygen atom, or sulfur atom; and the substituent(s) is 1 or 2 identical or different groups selected from the group consisting of a halogen atom, a $C_{1-6}$ alkyl group, a $C_{3-7}$ cycloalkyl group, a trifluoromethyl group, a difluoromethoxy group, a trifluoromethoxy group, a cyano group, a $C_{1-6}$ alkoxy group, a $C_{3-7}$ cycloalkoxy group, a phenyl group, a $C_{2-7}$ alkoxycarbonyl group, a benzyloxycarbonyl group, a di($C_{1-6}$ alkyl)aminocarbonyl group, and a di($C_{1-6}$ alkyl) amino group), and $R^1$ represents a hydrogen atom or a hydroxy group.

2. The compound according to claim 1 or a pharmacologically acceptable salt thereof, wherein R is an optionally substituted aryl group (the substituent(s) is 1 to 3 identical or different groups selected from the group consisting of a halogen atom, a $C_{1-6}$ alkyl group, a $C_{3-7}$ cycloalkyl group, a trifluoromethyl group, a difluoromethoxy group, a trifluoromethoxy group, a cyano group, a $C_{1-6}$ alkoxy group, a $C_{3-7}$ cycloalkoxy group, a phenyl group, a $C_{2-7}$ alkoxycarbonyl group, a benzyloxycarbonyl group, a di($C_{1-6}$ alkyl)aminocarbonyl group, and a di($C_{1-6}$ alkyl)amino group).

3. The compound according to claim 1 or a pharmacologically acceptable salt thereof, wherein R is a substituted aryl group (the substituent(s) is 1 or 2 identical or different groups selected from the group consisting of a chlorine atom, a fluorine atom, a $C_{1-3}$ alkyl group, a trifluoromethyl group, a difluoromethoxy group, a trifluoromethoxy group, a cyano group, and a $C_{1-6}$ alkoxy group).

4. The compound according to claim 1 or a pharmacologically acceptable salt thereof, wherein R is a substituted phenyl group (the substituent(s) is 1 or 2 identical or different groups selected from the group consisting of a chlorine atom, a difluoromethoxy group, a trifluoromethoxy group, and a cyano group).

5. The compound according to claim 1 or a pharmacologically acceptable salt thereof, wherein R is a substituted phenyl group (the substituent(s) is 1 or 2 identical or different groups selected from the group consisting of a difluoromethoxy group, a trifluoromethoxy group, and a cyano group).

6. The compound according to claim 1 or a pharmacologically acceptable salt thereof, wherein R is an optionally substituted heteroaryl group (the heteroaryl is a 5- or 6-membered ring; the heteroatom(s) on the ring of the heteroaryl group is 1 or 2 nitrogen atoms, and the ring optionally further contains one nitrogen atom, oxygen atom, or sulfur atom; and the substituent(s) is 1 or 2 identical or different groups selected from the group consisting of a halogen atom, a $C_{1-6}$ alkyl group, a $C_{3-7}$ cycloalkyl group, a trifluoromethyl group, a difluoromethoxy group, a trifluoromethoxy group, a cyano group, a $C_{1-6}$ alkoxy group, a $C_{3-7}$ cycloalkoxy group, a phenyl group, a $C_{2-7}$ alkoxycarbonyl group, a benzyloxycarbonyl group, a di($C_{1-6}$ alkyl)aminocarbonyl group, and a di($C_{1-6}$ alkyl)amino group).

7. The compound according to claim 1 or a pharmacologically acceptable salt thereof, wherein R is a substituted heteroaryl group (the heteroaryl is a 5- or 6-membered ring; the heteroatom on the ring of the heteroaryl group is one nitrogen atom, and the ring optionally further contains one nitrogen atom, oxygen atom, or sulfur atom; the substituent(s) is 1 or 2 identical or different groups selected from the group consisting of a halogen atom, a $C_{1-3}$ alkyl group, a $C_{3-6}$ cycloalkyl group, a trifluoromethyl group, a difluoromethoxy group, a trifluoromethoxy group, a cyano group, a $C_{1-3}$ alkoxy group, a $C_{2-4}$ alkoxycarbonyl group, and a benzyloxycarbonyl group).

8. The compound according to claim 1 or a pharmacologically acceptable salt thereof, wherein R is a substituted pyridyl, pyrimidyl, pyrazinyl, pyridazinyl, thiadiazolyl, or thiazolyl group (the substituent(s) is 1 or 2 identical or different groups selected from the group consisting of a chlorine atom, a fluorine atom, a $C_{1-3}$ alkyl group, a cyclopropyl group, a trifluoromethyl group, a difluoromethoxy group, a trifluoromethoxy group, a cyano group, a $C_{1-3}$ alkoxy group, a $C_{2-4}$ alkoxycarbonyl group, and a benzyloxycarbonyl group).

9. The compound according to claim 1 or a pharmacologically acceptable salt thereof, wherein R is a substituted pyridyl, pyrimidyl, pyrazinyl, or pyridazinyl group (the substituent(s) is 1 or 2 identical or different groups selected from the group consisting of an isopropyl group, a trifluoromethyl group, a difluoromethoxy group, a cyano group, and an isopropoxy group).

10. The compound according to claim 1 or a pharmacologically acceptable salt thereof, wherein R is a pyridyl, pyrimidyl, pyrazinyl, or thiadiazolyl group substituted by a trifluoromethyl group.

11. The compound according to claim 1 or a pharmacologically acceptable salt thereof, wherein R is a pyridyl, pyrimidyl, or pyrazinyl group substituted by a trifluoromethyl group.

12. The compound according to claim 1 or a pharmacologically acceptable salt thereof, wherein $R^1$ is a hydrogen atom.

13. The compound according to claim 12 or a pharmacologically acceptable salt thereof, wherein the compound or the salt is selected from the group consisting of:
5-hydroxy-4-(trifluoromethyl)-3-{1-[5-(trifluoromethyl) pyridin-2-yl]piperidin-4-yl}-1,4,5,7-tetrahydro-6H-pyrazolo[3,4-b]pyridin-6-one,
5-hydroxy-3-[1-(5-isopropoxypyridin-2-yl)piperidin-4-yl]-4-(trifluoromethyl)-1,4,5,7-tetrahydro-6H-pyrazolo [3,4-b]pyridin-6-one,
5-hydroxy-4-(trifluoromethyl)-3-{1-[6-(trifluoromethyl) pyridazin-3-yl]piperidin-4-yl}-1,4,5,7-tetrahydro-6H-pyrazolo[3,4-b]pyridin-6-one,
5-hydroxy-3-{1-[2-isopropyl-6-(trifluoromethyl)pyrimidin-4-yl]piperidin-4-yl}-4-(trifluoromethyl)-1,4,5,7-tetrahydro-6H-pyrazolo[3,4-b]pyridin-6-one,
5-hydroxy-4-(trifluoromethyl)-3-{1-[5-(trifluoromethyl) pyrazin-2-yl]piperidin-4-yl}-1,4,5,7-tetrahydro-6H-pyrazolo[3,4-b]pyridin-6-one,
5-hydroxy-4-(trifluoromethyl)-3-{1-[2-(trifluoromethyl) pyrimidin-5-yl]piperidin-4-yl}-1,4,5,7-tetrahydro-6H-pyrazolo[3,4-b]pyridin-6-one,
6-{4-[5-hydroxy-6-oxo-4-(trifluoromethyl)-4,5,6,7-tetrahydro-1H-pyrazolo[3,4-b]pyridin-3-yl]piperidin-1-yl}-4-(trifluoromethyl)pyridine-3-carbonitrile,
3-{1-[3-chloro-5-(trifluoromethyl)pyridin-2-yl]piperidin-4-yl}-5-hydroxy-4-(trifluoromethyl)-1,4,5,7-tetrahydro-6H-pyrazolo[3,4-b]pyridin-6-one,
5-hydroxy-4-(trifluoromethyl)-3-{(1-[4-(trifluoromethyl)-1,3-thiazol-2-yl]piperidin-4-yl}-1,4,5,7-tetrahydro-6H-pyrazolo[3,4-b]pyridin-6-one,
5-hydroxy-4-(trifluoromethyl)-3-{1-[6-(trifluoromethyl) pyridin-2-yl]piperidin-4-yl}-1,4,5,7-tetrahydro-6H-pyrazolo[3,4-b]pyridin-6-one,
5-hydroxy-4-(trifluoromethyl)-3-{1-[4-(trifluoromethyl) pyridin-2-yl]piperidin-4-yl}-1,4,5,7-tetrahydro-6H-pyrazolo[3,4-b]pyridin-6-one,
3-[1-(5-chloropyridin-2-yl)piperidin-4-yl]-5-hydroxy-4-(trifluoromethyl)-1,4,5,7-tetrahydro-6H-pyrazolo [3,4-b]pyridin-6-one,
5-hydroxy-4-(trifluoromethyl)-3-{1-[6-(trifluoromethyl) pyridin-3-yl]piperidin-4-yl}-1,4,5,7-tetrahydro-6H-pyrazolo[3,4-b]pyridin-6-one,
hydroxy-4-(trifluoromethyl)-3-{1-[5-(trifluoromethyl)-1, 3,4-thiadiazol-2-yl]piperidin-4-yl}-1,4,5,7-tetrahydro-6H-pyrazolo[3,4-b]pyridin-6-one, 5-hydroxy-4-(trifluoromethyl)-3-{1-[6-(trifluoromethyl)pyrimidin-4-yl]piperidin-4-yl}-1,4,5,7-tetrahydro-6H-pyrazolo[3,4-b]pyridin-6-one, 5-hydroxy-3-[1-(6-isopropoxypyridazin-3-yl)piperidin-4-yl]-4-(trifluoromethyl)-1,4,5,7-tetrahydro-6H-pyrazolo[3,4-b]pyridin-6-one, 5-hydroxy-3-[1-(6-isopropoxypyridazin-3-yl)piperidin-4-yl]-4-(trifluoromethyl)-1,4,5,7-tetrahydro-6H-pyrazolo[3,4-b]pyridin-6-one, and 3-[1-(2-cyclopropylpyrimidin-5-yl)piperidin-4-yl]-5-hydroxy-4-(trifluoromethyl)-1,4,5,7-tetrahydro-6H-pyrazolo [3,4-b]pyridin-6-one.

14. The compound according to claim 12 or a pharmacologically acceptable salt thereof, wherein the compound or the salt is selected from the group consisting of:

(+)-cis-5-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one, (+)-cis-5-hydroxy-4-(trifluoromethyl)-3-{1-[6-(trifluoromethyl)pyridazin-3-yl]piperidin-4-yl}-1,4,5,7-tetrahydro-6H-pyrazolo[3,4-b]pyridin-6-one, (+)-cis-5-hydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one, (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one, (+)-cis-6-{4-[5-hydroxy-6-oxo-4-(trifluoromethyl)-4,5,6,7-tetrahydro-1H-pyrazolo[3,4-b]pyridin-3-yl]piperidin-1-yl}-4-(trifluoromethyl)pyridine-3-carbonitrile, (+)-cis-3-[1-(5-chloropyridin-2-yl)piperidin-4-yl]-5-hydroxy-4-(trifluoromethyl)-1,4,5,7-tetrahydro-6H-pyrazolo[3,4-b]pyridin-6-one, (+)-cis-5-hydroxy-4-(trifluoromethyl)-3-{1-[6-(trifluoromethyl)pyridin-3-yl]piperidin-4-yl}-1,4,5,7-tetrahydro-6H-pyrazolo[3,4-b]pyridin-6-one, (+)-cis-hydroxy-4-(trifluoromethyl)-3-{1-[5-(trifluoromethyl)-1,3,4-thiadiazol-2-yl]piperidin-4-yl})-1,4,5,7-tetrahydro-6H-pyrazolo[3,4-b]pyridin-6-one, (+)-cis-5-hydroxy-4-(trifluoromethyl)-3-{1-[6-(trifluoromethyl)pyrimidin-4-yl]piperidin-4-yl})-1,4,5,7-tetrahydro-6H-pyrazolo[3,4-b]pyridin-6-one, (+)-cis-5-hydroxy-3-[1-(6-isopropoxypyridazin-3-yl)piperidin-4-yl]-4-(trifluoromethyl)-1,4,5,7-tetrahydro-6H-pyrazolo[3,4-b]pyridin-6-one, (+)-cis-5-hydroxy-3-[1-(6-isopropoxypyridazin-3-yl)piperidin-4-yl]-4-(trifluoromethyl)-1,4,5,7-tetrahydro-6H-pyrazolo[3,4-b]pyridin-6-one, and (+)-cis-3-[1-(2-cyclopropylpyrimidin-5-yl)piperidin-4-yl]-5-hydroxy-4-(trifluoromethyl)-1,4,5,7-tetrahydro-6H-pyrazolo[3,4-b]pyridin-6-one.

15. The compound according to claim 1 or a pharmacologically acceptable salt thereof, wherein $R^1$ is a hydroxy group.

16. The compound according to claim 15 or a pharmacologically acceptable salt thereof, wherein the compound or the salt is selected from the group consisting of:

4,5-dihydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one, and 4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one.

17. The compound according to claim 15 or a pharmacologically acceptable salt thereof, wherein the compound or the salt is selected from the group consisting of:

(+)-4,5-dihydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one, and (+)-4,5-dihydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one.

18. The compound according to claim 1 or a pharmacologically acceptable salt thereof, wherein R is a substituted phenyl group (the substituent(s) is 1 or 2 identical or different groups selected from the group consisting of a chlorine atom, a difluoromethoxy group, a trifluoromethoxy group, and a cyano group), and $R^1$ is a hydrogen atom.

19. The compound according to claim 1 or a pharmacologically acceptable salt thereof, wherein R is a substituted phenyl group (the substituent(s) is 1 or 2 identical or different groups selected from the group consisting of a difluoromethoxy group, a trifluoromethoxy group, and a cyano group), and $R^1$ is a hydrogen atom.

20. The compound according to claim 1 or a pharmacologically acceptable salt thereof, wherein R is a substituted pyridyl, pyrimidyl, pyrazinyl, pyridazinyl, thiadiazolyl, or thiazolyl group (the substituent(s) is 1 or 2 identical or different groups selected from the group consisting of a chlorine atom, a fluorine atom, a $C_{1-3}$ alkyl group, a cyclopropyl group, a trifluoromethyl group, a difluoromethoxy group, a trifluoromethoxy group, a cyano group, a $C_{1-3}$ alkoxy group, a $C_{2-4}$ alkoxycarbonyl group, and a benzyloxycarbonyl group), and $R^1$ is a hydrogen atom.

21. The compound according to claim 1 or a pharmacologically acceptable salt thereof, wherein R is a substituted pyridyl, pyrimidyl, pyrazinyl, or pyridazinyl group (the substituent(s) is 1 or 2 identical or different groups selected from the group consisting of an isopropyl group, a trifluoromethyl group, a difluoromethoxy group, a cyano group, and an isopropoxy group), and $R^1$ is a hydrogen atom.

22. The compound according to claim 1 or a pharmacologically acceptable salt thereof, wherein R is a pyridyl, pyrimidyl, or pyrazinyl group substituted by a trifluoromethyl group, and $R^1$ is a hydrogen atom.

23. The compound according to claim 1 or a pharmacologically acceptable salt thereof, wherein R is a substituted phenyl group (the substituent(s) is 1 or 2 identical or different groups selected from the group consisting of a chlorine atom, a difluoromethoxy group, a trifluoromethoxy group, and a cyano group), and $R^1$ is a hydroxy group.

24. The compound according to claim 1 or a pharmacologically acceptable salt thereof, wherein R is a substituted phenyl group (the substituent(s) is 1 or 2 identical or different groups selected from the group consisting of a difluoromethoxy group, a trifluoromethoxy group, and a cyano group), and $R^1$ is a hydroxy group.

25. The compound according to claim 1 or a pharmacologically acceptable salt thereof, wherein R is a substituted pyridyl, pyrimidyl, pyrazinyl, pyridazinyl, thiadiazolyl, or thiazolyl group (the substituent(s) is 1 or 2 identical or different groups selected from the group consisting of a chlorine atom, a fluorine atom, a $C_{1-3}$ alkyl group, a cyclopropyl group, a trifluoromethyl group, a difluoromethoxy group, a trifluoromethoxy group, a cyano group, a $C_{1-3}$ alkoxy group, a $C_{2-4}$ alkoxycarbonyl group, and a benzyloxycarbonyl group), and $R^1$ is a hydroxy group.

26. The compound according to claim 1 or a pharmacologically acceptable salt thereof, wherein R is a substituted pyridyl, pyrimidyl, pyrazinyl, or pyridazinyl group (the substituent(s) is 1 or 2 identical or different groups selected from the group consisting of an isopropyl group, a trifluoromethyl group, a difluoromethoxy group, a cyano group, and an isopropoxy group), and $R^1$ is a hydroxy group.

27. The compound according to claim 1 or a pharmacologically acceptable salt thereof, wherein R is a pyridyl, pyrimidyl, or pyrazinyl group substituted by a trifluoromethyl group, and $R^1$ is a hydroxy group.

28. The compound according to claim 1 or a pharmacologically acceptable salt thereof, wherein the trifluoromethyl group at the 4-position of the pyrazolopyridine ring and the hydroxy group at the 5-position thereof are cis to each other.

29. The compound according to claim 1 or a pharmacologically acceptable salt thereof, wherein the optical rotation is (+).

30. A pharmaceutical composition comprising a compound according to claim 1 or a pharmacologically acceptable salt thereof as an active ingredient.

31. A method for activating LCAT, comprising administering an effective amount of a compound according to claim 1 or a pharmacologically acceptable salt thereof to a human.

32. A method for treatment of arteriosclerosis, comprising administering an effective amount of a compound according to claim 1 or a pharmacologically acceptable salt thereof to a human.

33. A method for prophylaxis of arteriosclerosis, comprising administering an effective amount of (+)-cis-5-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one or a pharmacologically acceptable salt thereof to a human in need thereof.

* * * * *

UNITED STATES PATENT AND TRADEMARK OFFICE
CERTIFICATE OF CORRECTION

PATENT NO. : 9,796,709 B2
APPLICATION NO. : 15/100654
DATED : October 24, 2017
INVENTOR(S) : H. Kobayashi et al.

It is certified that error appears in the above-identified patent and that said Letters Patent is hereby corrected as shown below:

| Column | Line | Error |
|---|---|---|
| 117 (Claim 33, Line 3) | 26 | "{I-" should read --{1- -- |

Signed and Sealed this
Third Day of July, 2018

Andrei Iancu
*Director of the United States Patent and Trademark Office*